US008315816B2

(12) United States Patent
Dawkins et al.

(10) Patent No.: US 8,315,816 B2
(45) Date of Patent: Nov. 20, 2012

(54) METHODS OF GENETIC ANALYSIS INVOLVING THE AMPLIFICATION OF COMPLEMENTARY DUPLICONS

(75) Inventors: Roger L. Dawkins, Canning Vale South (AU); John Anthony Millman, Shoalwater Bay (AU); Joseph Frederick Williamson, Victoria Park (AU)

(73) Assignee: Genetic Technologies Limited, Victoria (AU)

( * ) Notice: Subject to any disclaimer, the term of this patent is extended or adjusted under 35 U.S.C. 154(b) by 862 days.

(21) Appl. No.: 11/816,522

(22) PCT Filed: Feb. 16, 2006

(86) PCT No.: PCT/AU2006/000206
§ 371 (c)(1),
(2), (4) Date: Sep. 26, 2008

(87) PCT Pub. No.: WO2006/086846
PCT Pub. Date: Aug. 24, 2006

(65) Prior Publication Data
US 2009/0150080 A1      Jun. 11, 2009

(30) Foreign Application Priority Data

Feb. 16, 2005   (AU) ................................ 2005900728

(51) Int. Cl.
*G01N 33/48* (2006.01)
(52) U.S. Cl. ............. 702/20; 435/6; 435/69.1; 530/350; 702/19
(58) Field of Classification Search .............. 702/19, 702/20; 435/6, 91.2, 287.2, 69.1; 530/350
See application file for complete search history.

(56) References Cited

U.S. PATENT DOCUMENTS

| 5,296,375 | A | 3/1994 | Kricka et al. |
| 5,304,487 | A | 4/1994 | Wilding et al. |
| 5,856,174 | A | 1/1999 | Lipshutz et al. |
| 5,904,824 | A | 5/1999 | Oh |
| 5,990,294 | A | 11/1999 | Murphy et al. |
| 6,383,747 | B1 | 5/2002 | Dawkins et al. |
| 6,432,646 | B1 * | 8/2002 | Gasser et al. ............... 435/6.13 |
| 6,775,622 | B1 | 8/2004 | Holloway |

(Continued)

FOREIGN PATENT DOCUMENTS
WO            94/05414         3/1994

OTHER PUBLICATIONS

Ning, "SSAHA: a fast search method for large DNA databases" Genome Research, Cold Spring Harbor Laboratory Press, Woodbury, NY, US, vol. 11, No. 10, Oct. 1, 2001, pp. 1725-1729, abstract.

(Continued)

*Primary Examiner* — John H Le
(74) *Attorney, Agent, or Firm* — Sheridan Ross P.C.

(57) ABSTRACT

The invention relates to methods for genetic analysis of DNA sequences containing complementary duplicons which are duplicated and linked DNA sequences separated by an intermediate sequence. Furthermore, the invention relates to the Bidirectional Amplification of Complementary Duplicons (BACD) using a single primer. The amplification of complementary duplicons can be used for a variety of purposes such as, determining the species from which a genomic DNA sample is derived, or used as a marker for a trait of interest. Also provided are methods for analyzing large datasets which can be used to identify primers useful for the genomic analysis methods of the invention.

16 Claims, 32 Drawing Sheets

Information stored around each nucleotide in sequence

U.S. PATENT DOCUMENTS

| | | | | |
|---|---|---|---|---|
| 7,323,305 | B2* | 1/2008 | Leamon et al. | 435/6 |
| 7,718,403 | B2* | 5/2010 | Kamberov et al. | 435/91.2 |
| 2002/0016444 | A1* | 2/2002 | Mueller et al. | 530/350 |
| 2003/0119104 | A1* | 6/2003 | Perkins et al. | 435/69.1 |
| 2003/0224356 | A1* | 12/2003 | Knoll et al. | 435/6 |
| 2004/0086861 | A1 | 5/2004 | Omori | |
| 2007/0105103 | A1* | 5/2007 | Takeda et al. | 435/6 |
| 2007/0111213 | A1* | 5/2007 | Wang et al. | 435/6 |
| 2007/0111239 | A1* | 5/2007 | Yssel et al. | 435/6 |

OTHER PUBLICATIONS

O'Donovan et al., "Removing redundancy in SWISS-PROT and TrEMBL" BioInformatics Applications Note, vol. 15, No. 3, Jan. 1, 1999, pp. 258-259.

Supplementary European Search Report for European Application No. 06704883.5, mailed Dec. 8, 2009.

Alix, K. et al., "Inter-Alu-like species-specific sequences in the Saccharum complex," Theor. Appl. Genet. 99:962-968 (1999).

Antunez-de-Mayolo, G. et al., "Phylogenetics of worldwide human populations as determined by polymorphic Alu insertions," Electrophoresis 23:3346-3356 (2002).

Arcot, S.S. et al., "Alu Fossil Relics—Distribution and Insertion Polymorphism," Genome Res. 6:1084-1092 (1996).

Baurens, F-C. et al., "Inter-Alu PCR like genomic profiling in banana," Euphytica 99:137-142 (1998).

Bartolome, C. et al., "On the Abundance and Distribution of Transposable Elements in the Genome of Drosophila melanogaster," Mol. Biol. Evol. 19(6):926-937 (2002).

Batzer, M.A. and Deininger, P.L., "Alu Repeats and Human Genomic Diversity," Nature 3:370-380 (May 2002).

Batzer et al., "Standardized Nomenclature for Alu Repeats," J. Mol. Evol. 42:3-6 (1996).

Batzer, M.A. et al., "Genetic Variation of Recent Alu Insertions in Human Populations," J. Mol. Evol. 42:22-29 (1996).

Bedell, J.A. et al., "Masker Aid: a performance enhancement to RepeatMasker," Bioinformatics 16(11):1040-1041 (2000).

Bridgland, L. et al., "Three duplicons form a novel chimeric transcription unit in the pericentromeric region of chromosome 22q11," Hum. Genet. 112:57-61 (2003).

Cattley, S.K. et al., "Further characterization of MHC hAplotypes demonstrates conservation telomeric of HLA-A: update of the 4AOH and 101HW cell panels," Eur. J. Immunogen. 27:397-426 (2000).

Christian, S.L. et al., "Large genomc duplicons map to sites of instability in the Prader-Willi/Angelman syndrome chromosome region (15q11-q13)," Hum. Mol. Genet. 8(6):1025-1037 (1999).

Clough, J.E. et al., "Computer Simulation of Transposable Element Evolution: Random Template and Strict Master Models," J. Mol. Evol. 42:52-58 (1996).

Deininger, P.L. and Batzer, M.A., "Alu Repeats and Human Disease," Mol. Genet. Metabol. 67:183-193 (1999).

Flavell, A.J. et al., "Ty1-copia group retrotransposons are ubiquitous and heterogeneous in higher plants," Nucl. Acids Res. 20(14):3639-3644 (1992).

Jurka, J. et al., "Censor—A program for identification and elimination of repetitive elements from DNA sequences," Computers Chem. 20(1):119-121(1996.

Kapitonov, V. and Jurka, J., "The Age of Alu Subfamilies," J. Mol. Evol. 42:59-65 (1996).

Kass, D.H. et al., "Sporadic Amplification of ID Elements in Rodents," J. Mol. Evol. 42:7-14 (1996).

Kulski, J.K. et al., "The Association Between HLA-A Alleles and an Alu Dimorphism Near HLA-G," J. Mol. Evol. 53:114-123 (2001).

Kulski, J.K. et al., "Genomc and Phylogenetic Analysis of the S10A7 (Psoriasin) Gene Duplications Within the Region of the S100 Gene Cluster on Human Chromosome 1q21," J. Mol. Evol. 56:397-406 (2003).

Lee, R.N. et al., "Retrotransposon Mys Was Active During Evolution of the Peromyscus leucopus-maniculatus Complex," J. Mol. Evol. 42:44-51 (1996).

Lerat, E. et al., "Codon Usage by Transposable Elements and Their Host Genes in Five Species," J. Mol. Evol. 54:625-637 (2002).

Lozovskaya, E.R. et al., "Genomc regulation of transposable elements in Drosophila," Curr. Opinion Genet. Dev. 5:768-773 (1995).

Lupski, J.R. "Genomc disorders: structural features of the genome can lead to DNA rearrangements and human disease traits," TIG 14(10):417-422 (Oct. 1998).

McCollum, A.M. et al., "Evidence for the adaptive significance of an LTR retrotransposon sequence in a Drosophila heterochromatic gene," BMC Evolutionary Biology 2, 7pp, (2002).

Meignin, C. et al., "The 5' Untranslated Region and Gag Product of Idefix, a Long Terminal Repeat-Retrotransposon from Drosophila melanogaster, Act Together to Initiate a Switch between Translated and Untranslated States of the Genomic mRNA," Mol. Cell. Biol. 23(22):8246-8254 (Nov. 2003).

Miriami, E. et al., "Conserved sequence elements associated with exon skipping," Nucl. Acids Res. 31(7):1974-1983 (2003).

Nelson, D.L. et al., "Alu polymerase chain reaction: A method for rapid isolation of human-specific sequences from complex DNA sources," Proc. Natl. Acad. Sci. USA 86:6686-6690 (Sep. 1989).

Novick, G.E., "Polymorphic human specific Alu insertions as markers for human identification," Electrophoresis 16:1596-1601 (1995).

Ostertag, E.M., "SVA Elements are Nonautonomous Retrotransposons that Cause Disease in Humans," Am. J. Hum. Genet. 73:1444-1451 (2003).

Ovchinnikov, I. et al., "Tracing the LINEs of human evolution," Proc. Natl. Acad. Sci. 99(16):10522-10527 (Aug. 2002).

Perez-Gonzalez, C.E. et al., "R1 and R2 Retrotransposition and Deletion in the rDNA Loci on the X and Y Chromosomes of Drosophila melanogaster," Genetics 165:675-685 (Oct. 2003).

Ricci, V. et al., "An Alu-mediated rearrangement as cause of exon skipping in Hunter disease," Hum. Genet. 112:419-425 (2003).

Saglio, G. et al., "A 76-kb duplicon maps close to the BCR gene on chromosome 22 and the ABL gene on chromosome 9: Possible involvement in the genesis of the Philadelphia chromosome translocation," Proc. Natl. Acad. Sci. 99(15):9882-9887 (Jul. 2002).

SanMiguel, P. et al., "The paleontology of intergene retrotransposons of maize," Nature Genetics 20:43-45 (Sep. 1998).

Santos, F.R. et al., "A polymorphic L1 retroposon insertion in the centromere of the human Y chromosome," Hum. Mol. Genet. 9(3):421-430 (2000).

Shedlock, A.M. and Okada, N., "SINE insertions: powerful tools for molecular systematics," BioEssays 22:148-160 (2000).

Smit, A.F.A., "Interspersed repeats and other mementos of transposable elements in mammalian genomes," Curr. Opinion Genet. Dev. 9:657-663 (1999).

Smit, A.F.A., "The origin of interspersed repeats in the human genome," Curr. Opin. Genet. Dev. 6:743-748 (1996).

Smit, A.F.A., "Ancestral, Mammalian-wide Subfamilies of LINE-1 Repetitive Sequences," J. Mol. Biol. 246:401-417 (1995).

Smit, A.F.A. and Riggs, A.D., "Tiggers and other DNA transposon fossils in the human genome," Proc. Natl. Acad. Sci. USA 93:1443-1448 (Feb. 1996).

Stenger, J.E., et al., "Biased Distribution of Inverted and Direct Alus in the Human Genome: Implications for Insertion, Exclusion, and Genome Stability,"Genome Res. 11:12-27 (2001).

Sorek, R. et al., "Alu-Containing Exons are Alternatively Spliced," Genome Res. 12:1060-1067 (2002).

Vieira, C. et al., "Evolution of Genome Size in Drosophila. Is the Invader's Genome Being Invaded by Transposable Elemlents?" Mol. Biol. Evol. 19(7):1154-1161 (2002).

Wang, S., "The distribution and copy number of copia-like retrotransposons in rice (Oryza sativa L.) and their implications in the organization and evolution of the rice genome," Proc. Natl. Acad. Sci. USA 96:6824-6828 (Jun. 1999).

Zhang, W.J. et al., "Differences in Gene Copy Number Carried by Different MHC Ancestral Haplotypes," J. Exp. Med. 171:2101-2114 (Jun. 1990).

Zietkiewicz, E., "Mosaic Evolution of Rodent B1 Elements," J. Mol. Evol. 42:66-72 (1996).

LaRosa, G.J. et al., "Conserved sequence and structural elements in the HIV-1 principal neutralizing determinant," Science 249:932-935 (1990).

LaRosa G.J. et al., "Conserved sequence and structural elements in the HIV-1 principal neutralizing determinant: Corrections and clarifications," Science 251:811 (1991).

LaRosa G.J. et al., "Conserved sequence and structural elements in the HIV-1 principal neutralizing determinant: Further clarifications," Science 253:1146 (1991).

Maraia, R.J. et al., "Multiple dispersed loci produce small cytoplasmic Alu RNA," Mol. Cell. Biol. 13:4233-4241 (1993).

Shaikh, T.H. et al., "cDNAs derived from primary and small cytoplasmic Alu (scAlu) transcripts," J. Mol. Biol. 271 (2):222-234 (1997).

Zietkiewicz, E. et al., "A young Alu subfamily amplified independently in human and African great apes lineages," Nucl. Acids Res. 22(25):5608-5612 (1994).

* cited by examiner

Hypothetical example
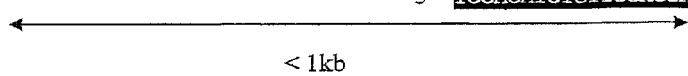
< 1kb
Actual examples
Human
AC022027
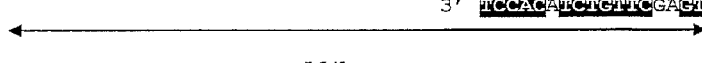
564bp
AL592226
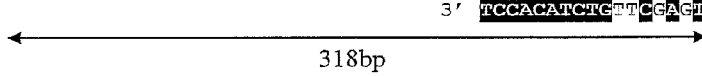
318bp
AP001964
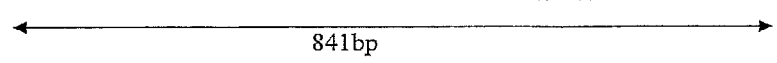
841bp
AC089999
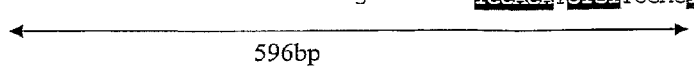
596bp
Figure 1A

AL121921/HSJ560I16

```
        5'      ATGAGCTTG-TCTACACCT 3'
H4  3'     CGACGGTGTGGACCCGAAATGTGGAGGGTGA..//..GGCACTCCTCCTCTGTTCTTGGGGG
H4  5'     GCTGCCACACCTGGGCTTTACACCTCCCACT..//..CCGTGAGGAGGAGACAAGAACCCCC
                                              3'     TCCACATCTGTTCGAGTA 5'
```
<----------------- 369bp ----------------->

Mouse gi28510350
```
        5'      ATGAGCTTGTCTACACCT 3'
M11        GACCCCCTTCGAACGAGGTGGAAACTA..//..CACGTTCCACATCTCTACGAAAATAAAC
M11        CTGGGGGAAGCTTGCTCCACCTTTGAT..//..GTGCAAGGTGTAGAGATGCTTTATTTG
                                              3'  TCCACATCTGTTCGAGTA 5'
```

.....gcagctgcttgaaggcgaggcgcatggcgggcgggcagcgccccacggagcccacgatggcgtccacgatgggcccag
gtagcccgtcagcagcccaggctggtctccgcatctgctcctccgagagtgcgcctttgaaggagatcctcctggagggg
ccggcggagcagctcagcctcggggcacaacatctgcctgctccaaaccctccaccggccccgctgagctccgagaggaCTC
ATCTTCCCTCCACGTCCGCAGCCTCCTTCCTGCCCCTTCCCACCGGGTTTCTTGCTGTTGCTTAAACACGATGAGCTCATTC
CCATCCTGCAGCCTTTGCACTGGCTTATCTCCGTGCCCAGAACACTCTCCCGTTAAATGTTAAATCTCCGCAACACTCCCTT
CCTCACCCCCTGCAAGTCTTTGCTTAGATGTCCCCTCCCCTGCGAGGCTGCCCCTGTCCTCACCCTCTGGAATATTGCAGGC
CTCTCCCCTCCCTCGTTTATTCCATTCCCTGGTCCCATTCAATAACCTTTTCCCAACCAGGCCCGGTGGCTCATGCCTGTAA
TCCCAGCACTCTGGGAGGCCGAGGGGGCAGGTCACTTGAGACCAGGAGTTCAAGACCAGCCTGGCCAACATGGTGAAACTCC
ATCTCCACCAAAAAATACAAAAATTAGCCCAGCGTGGTGGTGCACGCCTATAATCTCAGCTACTTGGGATGCTGAGGCAGGA
GAATCGCTTCAATATGGGAAGTGGAGGTTGCAGTGAGTTCGAGATCGCACCACTGCACTGCAGCCTGGGTGACACAGCGAGAC
TCCATCTCAAAAAATAAATAAATAAATAAATAAACCTTCTTCCTCCAGTTGCTCATTATCTGTCTCCCCCCAGAATAGGGAC
TTGGGACTATTTGTTCCCTACTGTATCGTCAGTGTTCAGCCCAGAGCCTGGCACTCAATcattgttttgttttgtggatgct
agaacagcacttttccatctgcaattattgtgttcctttctttctttacagattgaggg..
                                                                     |(Primer atgagCTTGtCtACACCT*)
...........................................................tctgtCTTGCCCACACCTaga
gtgacagctgggggttctcagccccACTGTGTCCTGGACCCAACGTGCTGAGCCCTGGACTTGTCTCTGGCATGG
TCTCTTTTAATCCTAACAGCAACTTGATGGGGTAAGTAGCCTTACTTGTTCCCGTTTAACAGATAAGAAAACTGA
GGCTCAGAGAGGTTACTGGGGAGATGGCACAGCTGAGAATAGAACCCAGGACTGCCAACTCCACAGCCTGCCTGC
AACCctgccctgtccaggtccctacatgccctgtcccatgggtgcccactgagtttcctccatcgttatcaag
tgtgctaggaaaagccctcaacttggagtctcacagatggactgtgtccttctgctcaggGCCTGGGATCAAATC
CTTGCTCTGTAATTTCCTGGCTGTATGACCTTAGGCAAGTGACCTTCCCTCTCTGAGGCTCAGTTGCATCATCAG
TAAGAGGGGGTCATGATGCCTGCCTCTAAAGTAGTCAGAAGGTGTgGACAgcacaAggaaagatcctctcctgtc
                                             (TCCACAtCTGTtcgagTa* Primer)

...tctgccacggtccccagtggataccccagcaacaattttccacagctccaggcttgtgggttagacaggagaaggtt
ctggagagaaaggaggagcccacggagggatggaatgaccccagccactgctctgcttcctcccaatctcattgagctctc
cacgatctcccttgcaggcaggcccactcagagaccgccaacaccacaataataaaaatcgctaatgttggggaccccagc
agcacagcagtaaatatcactaatgtcgaggagccccagcagcacagtaataaagatcactaatgcttgtggagcacatgca
tgactcagttaacggagcagaggtcatgagcccacgtttcaggtgataatattctccagctggataagggacattttag
aagtagtgtgtgcattaagtagaagaacattggatcaatatttaggttttttaattttaaaaaatctgattatGCCAGGCA
CGGTTGTTCACGCCTGTAATCCCAGCACTTCGGGAGACCAAGGCAGGAGGATTGCTTGAGCCCAGGAGTTCGAGACCAGCCT
GGGCAATGTGGCAAAACCCTGTCTCTGCTAAAAATGTAAAAACTTAGCTGGGCATGGTGGTGTGCGCCTATAGTCCCAGCTA
CTCAGGAGGCTGAGGTGGAAAAATTACCTGAGCCCGGGAAGTTGACGCTGCAGTGAGCTGTGGTCACACCACTGCACCCCAG
CCTGGGTGACAGAGTAAAACCTTGTCTCAAAAAAAAAAAAAAAAGAAAAAAAGGAAAAgaaaagaagcaacttaacca

Repeat sequence:

| SW score | perc div. | perc del. | perc ins. | query sequence | position in query begin | end | (left) | matching repeat | repeat class/family | position in repeat begin | end | (left) | ID |
|---|---|---|---|---|---|---|---|---|---|---|---|---|---|
| 481 | 32.1 | 10.9 | 3.9 | h3 | 241 | 545 | (3431) | + L2 | LINE/L2 | 2837 | 3181 | (132) | 1 |
| 1978 | 12.0 | 0.3 | 0.3 | h3 | 546 | 851 | (3125) | + AluSx | SINE/Alu | 3 | 308 | (0) | 2 |
| 481 | 32.1 | 10.9 | 3.9 | h3 | 852 | 958 | (3018) | + L2 | LINE/L2 | 3181 | 3279 | (34) | 1 |
| 479 | 27.9 | 12.2 | 4.9 | h3 | 1087 | 1290 | (2686) | C MIR | SINE/MIR | (28) | 234 | 16 | 4 |
| 533 | 25.8 | 3.8 | 0.0 | h3 | 1422 | 1553 | (2423) | + MIR | SINE/MIR | 46 | 182 | (80) | 5 |
| 2074 | 15.7 | 0.0 | 0.3 | h3 | 2066 | 2377 | (1599) | + AluJb | SINE/Alu | 2 | 312 | (0) | 6 |

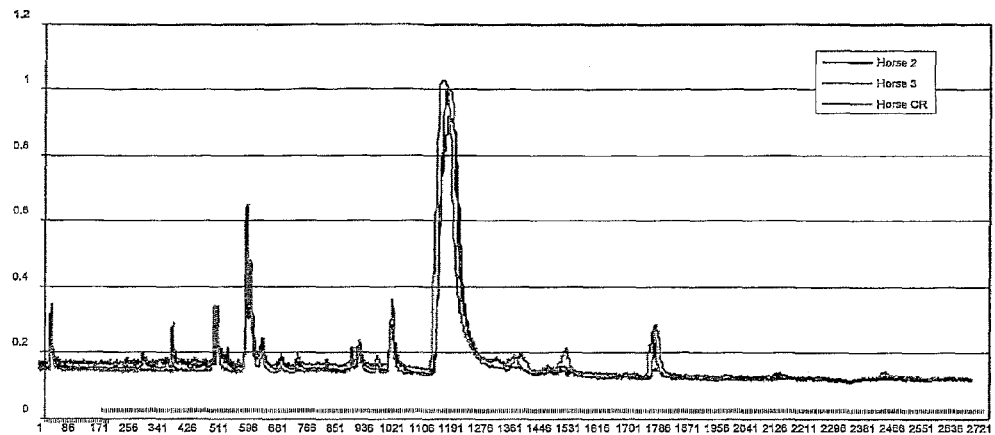
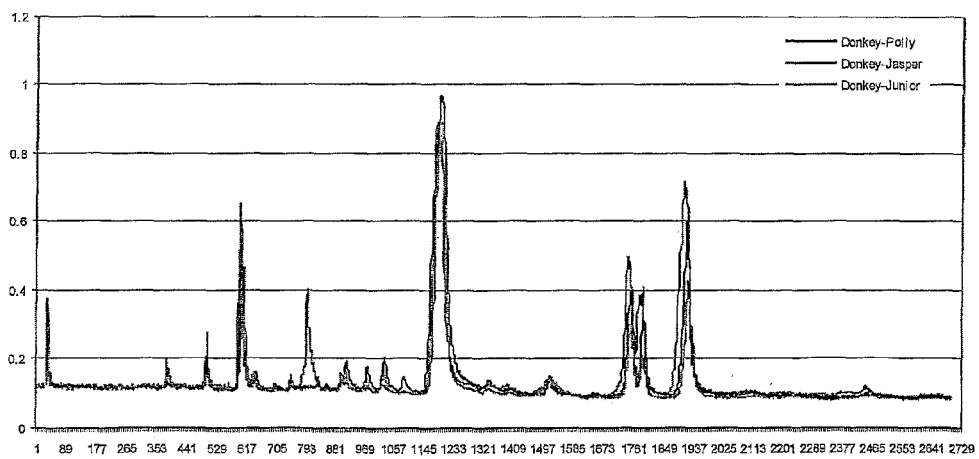
Figure 15A

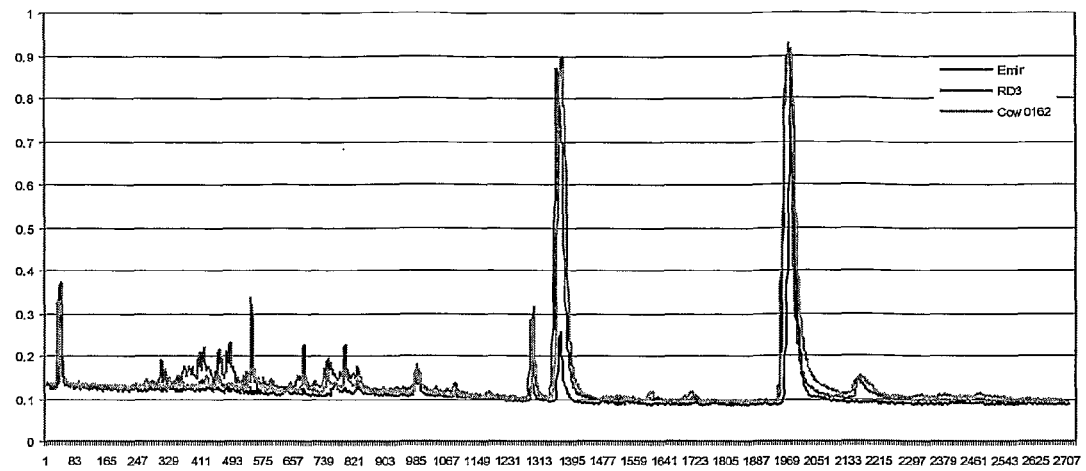
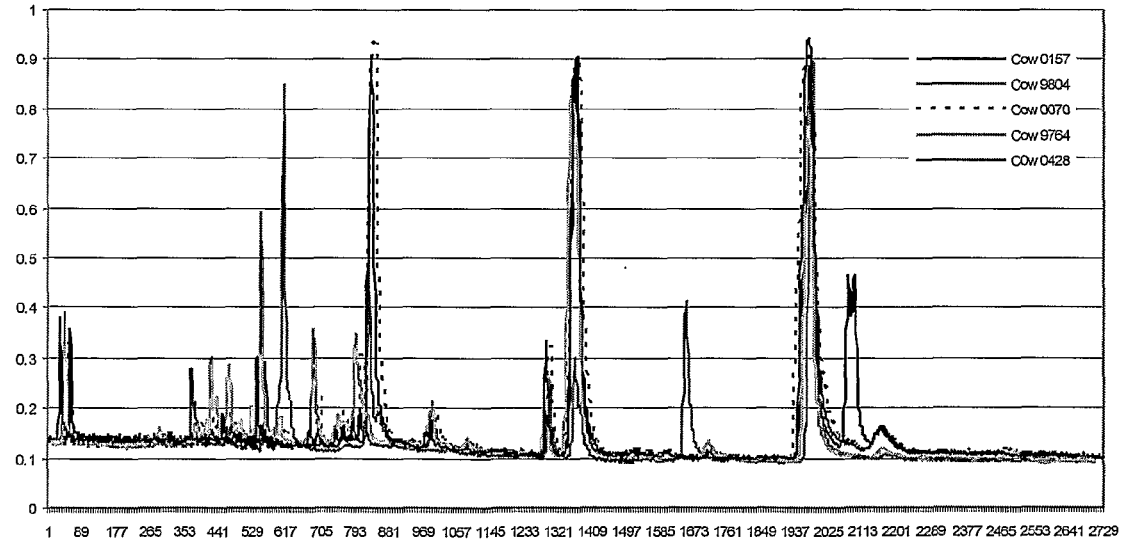
Figure 16

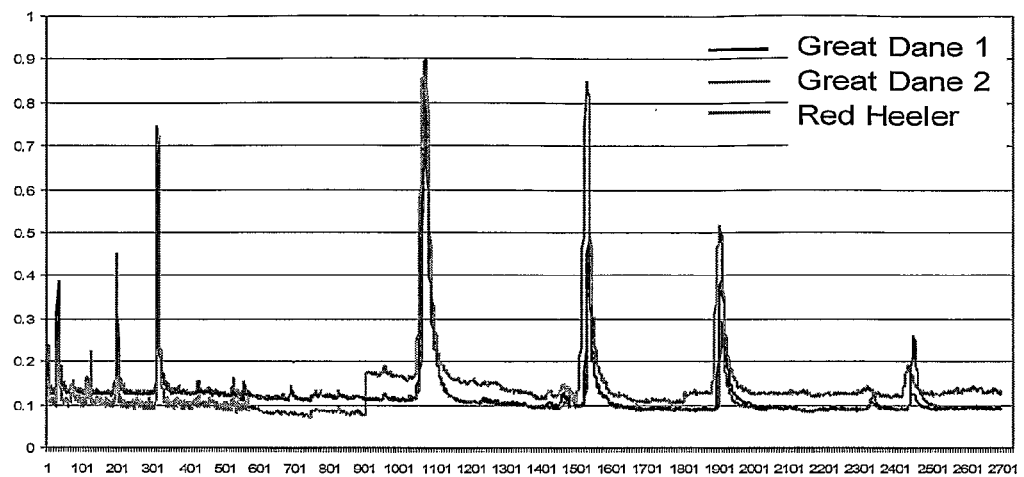
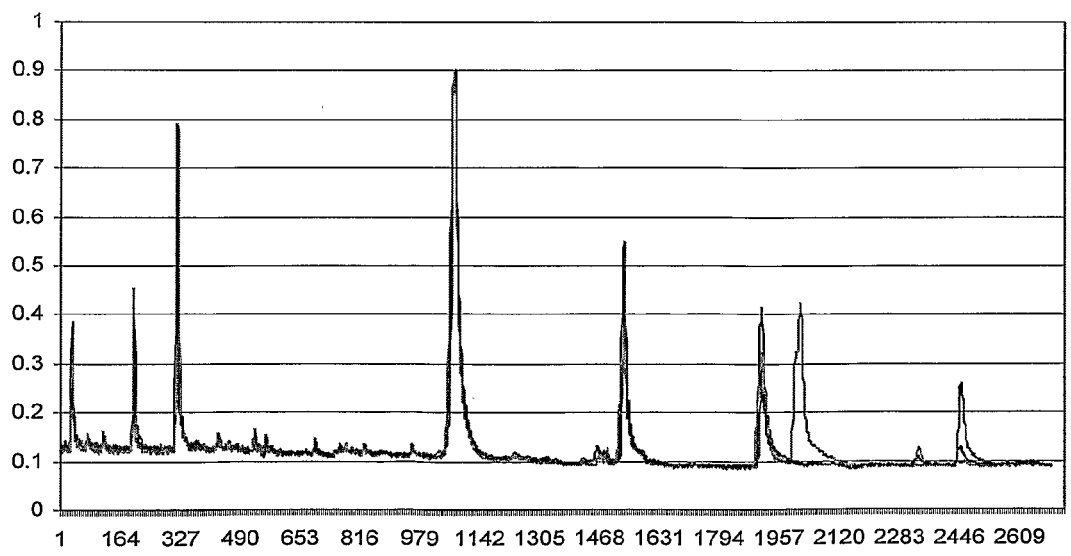
Figure 17

| Sequence 1 offset | Sequence 2 offset | relationship |
|---|---|---|
| 234 | 245 | F F (forward, forward) |
| 234 | 7890 | F RC (forward, reverse) |
| 1200 | 1500 | F F (forward, forward) |
| 1225 | 1526 | F F (forward, forward) |
| 1252 | 1551 | F F (forward, forward) |
| 1400 | 1700 | F F (forward, forward) |
| 1426 | 1726 | F F (forward, forward) |
| | | |
| | | |

Two indels difference in sequence (1200/1500)
1 SNP between sequences (1225/1526 area)
One indel difference between (1400/1700 area)

Figure 21

Information stored around each nucleotide in sequence

| Primary list | Actual sequence | Complement | Offset same | | | | | | | | Repeats |
|---|---|---|---|---|---|---|---|---|---|---|---|
| position | Nucleotide | | O1 | O2 | O3 | O4 | O5 | O6 | O7 | O8 | |
| 1 | A | T | 4 | 9 | 13 | 17 | 22 | 26 | 30 | 35 | |
| 2 | C | G | 4 | 9 | 13 | 17 | 22 | 26 | 30 | 37 | |
| 3 | T | A | 4 | 9 | 13 | 17 | 22 | 26 | 30 | 35 | |
| 4 | G | C | 4 | 5 | 9 | 13 | 17 | 18 | 22 | 26 | |
| 5 | A | T | 5 | 9 | 13 | 18 | 22 | 26 | 31 | 35 | |
| 6 | C | G | 5 | 9 | 13 | 18 | 22 | 26 | 31 | 35 | |
| 7 | T | A | 5 | 9 | 13 | 18 | 22 | 26 | 31 | 35 | |
| 8 | G | C | 1 | 5 | 9 | 13 | 14 | 18 | 22 | 34 | |
| 9 | G | C | 4 | 8 | 12 | 13 | 17 | 21 | 33 | 34 | |
| 10 | A | T | 4 | 8 | 13 | 17 | 21 | 26 | 30 | 35 | |
| 11 | C | G | 4 | 8 | 13 | 17 | 21 | 26 | 30 | 36 | |
| 12 | T | A | 4 | 8 | 12 | 17 | 21 | 26 | 30 | 35 | |
| 13 | G | C | 4 | 8 | 9 | 13 | 17 | 21 | 22 | 26 | |
| 14 | A | T | 4 | 9 | 13 | 17 | 22 | 26 | 31 | 35 | |
| 15 | C | G | 4 | 9 | 13 | 17 | 22 | 26 | 30 | 35 | |
| 16 | T | A | 4 | 9 | 13 | 17 | 22 | 26 | 31 | | |
| 17 | G | C | 4 | 5 | 9 | 13 | 17 | 18 | 22 | 26 | |
| 18 | A | T | 5 | 9 | 13 | 18 | 22 | 26 | 31 | 35 | |
| 19 | C | G | 5 | 9 | 13 | 18 | 22 | 26 | 31 | 35 | |
| 20 | T | A | 5 | 9 | 13 | 18 | 22 | 26 | 31 | 35 | |
| 21 | G | C | 1 | 5 | 9 | 13 | 14 | 18 | 22 | 34 | |
| 22 | G | C | 4 | 8 | 12 | 13 | 17 | 21 | 33 | 34 | |
| 23 | A | T | 4 | 8 | 13 | 17 | 21 | 26 | 30 | 35 | |
| 24 | | G | 4 | 8 | 13 | 17 | 21 | 26 | 30 | 36 | |
| 25 | T | A | 4 | 8 | 12 | 17 | 21 | 26 | 30 | 35 | |
| 26 | | C | 4 | 8 | 9 | 13 | 17 | 21 | 22 | 26 | |
| 27 | | T | 4 | 9 | 13 | 17 | 22 | 26 | 31 | 35 | |
| 28 | | G | 4 | 9 | 13 | 17 | 22 | | | | |
| 29 | | A | 4 | 9 | 13 | 17 | 22 | | | | |
| 30 | | C | 4 | 5 | 9 | 13 | 17 | | | | |
| 31 | | T | 5 | 9 | 13 | 18 | 22 | | | | |
| 32 | | G | 5 | 9 | 13 | 18 | 22 | | | | |
| 33 | | A | 5 | 9 | 13 | 18 | | | | | |
| 34 | | C | 1 | 5 | 9 | 13 | 14 | | | | |
| 35 | | C | 4 | 8 | 12 | 13 | 17 | | | | |
| 36 | | T | 4 | 8 | 13 | 17 | 21 | | | | |
| 37 | | G | 4 | 8 | 13 | 17 | 21 | | | | |
| 38 | | A | 4 | 8 | 12 | 17 | 21 | | | | |
| 39 | | C | 4 | 8 | 9 | 13 | 17 | | | | |
| 40 | | T | 4 | 9 | 13 | 17 | 22 | | | | |
| 41 | | G | | | | | | | | | |

Figure 23

|  | Position in sequence | D=5 | | D=6 | | D=7 | | D=8 | | D=9 | | D=10 | |
|---|---|---|---|---|---|---|---|---|---|---|---|---|---|
|  |  | S1 | S2 | S1 | S2 | S1 | S2 | S1 | S2 | S1 | S2 | S1 | S2 |
| n |  | 123 | 93 | 80 | 22 | 44 | 67 | 43 | 52 | 34 | 87 | 246 | 5 |
| n+1 |  | 456 | 49 | 68 | 52 | 44 | 9 | 70 | 13 | 84 | 9 | 456 | 96 |
| n+2 |  | 789 | 51 | 21 | 36 | 25 | 3 | 34 | 31 | 26 | 15 | 666 | 54 |
| n+3 |  | 1122 | 88 | 85 | 23 | 6 | 98 | 6 | 98 | 12 | 66 | 876 | 71 |
| n+4 |  | 1455 | 88 | 2 | 40 | 4 | 94 | 15 | 83 | 12 | 28 | 1086 | 7 |
| n+5 |  | 1789 | 64 | 81 | 37 | 3 | 99 | 87 | 80 | 44 | 17 | 1296 | 78 |
| n+6 |  | 2121 | 29 | 28 | 44 | 65 | 13 | 76 | 67 | 70 | 75 | 246 | 8 |
| n+7 |  | 2454 | 90 | 82 | 3 | 98 | 54 | 48 | 84 | 20 | 80 | 1506 | 49 |
| n+8 |  | 2787 | 123 | 6 | 96 | 15 | 86 | 55 | 14 | 12 | 14 | 1506 | 76 |
| n+9 |  | 567 | 456 | 1 | 90 | 56 | 81 | 34 | 98 | 28 | 48 | 1506 | 246 |
| n+10 |  | 678 | 789 | 99 | 91 | 95 | 85 | 48 | 92 | 40 | 88 | 75 | 93 |
| n+11 |  | 789 | 1122 | 98 | 95 | 75 | 91 | 35 | 57 | 56 | 36 | 21 | 17 |
| n+12 |  | 900 | 1455 | 46 | 29 | 81 | 84 | 81 | 93 | 55 | 94 | 80 | 246 |
| n+13 |  | 1011 | 1788 | 46 | 0 | 32 | 80 | 19 | 95 | 77 | 93 | 54 | 19 |
| n+14 |  | 81 | 2121 | 91 | 49 | 36 | 5 | 15 | 17 | 85 | 35 | 5 | 17 |
| n+15 |  | 13 | 789 | 54 | 98 | 17 | 46 | 85 | 12 | 99 | 83 | 72 | 246 |
| n+16 |  | 68 | 1011 | 75 | 45 | 19 | 28 | 72 | 59 | 12 | 91 | 31 | 51 |
| n+17 |  | 789 | 900 | 84 | 16 | 20 | 20 | 87 | 5 | 89 | 37 | 62 | 87 |
| n+18 |  | 15 | 90 | 26 | 32 | 17 | 97 | 8 | 94 | 41 | 57 | 28 | 33 |
| n+19 |  | 71 | 678 | 38 | 60 | 93 | 86 | 21 | 23 | 57 | 4 | 76 | 35 |
| n+20 |  | 18 | 567 | 44 | 81 | 64 | 1506 | 50 | 4 | 63 | 96 | 5 | 71 |
| n+21 |  | 23 | 789 | 89 | 8 | 91 | 1506 | 64 | 49 | 76 | 47 | 55 | 6 |
| n+22 |  | 57 | 75 | 45 | 16 | 23 | 1506 | 66 | 27 | 62 | 88 | 5 | 85 |
| n+23 |  | 27 | 436 | 20 | 24 | 20 | 20 | 9 | 16 | 19 | 75 | 0 | 67 |
| n+24 |  | 45 | 69 | 90 | 86 | 3 | 1296 | 43 | 39 | 74 | 77 | 54 | 46 |
| n+25 |  | 30 | 10 | 84 | 92 | 89 | 1086 | 33 | 70 | 10 | 68 | 66 | 81 |
| n+26 |  | 61 | 6 | 37 | 88 | 43 | 876 | 9 | 72 | 57 | 85 | 67 | 4 |
| n+27 |  | 48 | 9 | 30 | 21 | 13 | 666 | 64 | 96 | 25 | 81 | 58 | 21 |
| n+28 |  | 8 | 96 | 83 | 67 | 13 | 456 | 62 | 73 | 34 | 43 | 79 | 26 |
| n+29 |  | 86 | 57 | 94 | 45 | 22 | 20 | 85 | 18 | 50 | 22 | 10 | 22 |
| n+30 |  | 99 | 31 | 11 | 77 | 41 | 23 | 19 | 13 | 68 | 38 | 82 | 58 |

Forward sequence      n..n+9, n+11..n+16, n+18..n+24
Reverse Complement      n+29..n+23, n+21..n+17, n+15..n+6

Figure 24

| n | Position | D=5 S1 | D=5 S2 | D=6 S1 | D=6 S2 | D=7 S1 | D=7 S2 | D=8 S1 | D=8 S2 | D=9 S1 | D=9 S2 | D=10 S1 | D=10 S2 |
|---|---|---|---|---|---|---|---|---|---|---|---|---|---|
| n | P | 123 | 70 | 42 | 34 | 32 | 21 | 25 | 9 | 93 | 77 | 246 | 87 |
| n+1 | o | 456 | 57 | 50 | 9 | 60 | 39 | 18 | 72 | 84 | 15 | 456 | 66 |
| n+2 | s | 789 | 77 | 89 | 40 | 16 | 70 | 53 | 54 | 45 | 81 | 666 | 87 |
| n+3 | i | 1122 | 59 | 2 | 56 | 16 | 47 | 48 | 38 | 95 | 44 | 876 | 88 |
| n+4 | t | 1455 | 15 | 74 | 59 | 57 | 53 | 73 | 55 | 25 | 51 | 1086 | 81 |
| n+5 | i | 1789 | 42 | 19 | 25 | 45 | 97 | 81 | 33 | 55 | 53 | 1296 | 99 |
| n+6 | o | 2121 | 37 | 79 | 48 | 54 | 1 | 77 | 99 | 14 | 36 | 1506 | 71 |
| n+7 | n | 2454 | 56 | 67 | 26 | 90 | 10 | 0 | 94 | 77 | 47 | 1506 | 54 |
| n+8 |   | 2787 | 123 | 42 | 54 | 46 | 18 | 76 | 7 | 23 | 33 | 1506 | 76 |
| n+9 |   | 567 | 456 | 35 | 28 | 81 | 87 | 2 | 62 | 82 | 10 | 1506 | 246 |
| n+10 |   | 678 | 789 | 87 | 45 | 64 | 82 | 45 | 70 | 14 | 38 | 99 | 93 |
| n+11 | i | 289 | 1122 | 61 | 27 | 90 | 90 | 45 | 66 | 80 | 5 | 28 | 17 |
| n+12 | n | 480 | 1455 | 71 | 10 | 64 | 64 | 84 | 20 | 16 | 6 | 79 | 246 |
| n+13 |   | 1011 | 1788 | 63 | 37 | 70 | 6 | 28 | 78 | 50 | 16 | 66 | 19 |
| n+14 |   | 10 | 2121 | 91 | 24 | 36 | 14 | 26 | 4 | 2 | 18 | 77 | 17 |
| n+15 |   | 78 | 289 | 32 | 38 | 17 | 93 | 35 | 32 | 17 | 40 | 70 | 523 |
| n+16 | s | 71 | 1011 | 51 | 88 | 19 | 65 | 14 | 90 | 73 | 80 | 60 | 92 |
| n+17 | e | 436 | 900 | 21 | 24 | 20 | 48 | 62 | 11 | 48 | 97 | 63 | 81 |
| n+18 | q | 10 | 90 | 74 | 75 | 17 | 49 | 61 | 75 | 40 | 39 | 2 | 89 |
| n+19 | u | 11 | 678 | 61 | 65 | 93 | 13 | 88 | 42 | 12 | 4 | 32 | 78 |
| n+20 | e | 19 | 567 | 53 | 70 | 64 | 1506 | 32 | 52 | 51 | 39 | 88 | 73 |
| n+21 | n | 16 | 698 | 16 | 48 | 91 | 1506 | 70 | 90 | 83 | 41 | 14 | 76 |
| n+22 | c | 50 | 62 | 3 | 33 | 23 | 1506 | 41 | 7 | 92 | 28 | 29 | 19 |
| n+23 | e | 74 | 654 | 80 | 28 | 37 | 20 | 73 | 91 | 1 | 19 | 29 | 11 |
| n+24 |   | 13 | 24 | 47 | 54 | 3 | 1296 | 77 | 8 | 38 | 0 | 51 | 12 |
| n+25 |   | 71 | 20 | 7 | 5 | 68 | 1086 | 75 | 92 | 27 | 4 | 96 | 11 |
| n+26 |   | 64 | 71 | 98 | 69 | 82 | 876 | 68 | 43 | 89 | 50 | 0 | 79 |
| n+27 |   | 91 | 11 | 52 | 47 | 97 | 666 | 97 | 82 | 68 | 57 | 36 | 30 |
| n+28 |   | 82 | 91 | 84 | 96 | 38 | 456 | 28 | 11 | 78 | 19 | 72 | 39 |
| n+29 |   | 16 | 40 | 89 | 53 | 9 | 491 | 96 | 0 | 83 | 58 | 76 | 85 |
| n+30 |   | 36 | 21 | 9 | 81 | 96 | 23 | 54 | 15 | 47 | 27 | 15 | 90 |
| n+31 |   | 16 | 66 | 5 | 51 | 8 | 37 | 54 | 78 | 4 | 91 | 9 | 56 |
| n+32 |   | 14 | 97 | 63 | 8 | 78 | 3 | 14 | 66 | 62 | 48 | 45 | 91 |
| n+1004 |   | 1455 | 19 | 98 | 20 | 45 | 97 | 4 | 45 | 79 | 15 | 1086 | 20 |
| n+1005 |   | 1789 | 77 | 38 | 7 | 69 | 50 | 52 | 54 | 8 | 76 | 1296 | 95 |
| n+1006 |   | 2121 | 84 | 81 | 5 | 4 | 44 | 44 | 42 | 98 | 38 | 1506 | 9 |
| n+1007 |   | 2454 | 21 | 6 | 4 | 20 | 38 | 70 | 824 | 89 | 13 | 1506 | 43 |
| n+1008 |   | 2787 | 123 | 43 | 2 | 38 | 51 | 15 | 41 | 78 | 5 | 1506 | 76 |
| n+1009 |   | 567 | 456 | 15 | 70 | 70 | 17 | 15 | 70 | 74 | 91 | 1506 | 64 |
| n+1010 |   | 678 | 789 | 65 | 72 | 16 | 35 | 99 | 54 | 52 | 11 | 4 | 93 |
| n+1011 |   | 534 | 1122 | 46 | 65 | 58 | 31 | 31 | 70 | 78 | 31 | 92 | 17 |
| n+1012 |   | 900 | 1455 | 58 | 0 | 74 | 11 | 92 | 61 | 99 | 59 | 78 | 246 |
| n+1013 |   | 1011 | 1788 | 24 | 65 | 76 | 20 | 68 | 75 | 64 | 60 | 31 | 19 |
| n+1014 |   | 33 | 2121 | 60 | 34 | 36 | 91 | 79 | 70 | 95 | 20 | 25 | 17 |
| n+1015 |   | 289 | 2454 | 432 | 66 | 17 | 47 | 29 | 2 | 84 | 88 | 31 | 246 |
| n+1016 |   | 62 | 1011 | 89 | 14 | 19 | 39 | 84 | 17 | 97 | 90 | 71 | 69 |
| n+1017 |   | 5 | 900 | 2 | 79 | 45 | 79 | 65 | 35 | 83 | 43 | 59 | 50 |
| n+1018 |   | 47 | 90 | 27 | 33 | 17 | 47 | 98 | 18 | 38 | 66 | 24 | 51 |
| n+1019 |   | 68 | 298 | 36 | 90 | 93 | 5 | 95 | 50 | 33 | 19 | 67 | 56 |
| n+1020 |   | 1455 | 91 | 52 | 19 | 70 | 28 | 58 | 50 | 35 | 86 | 1086 | 99 |
| n+1021 |   | 94 | 567 | 97 | 62 | 64 | 1506 | 45 | 66 | 46 | 5 | 246 | 38 |
| n+1022 |   | 68 | 298 | 25 | 29 | 91 | 1506 | 3 | 2 | 65 | 92 | 246 | 31 |
| n+1023 |   | 34 | 58 | 63 | 98 | 23 | 1506 | 35 | 83 | 97 | 29 | 51 | 85 |
| n+1024 |   | 21 | 436 | 3 | 32 | 37 | 1506 | 77 | 80 | 62 | 51 | 85 | 71 |
| n+1025 |   | 77 | 25 | 78 | 84 | 3 | 1296 | 88 | 32 | 92 | 67 | 72 | 16 |
| n+1026 |   | 0 | 34 | 49 | 98 | 13 | 1086 | 48 | 37 | 50 | 48 | 1 | 41 |
| n+1027 |   | 89 | 75 | 64 | 59 | 88 | 876 | 19 | 51 | 2 | 79 | 14 | 88 |
| n+1028 |   | 42 | 95 | 24 | 63 | 87 | 666 | 94 | 60 | 62 | 7 | 85 | 33 |
| n+1029 |   | 62 | 89 | 12 | 38 | 42 | 456 | 89 | 17 | 26 | 80 | 28 | 98 |
| n+1030 |   | 9 | 40 | 7 | 52 | 60 | 20 | 32 | 47 | 79 | 60 | 58 | 246 |
| n+1031 |   | 31 | 71 | 87 | 73 | 56 | 23 | 32 | 39 | 24 | 58 | 97 | 4 |

Forward sequence          n..n+23
Reverse Complement        n+1029..n+1007

Figure 25

METHODS OF GENETIC ANALYSIS INVOLVING THE AMPLIFICATION OF COMPLEMENTARY DUPLICONS

CROSS REFERENCE TO RELATED APPLICATIONS

This application is a national stage application under 35 U.S.C. 371 of PCT Application No. PCT/AU06/000206 having an international filing date of 16 Feb., 2006, which designated the United States, which PCT application claimed the benefit of Australian Application No. 2005900728 filed 16 Feb., 2005, the entire disclosure of each of which is incorporated herein by reference.

FIELD OF THE INVENTION

The invention broadly relates to the fields of molecular biology and genetics. More specifically, the invention relates to methods for genetic analysis of DNA sequences containing complementary duplicons, i.e. duplicated and linked DNA sequences separated by an intermediate sequence. Furthermore, the invention relates to the Bidirectional Amplification of Complementary Duplicons (BACD) using a single primer, and methods of identifying single primers useful therefor. The amplification of complementary duplicons can be used for a variety or purposes such as, but not limited to, determining the species from which a sample comprising genomic DNA is derived, or used as a marker for a trait of interest.

BACKGROUND OF THE INVENTION

Genomes evolve both by acquiring new sequences and by rearranging/mutating existing sequences.

Rearrangements of genomes are sponsored by processes internal to the genome. One cause is unequal recombination which results from mis-pairing by the cellular systems for homologous recombination. Non-reciprocal recombination results in duplication or rearrangement of loci. Duplication of sequences within a genome provides a major source of new sequences. One copy of the sequence can retain its original function while the other may evolve into a new function. Furthermore, significant differences between individual genomes are found at the molecular level because of polymorphic variations caused by recombination.

Another major cause of variation is provided by transposable elements or transposons. These are discrete sequences in the genome that are mobile, i.e. they are able to transpose themselves to other locations within the genome. The mark of a transposon is that it moves directly from one site in the genome to another. Unlike most other processes involved in genome restructuring transposition does not rely on any relationship between the sequences at the donor and recipient sites. Transposons may provide a major source of mutations in the genome.

Transposons fall into two general classes. The first class includes transposons which exist as sequences of DNA coding for proteins that are able directly to manipulate DNA so as to propagate themselves within the genome. The second class of transposons are related to retroviruses and the source of their mobility is the ability to make DNA copies of their RNA transcripts; the DNA copies then become intergrated at new sites in the genome. These transposons are often termed retroposons, retrotransposons or retroviral-like elements (RLEs).

Mobile elements make up over 45% of the human genome. These elements continue to amplify and, as a result of negative effects of their transposition, they contribute to numerous human diseases (Deininger and Batzer, 1999; Ricci et al., 2003; Sorek et al., 2002). All eukaryotic genomes contain mobile elements, although the proportion and activity of the classes of elements are generally thought to vary widely between genomes. They use extensive cellular resources in their replication, expression and amplification. There is considerable debate as to whether they are primarily an intracellular plague that attacks the host genome and exploits cellular resources, or whether they are tolerated because of their occasional positive influences in genome evolution.

Transposable elements can promote rearrangements of the genome, directly or indirectly. The transposition event itself may cause deletions or inversions or lead to the movement of a host sequence to a new location. Further transposons serve as substrates for cellular recombination systems by functioning as "portable regions of homology"; two copies of a transposon at different locations (even on different chromosomes) may provide sites for reciprocal recombination. Such exchanges result in deletions, insertions, inversions or translocations.

The inventor's earlier application, granted as U.S. Pat. No. 6,383,747, describes methods of analysing ancestral haplotypes. Ancestral haplotypes are DNA sequences from multigene complexes such as the Human Major Histocompatibility Complex (MHC), a region of chromosomal DNA which plays a key role in the immune system and influences diverse functions and diseases. The MHC contains multiple polymorphic and duplicated genes (Zhang et al., 1990). The method relies inter alia upon the presence of duplications which are imperfect. The ancestral haplotypes of the MHC extend from HLA B to HLA DR and have been conserved en bloc. These ancestral haplotypes and recombinants between any two of them account for about 73% of ancestral haplotypes in the caucasian population. Other multigene complexes containing ancestral haplotypes include the lipoprotein gene complex and the RCA complex.

The most common approach in species identification focuses on two regions of the mitochondrial genome, the D-loop and cytochrome B (Cyt-B) gene (Branicki et al., 2003). Due to the mutation rate of mitochondrial DNA, it is commonly used to examine species difference. As such, Cyt-B studies have demonstrated success for a wide array of species although problems such as variable amplification efficiencies and an inability to differentiate between closely related species have been observed in some cases. In general, the approach relies on sequencing and subsequent sequence comparison against an available genetic database to identify the origin of the sample. Other methods include the analysis of nuclear targets such as beta actin, 28sRNA and TP53 genes, as well as the use of Short Tandem Repeats and Rapid Amplification of Polymorphic DNA. Regardless, there is a need for efficient methods for the identification of species using genetic analysis.

Large datasets are being created in fields as diverse as atmospherics, population ecology, forensics, particle physics, fluid mechanics, genomics and proteomics. Because of their size, the analysis of internal structure and patterns within large datasets requires substantial computer power. For example, in evolutionary genomics where structural patterns are compared between different species, the data strings are sequences of DNA in the order of 2-3 gigabases, hence the number of possible permutations comparing only small sequence sets is immense, and comparing large sequence sets is beyond all but the world's most powerful computers. In order to reduce the run time of analysis, options being developed include constructing larger computers such as massive parallel arrays or smaller processors in large clusters, which adds cost and an increased amount of hardware.

There is a need for further methods of genetic analysis which can be used to produce a profile which provides information regarding genomic DNA in a test sample. Here we describe a particular form of genetic analysis relying on the amplification of complementary duplicons. The present invention also seeks to provide a method of comparing large datasets, such as sequences of genomic DNA for the purposes of ascertaining duplication between portions of the compared sequences in a simpler and cost-effective manner than previously performed.

SUMMARY OF THE INVENTION

The present invention stems from the characterisation of DNA corresponding to ancestral haplotypes. Analysis of the major products resulting from nucleic acid amplification of particular duplicated sequences found that the intermediate sequences flanked by the duplicated sequences provided valuable information regarding the genome. More specifically, amplification resulted in distinctive profiles. These profiles can be used in methods of genetic analysis of genomic DNA to generate information about a test sample.

Accordingly, in a first aspect the present invention provides a method of genetic analysis, the method comprising amplifying a complementary duplicon(s) in genomic DNA in a sample from an individual and generating a profile of the amplification products, wherein the profile is characteristic of the genome.

The amplification products have sequences that are relevant to function and also provide a historical record of integration, insertion, deletion, duplication and other alterations to DNA structure and content. The method according to the first aspect of the invention may be used to generate a profile which can be used to, for example, determine the species of organism from which the sample is derived, examine past changes to the genome of a species or an individual thereof, or to predict future susceptibility to disease.

Unexpectedly, in many instances it has been found that the profiles were largely species specific. Furthermore, the products of amplification of complementary duplicons are more informative than known alternatives for determining the species from which a sample comprising genomic DNA is derived which tend to differ to only minor degrees. This advantage of the methods according to the present invention may be explained in part by the fact that the amplified complementary duplicon products are mixtures due to amplification of sequences differing in length and content, differential priming due to minor differences between priming sequences and competition between the amplicons and interaction between the products including concatamers.

Remarkably, in contrast to the products of U.S. Pat. No. 6,383,747 and other markers of individual identity and transplant matching, the substantial differences between species are not related to polymorphism within a species. For example, MHC sequences are polymorphic i.e. different between alleles and haplotypes within a species whereas many amplified complementary duplicon products are substantially or wholly monomorphic within a species. So as to avoid confusion, we continue to use the term polymorphism to refer to differences within a species recognizing that some alleles and haplotypes may be trans-species i.e. found in closely related (ancestral) species. By contrast, many of the amplified complementary duplicon products are monomorphic but interspecific which leads us to refer to such difference as interspecific monomorphisms (ISM).

Thus, in a preferred embodiment of the first aspect the profile is used to determine the species of the individual.

Furthermore, in a second aspect the present invention provides a method of genetic analysis, the method comprising
   i) obtaining a first nucleic acid sequence profile derived from amplification of a complementary duplicon(s) in genomic DNA in a sample from an individual,
   ii) comparing the first nucleic acid sequence profile with one or more reference nucleic acid sequence profiles obtained by the amplification of the complementary duplicon(s) from one of more known species, and
   iii) determining the species from which the sample is derived based on the similarity of the first nucleic acid sequence profile when compared to the reference nucleic acid sequence profiles.

Thus, a sample comprising genomic DNA may be isolated from an individual, or obtained from an unknown source (such as a hair follicle or blood), and then subjected to the characterisation as detailed above to assign species.

As can be seen in FIG. 4, the profiles generated using the amplification procedure are almost identical between four different human populations, namely Asian, negroid, Australian aboriginal and Caucasians. Furthermore, FIG. 6 shows each of the profiles generated using the same amplification procedure from (a) human, (b) chimp, and (c) orangutan are species specific (see also FIG. 6(d)). Thus, humans had a distinctive profile which was different from the equally distinctive profile of other primate species.

The amplified products can be considered as species specific markers which can be used in various methods of genetic analysis. Such uses of the methods of the first and second aspects include, but are not limited to, the following:
   (a) a method of determining the species of an unknown sample of DNA by comparing the profile to a library of reference samples (for example, in food authentication);
   (b) a method for the detection of the presence of, and quantifying the extent of, contaminating DNA;
   (c) a method for the definition of the species of mixed populations in the wild e.g. fish;
   (d) a method for classification of offspring including hybrids;
   (e) a method for estimation of divergence times between species when unknown or uncertain;
   (f) a method of determination of the species of cells including sperm, ova, stem cells, clones etc;
   (g) a method of comparison of RLEs and other complementary duplicons found in different populations, groups and species;
   (h) a method of estimating the potential for success in crossbreeding;
   (i) a method of evaluating the explanations for poor fertility and survival;
   (j) a method of investigating the success and failure of IVF.

In one embodiment, the individual is a hybrid of two species and the method determines the parent species of the hybrid.

In a further aspect, the present invention provides a method for detecting the presence of, and/or quantifying the extent of, contaminating DNA in a sample, the method comprising
   i) obtaining a first nucleic acid sequence profile derived from amplification of a complementary duplicon(s) in genomic DNA in a sample,
   ii) comparing the first nucleic acid sequence profile with one or more reference nucleic acid sequence profiles obtained by the amplification of the complementary duplicon(s) from one of more known species, iii) determining if the sample is derived from a single species based on the similarity of the first nucleic acid sequence profile when compared to the reference nucleic acid sequence profiles,
iv) if the sample comprises DNA from at least two different species, determining the two or more species from which the sample is derived based on the similarity of the first nucleic acid sequence profile when compared to the reference nucleic acid sequence profiles, and
v) optionally quantifying the relative concentration of the DNA from the two or more different species in the sample.

The magnitude of the differences of the profiles between species can be quantified and compared to known separation (divergence) times. More specifically, the method provides a measure of the evolutionary relationships between species. Thus, in a further aspect, the present invention provides a method of estimating the divergence times between two different species, breeds, cultivars or strains, the method comprising
i) obtaining a nucleic acid sequence profile derived from amplification of a complementary duplicon(s) in genomic DNA in a sample from an individual of each species, breed, cultivar or strain,
ii) comparing the range of sizes of the products of amplification to determine the evolutionary relationship of the two species, breeds, cultivars or strains.

For example, divergence times could be determined by analysing the number of differences in a profile obtained from two different species when using the same primer(s). The more differences in the profile, the greater the divergence times between the two species. Preferably, divergence times are determined by analysing a number of profiles obtained using various primers targeting a variety of complementary duplicons. This method is particularly useful for, but not limited to, analysing divergence times of closely related species. It is envisaged that this method can be combined with other known procedures for estimating divergence times to gain a better understanding of the evolutionary relationship of the species being analysed.

As the skilled addressee would be aware, although complementary duplicons have been found to be surprisingly conserved within a particular species, in some cases mutations which (for example) alter the size of an intermediate sequence flanked by complementary duplicons, or transposition of a mobile element, will result in the profile being slightly different between an individual and at least some other members of a species. When some degree of polymorphism is present in the putative or actual species or population, we use the designation interspecific oligomorphisms (ISO).

Complementary duplicons with some degree of interspecific oligomorphisms may be used to generate a profile useful for determining the breed, strain or cultivar of the individual.

Furthermore, complementary duplicons with some degree of interspecific oligomorphisms may be used to generate a profile useful for determining whether the individual possess a particular trait. Preferably, the trait is a disease or susceptibility thereto.

Miriami et al. (2003) describes the presence of complementary duplicons in some introns and proposes that these may relate to alternatively spliced introns. This may, in part, bear some relation to the present invention, in that some of the sequences flanked by complementary duplicons found according to the method of the first aspect of the invention may relate to alternatively spliced proteins.

In another example, some MHC haplotypes have differences in the number and location of interspersed retroviral-like elements (RLEs). These haplotypes may be linked to a disease, or susceptibility thereto, which can be detected using the methods of the invention.

As described above, genetic characterization and relationships may be defined by identifying duplicated and linked nucleotide sequences separated by an intermediate sequence. It has been determined that a single primer can be used for the methods of the invention in cases where the duplicons are complementary and reversed. This phenomenon was first observed when testing 5' and 3' primer pairs intended to amplify duplicated sequences of ancestral haplotypes. For example, when primer ATGAGCTTGTCTACACCT (SEQ ID NO: 1) was used under certain conditions involving low annealing temperature, it alone as a single primer amplified human DNA to produce a complex mixture of amplification products.

The principle of DNA amplification is based on a pair of primers, one forward and one reverse, which together permit exponential amplification of each and the intervening sequence. Furthermore, the annealing temperatures used with ATGAGCTTGTCTACACCT (SEQ ID NO: 1) were so low that specificity could not be expected implying that other factors, such as tertiary structure, contribute to binding. Finally, it is generally taught that amplification should result in one or, at most, a few products. Here, however, we produce a multitude of different products. Considering these factors it would have been predicted that the results using a single primer would be highly variable from run to run. In fact the results were highly reproducible. Accordingly, this result could not be predicted from the prior art.

Thus, in a particularly preferred embodiment of the invention the amplification is performed using a single primer. Furthermore, it is preferred that the method amplifies regions of the genome that comprise complementary duplicons that, on the same strand of DNA, have the reverse complement sequence (which may or may not have sequence variations but not so many variations that they cannot be recognised as repeats) (referred to herein as Bidirectional Amplification of Complementary Duplicons (BACD)).

In addition, a further aspect of the invention provides a method for amplifying DNA containing complementary duplicons comprising contacting the DNA with a single primer capable of hybridising to a complementary duplicon under conditions suitable for amplification.

Examples of single primers useful for the methods of the invention include, but are not limited to, ATGAGCTTGTCTACACCT (SEQ ID NO: 1), GGCACAATCGGTCCTACCAGAGCTA (SEQ ID NO: 2), GAGATCGAGACCATCCTGGCTAACAA (SEQ ID NO: 3), and CCGTGTTAGCCAGGATGGTCTCGAT (SEQ ID NO: 8), a primer comprising a sequence which is the reverse complement of any one thereof, or a variant of any one thereof which hybridizes under amplification conditions to the same complementary duplicon. In a preferred embodiment, the primer is ATGAGCTTGTCTACACCT (SEQ ID NO: 1), a primer comprising the reverse complement thereof, or a variant thereof which hybridizes under amplification conditions to the same complementary duplicon.

In a preferred embodiment, the complementary duplicons are interspersed transposons. Preferably, the interspersed transposons are retroviral-like transposons. In a further preferred embodiment, the retroviral-like transposons are Alu elements.

Amplification involves the use of amplification primers under certain conditions. The primer(s) used in amplification is/are designed to be substantially complementary to the duplicated sequences within the genome. They are designed to locate and characterise certain sequences flanked by complementary duplicons which are present within the genome.

Amplification may be carried out according to any method which results in amplification of sequences found between the primer binding sites. A preferred method is the Polymerase Chain Reaction (PCR), and a method derived therefrom which only requires a single primer.

The amplification step is preferably carried out under low to medium stringency conditions, i.e. with annealing conditions characterized by 40° to 46° C., preferably about 43° C. The amplification conditions are designed to allow for annealing and primer extension so that amplification occurs and are dependant, amongst other things, upon the sequence and length of the primer, and the DNA sample.

Preferably, the amplification products are separated by size exclusion chromatography. More preferably, the size exclusion chromatography is either agarose gel electrophoresis or polyacrylamide gel electrophoresis. Even more preferably, the size exclusion chromatography is polyacrylamide gel electrophoresis.

As would be appreciated by the skilled addressee, amplified complementary duplicons can be further characterized by DNA sequencing.

The present invention is directed to genetic analysis of the genomes of eukaryotes such as animals (such as mammals and insects) and plants. Preferred insects are mosquitoes. Preferred mammals are humans, livestock animals, companion animals and wild animals. More preferably, the mammal is a primate, more preferably a human.

In another preferred embodiment, the eukaryote is not a plant.

The present invention also provides means of comparing sequences in genomic DNA which can be used to identify primers useful in the methods of invention.

According to a further aspect of the invention, there is provided a method of identifying one or more subsets of elements in at least one set of elements, such that the one or more subsets match a subset of interest (SOI) to a predefined level of congruency, the method comprising the steps of:
forming an N-dimensional matrix of elements, wherein a transform of a subset of the one or more subsets is represented by a dimension of the matrix;
storing an identifier at each position in the matrix, each identifier representing a subset transform; and
finding at least one pair of matching identifiers in the matrix.

In another aspect, the invention provides an N-dimensional matrix of elements for use in identifying one or more subsets of elements in at least one set of elements, such that the one or more subsets match a subset of interest (SOI) to a predefined level of congruency, the matrix comprising:
an identifier at each position in the matrix, each identifier representing a subset transform;
wherein a transform of a subset of the one or more subsets is represented by a dimension of the matrix and at least one pair of matching identifiers in the matrix are found.

In another aspect, the invention provides a method of identifying one or more subsets each having elements that substantially match elements in a subset of interest (SOI), each of the subsets forming part of a set of elements or sets of elements, the method comprising the steps of:
forming a matrix including a list or partial list of each element in the set or sets, the position in the set or sets of each element and at least one offset indicating the position of another of the same element in the set or sets;

selecting the position of an element in the SOI;
identifying one or more of the offsets for the selected element and for adjacent elements to the selected element in the selected SOI,
finding matching elements in the set or sets of elements to the elements in the selected SOI based on the offsets.

According to another aspect of the invention, there is provided a matrix for use in identifying one or more subsets each having elements that substantially match elements in a subset of interest (SOI), each of the subsets forming part of a set of elements or sets of elements, the matrix comprising:
a list or partial list of each element in the set or sets;
the position in the set or sets of each element; and
at least one offset indicating the position of another of the same element in the set or sets;
wherein the position of an element in the SOI is selected, one or more offsets for the selected element and for adjacent elements to the selected element in the selected SOI are identified and thereafter the matrix is used to find matching elements in the set or sets of elements to the elements in the selected SOI based on the offsets.

In another aspect of the invention, there is provided a method of identifying one or more subsets of elements such that at least one element in the one or more subsets of elements is located in a selected subset of interest (SOI), each of the one or more subsets of elements and the selected SOI forming part of at least one set of elements, the method comprising the steps of:
determining an identifier for the SOI;
determining an identifier for each of the one or more subsets of elements; and
comparing each identifier of the one or more subsets to the SOI identifier in order to find elements in any of the one or more subsets that are also in the SOI which occurs when the compared identifiers are identical.

Upon the identification of complementary duplicated sequences using a method of the invention a primer, or set of primers, can be designed to amplify the complementary duplicon. These primers can be tested on genomic DNA, or in silico analysis performed, to determine whether the primer(s) is useful in the methods of genetic analysis described herein.

In a further aspect, the present invention provides an oligonucleotide primer for use in amplifying a complementary duplicon.

Also provided is an oligonucleotide produced using a method of the invention, wherein the primer can be used to generate a profile of the amplification products characteristic of a genome of an animal.

Preferably, the oligonucleotide primer is selected from the group consisting of:
a) an oligonucleotide comprising a sequence selected from the group consisting of: ATGAGCTTGTCTACACCT (SEQ ID NO: 1), GGCACAATCGGTCCTACCAGAGCTA (SEQ ID NO: 2), GAGATCGAGACCATCCTGGCTAACAA (SEQ ID NO: 3) and CCGTGTTAGCCAGGATGGTCTCGAT (SEQ ID NO: 8),
b) an oligonucleotide comprising a sequence which is the reverse complement of any oligonucleotide provided in a), and
c) a variant of a) or b) which hybridizes under amplification conditions to the same complementary duplicon as a) or b).

In another aspect, the present invention provides a kit for amplifying a complementary duplicon, the kit comprising at least one primer which hybridizes to a complementary duplicon.

The kit may comprise any other components required for the amplification of complementary duplicons, and/or for the analysis of the amplification products. In one embodiment, the kit further comprises at least one other component selected from the group consisting of: a reaction mix, nucleotide precursors or a DNA polymerase.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1 shows annealing of a primer (SEQ ID NO: 1) to complementary duplicons according to a preferred embodiment of the present invention.

FIG. 2 shows a segment of genomic sequence showing single primer potentially binding to both complementary strands. The sequence shown is a 2400 bp segment of genomic sequence (AC089999) with an example of the single primer, ATGAGCTTGTCTACACCT (SEQ ID NO: 1), potentially binding to both complementary strands separated by a distance of 560 bp. The amplicon (the amplification product) contains two MIR segments in opposite orientation (designated C and +) as listed in the Repeat sequence summary table identified using:http://www.repeatmasker.org. '.' represent continuation of genomic sequence. RLEs and primer binding bases are shown in upper case. Portions of AC089999 shown provided as SEQ ID NO's 9 to 11 respectively (5'-3').

Figure 7:
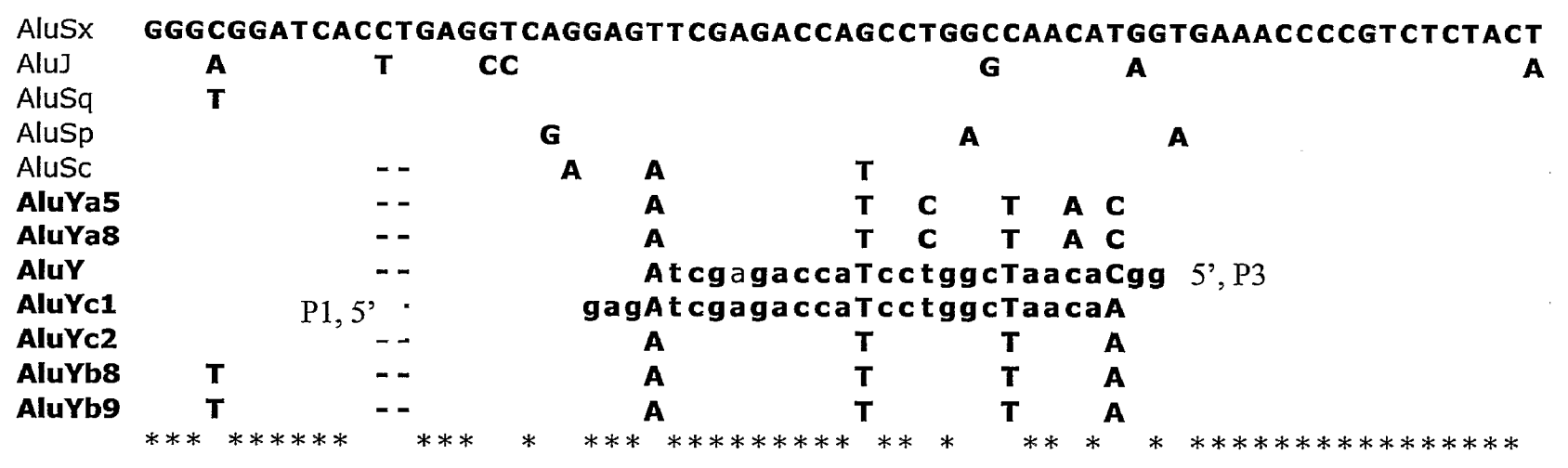

FIG. 7 provides an alignment of a region of different Alu repeats. The location of the binding sites of primers P3 (SEQ ID NO: 2) and P1 (SEQ ID NO: 3) are provided. The AluSx sequence has been designated SEQ ID NO: 12.

Figure 8A:
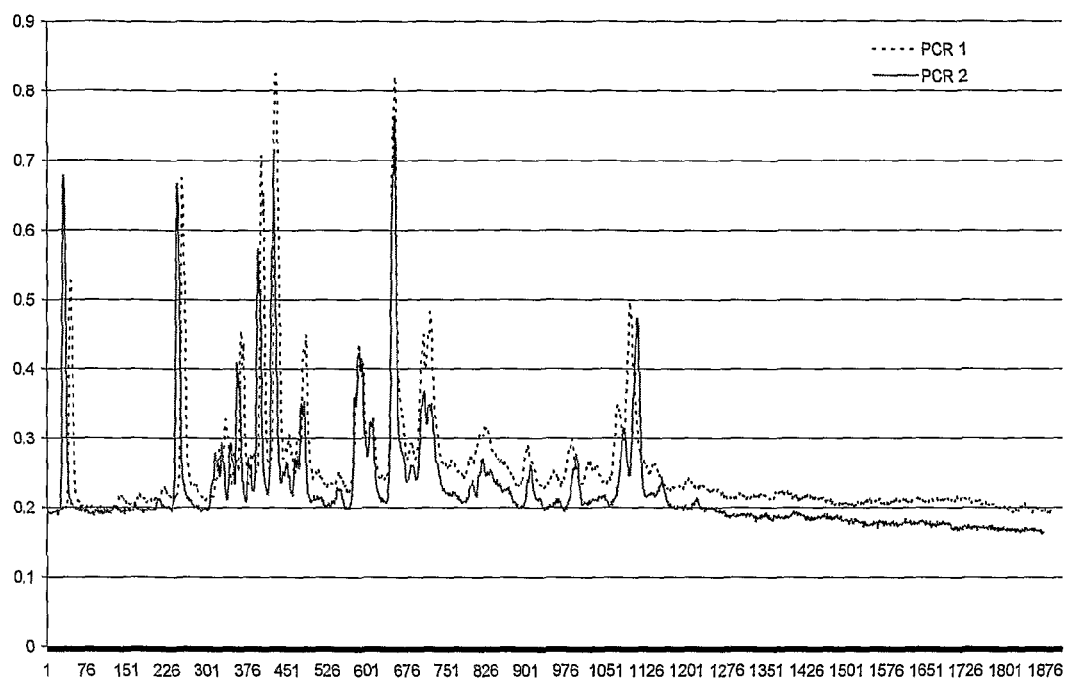
Figure 8B:
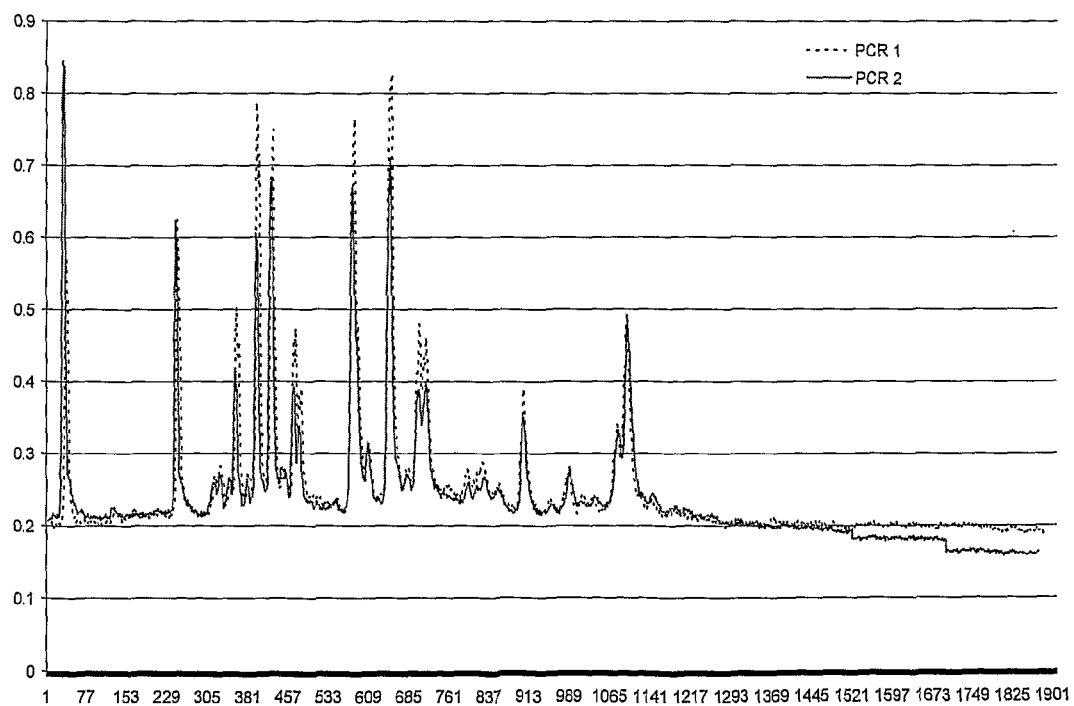
Figure 8C:
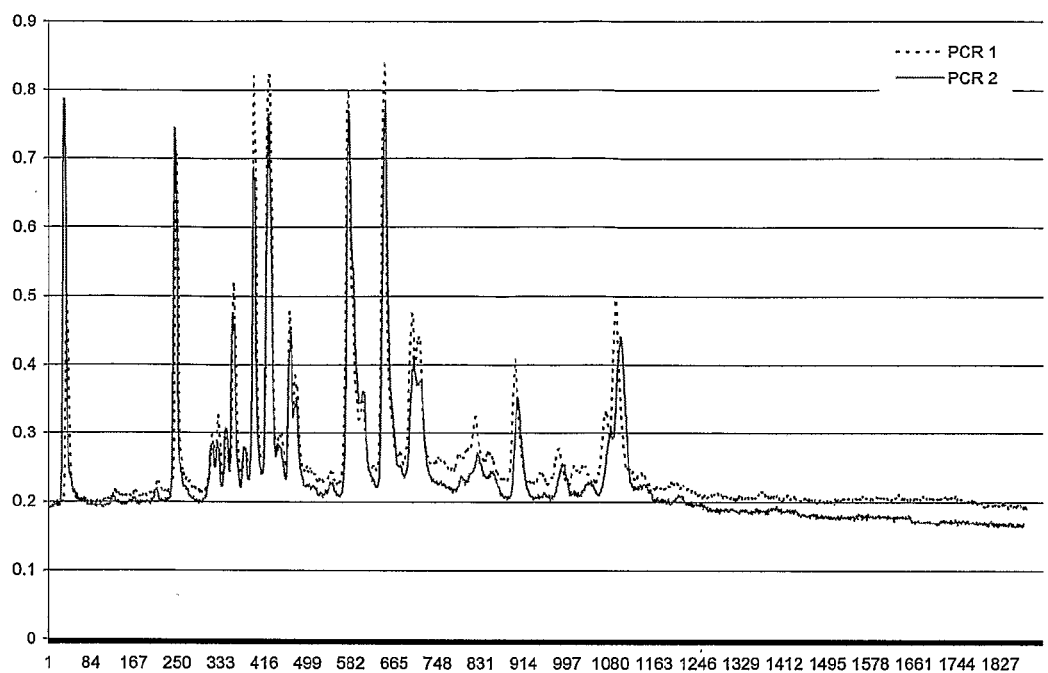
Figure 8D:
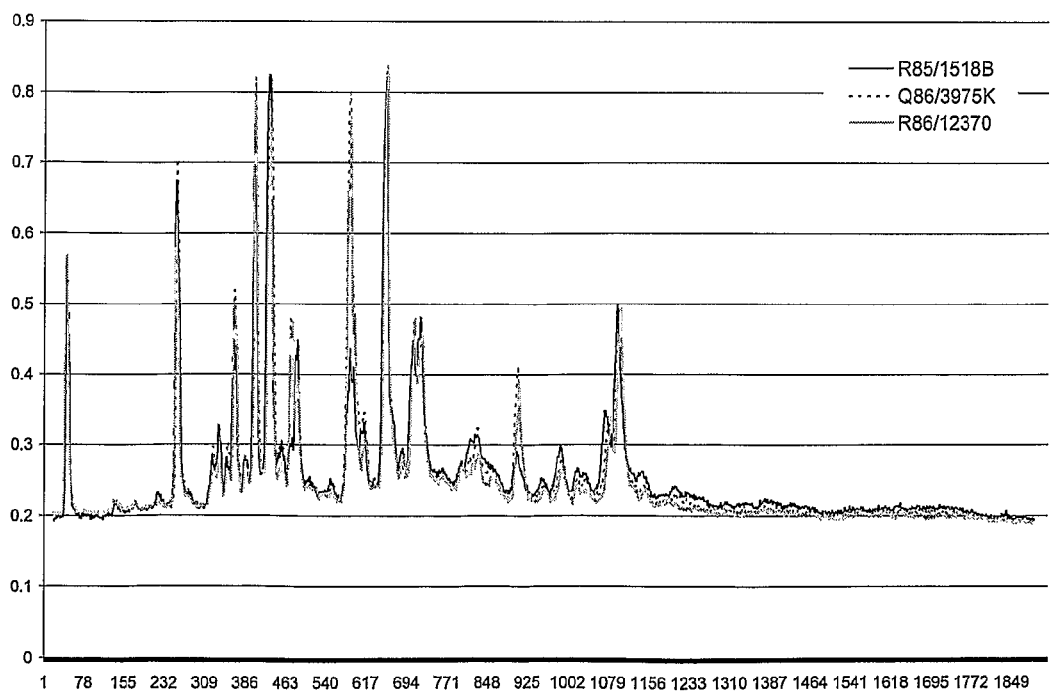

FIGS. 8a to 8c shows profiles obtained by amplification of DNA from different human samples using the P3 primer. In each case the results of two separate amplification reactions are provided. FIG. 8d provides an overlay of the profiles in FIGS. 8a to 8c.

Figure 9A:
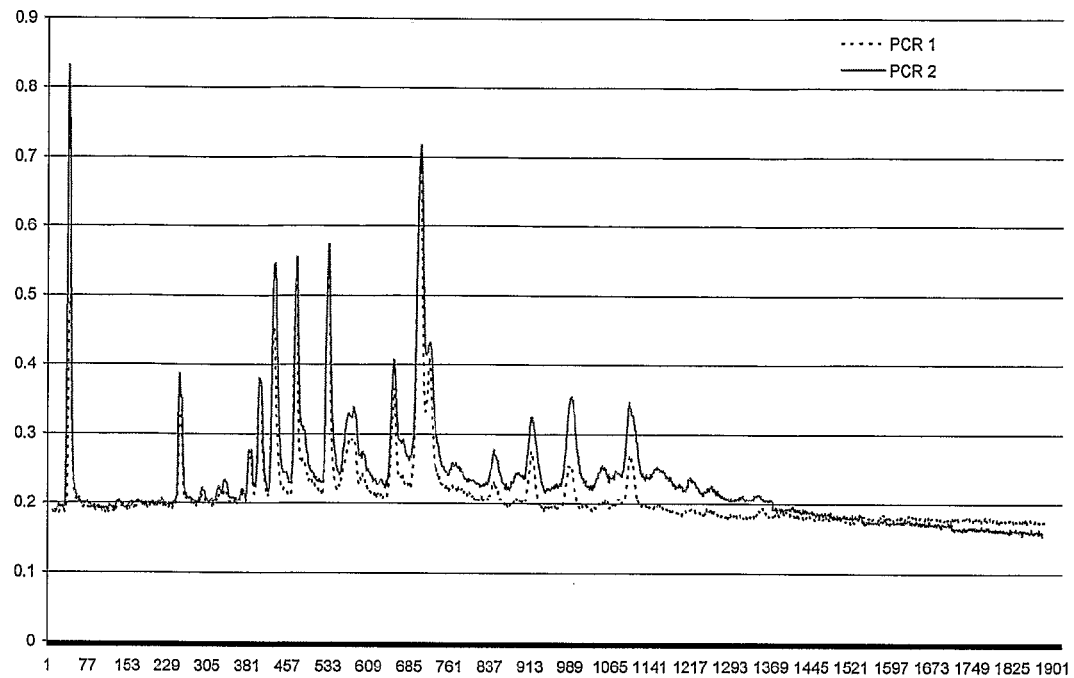
Figure 9B:
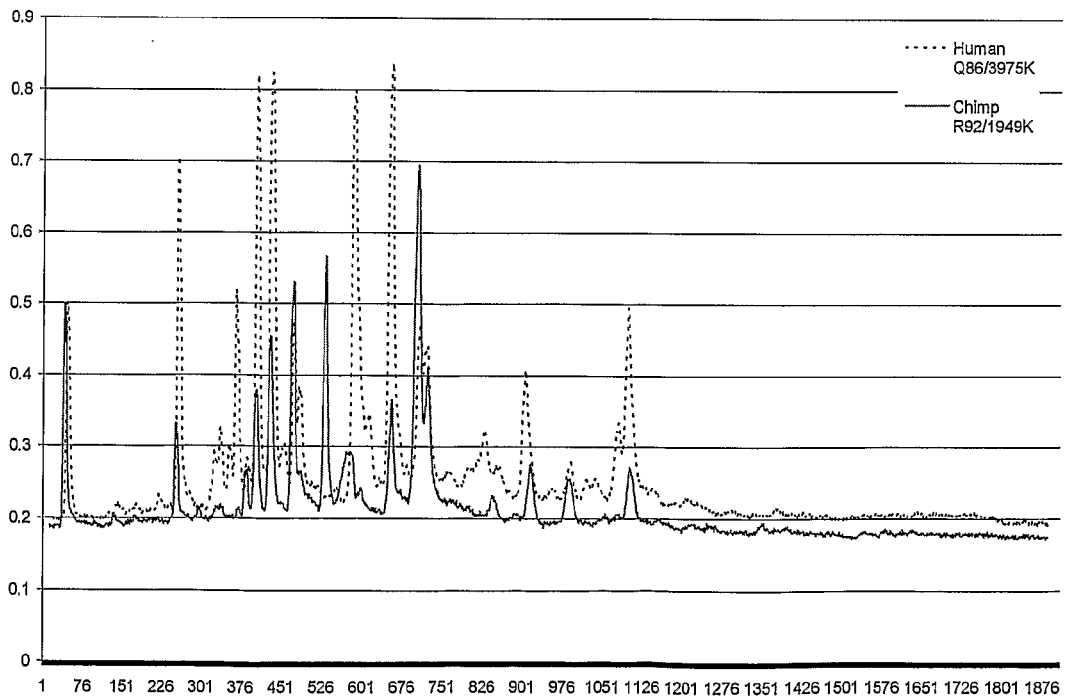

FIG. 9a shows profiles obtained by amplification of DNA from a chimp sample using the P3 primer. The results of two separate amplification reactions are provided. FIG. 9b provides a comparison of the profiles from a chimp (FIG. 9a) and a human (FIG. 8c).

Figure 10A:
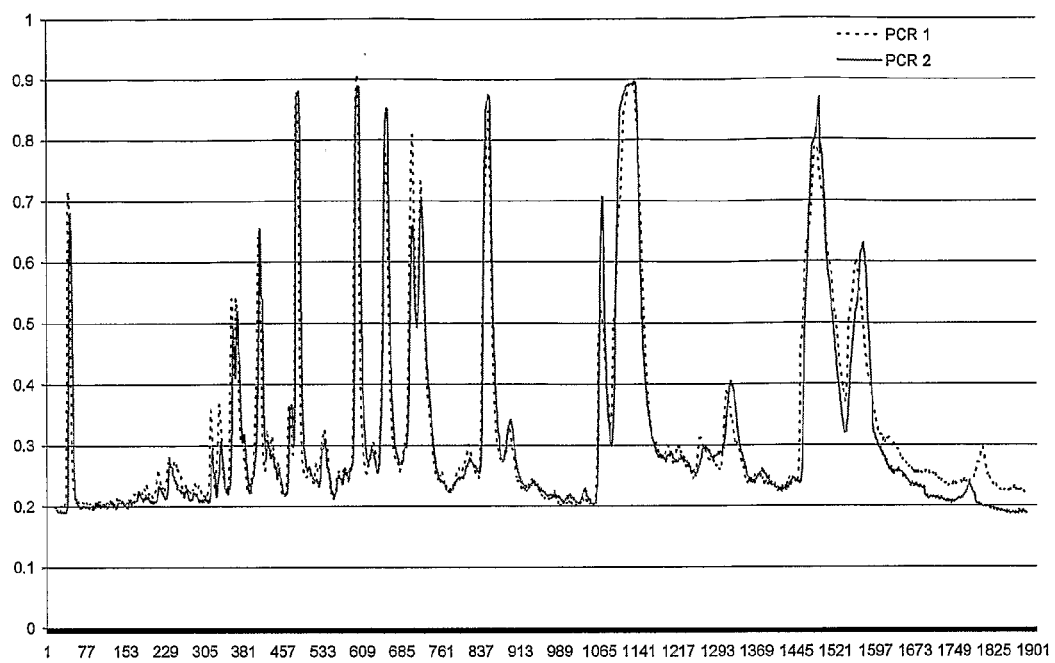

FIG. 10a shows profiles obtained by amplification of DNA from a cow sample using the P3 primer. The results of two separate amplification reactions are provided.

Figure 10B:
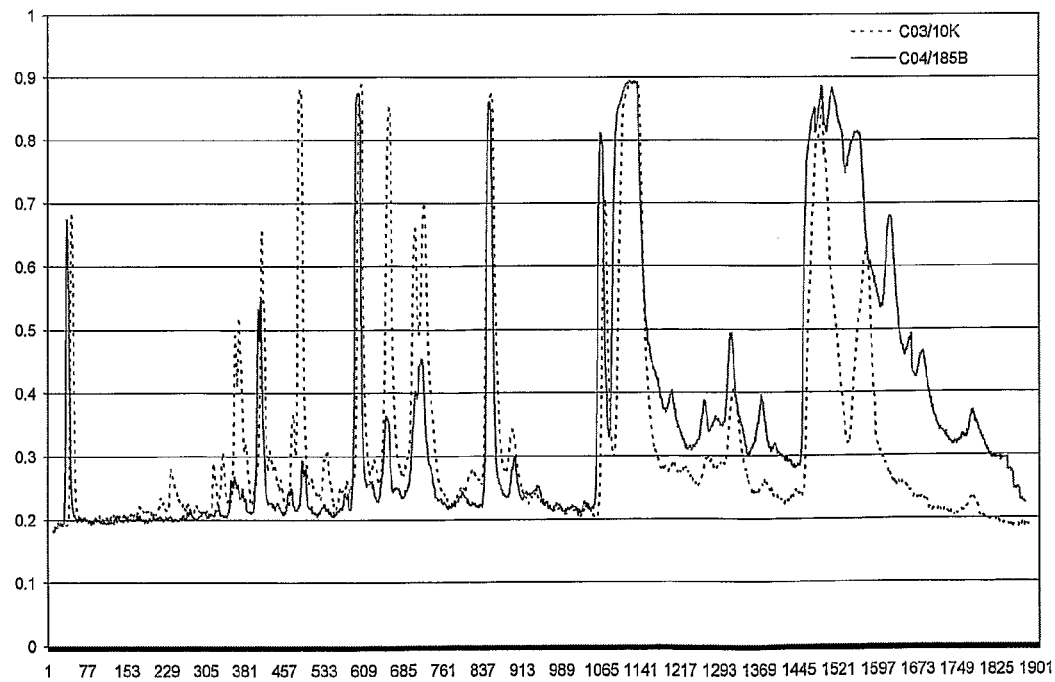

FIG. 10b provides an overlay of the profiles from two different cow using the P3 primer.

Figure 10C:
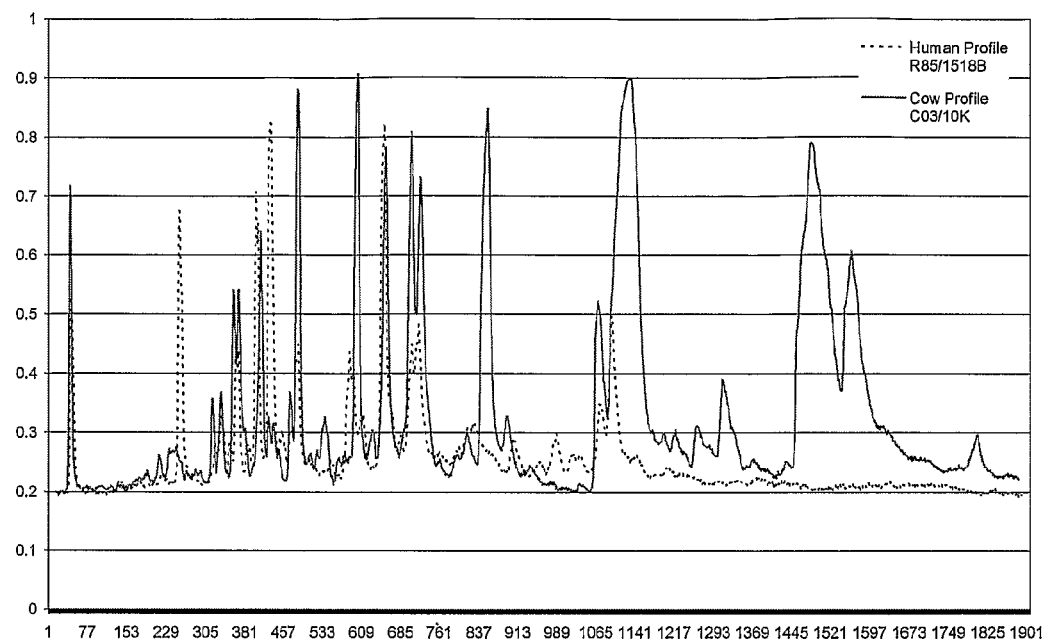

FIG. 10c provides a comparison of the profiles from a cow (FIG. 10a) and a human (FIG. 8a).

Figure 11A:
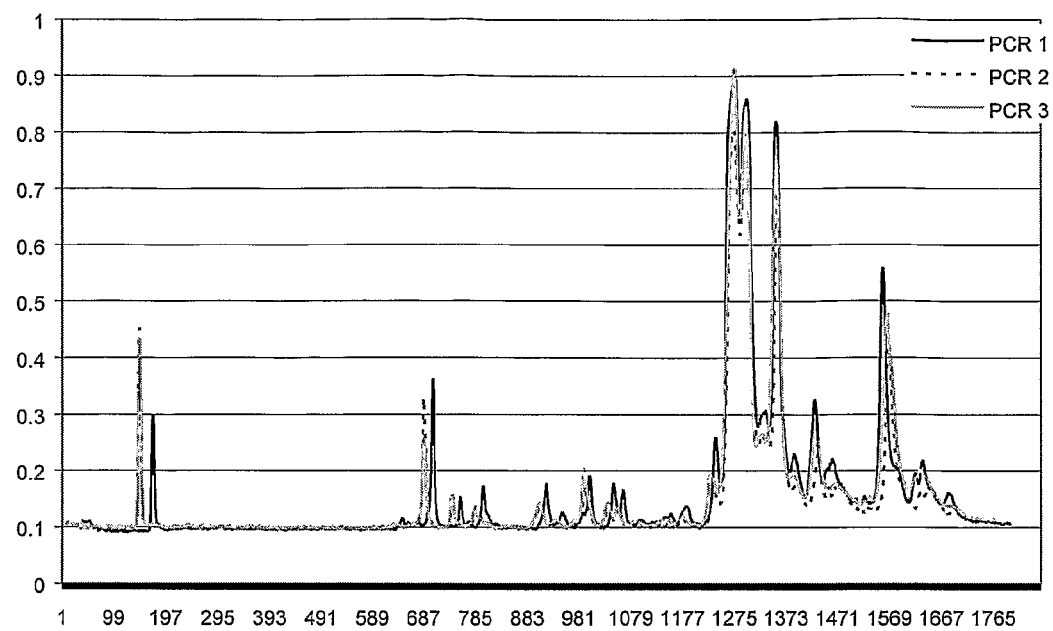
Figure 11B:
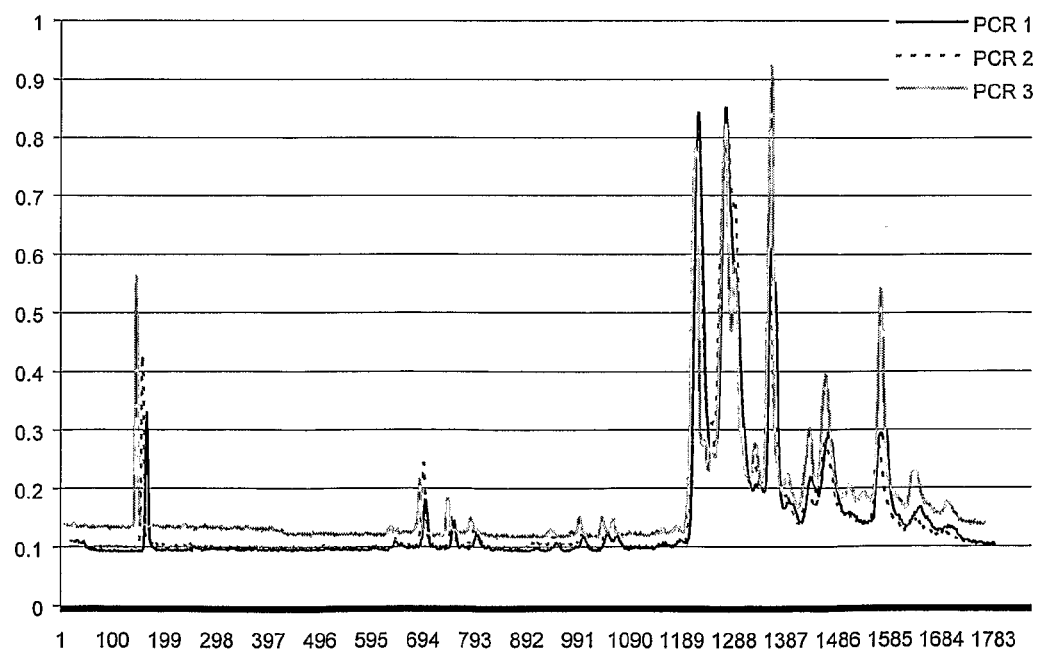
Figure 12A:
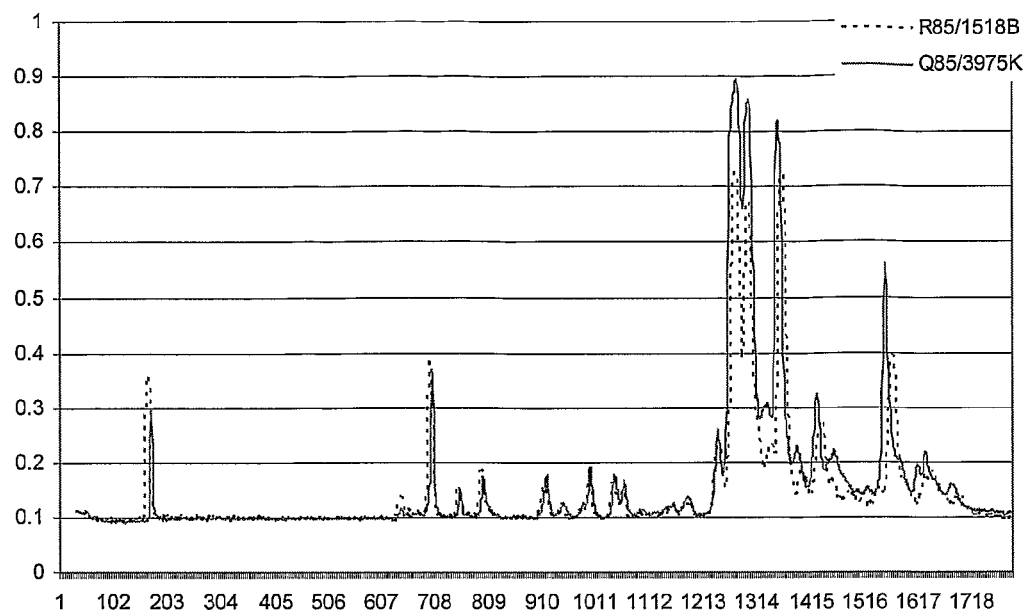
Figure 12B:
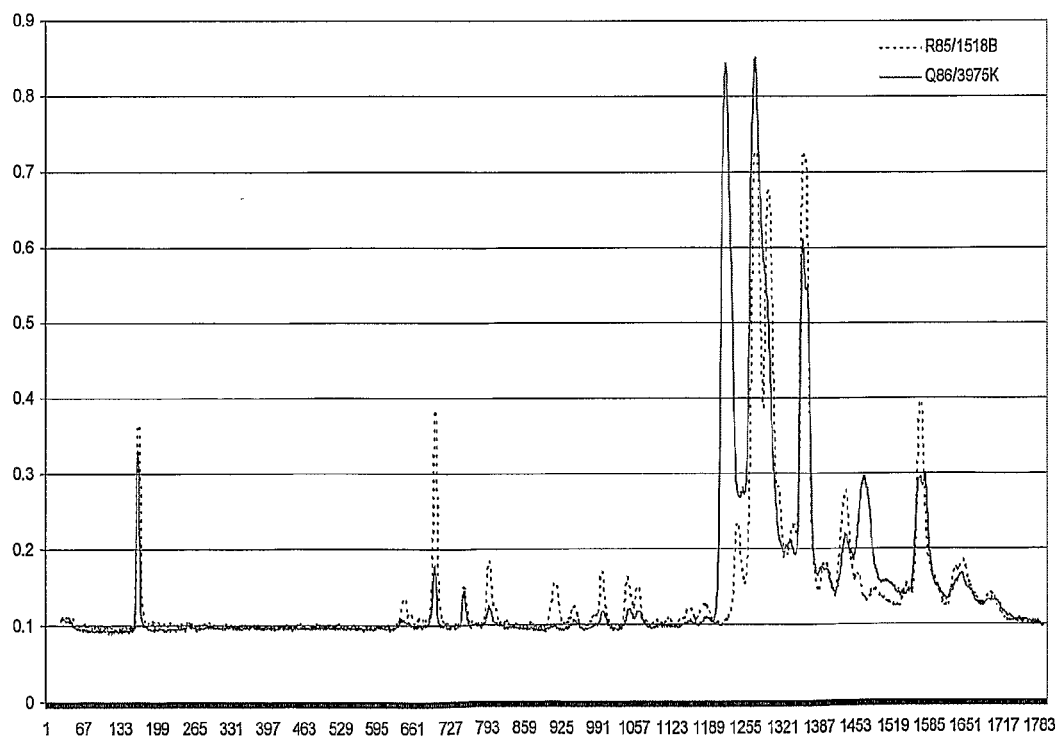
Figure 12C:
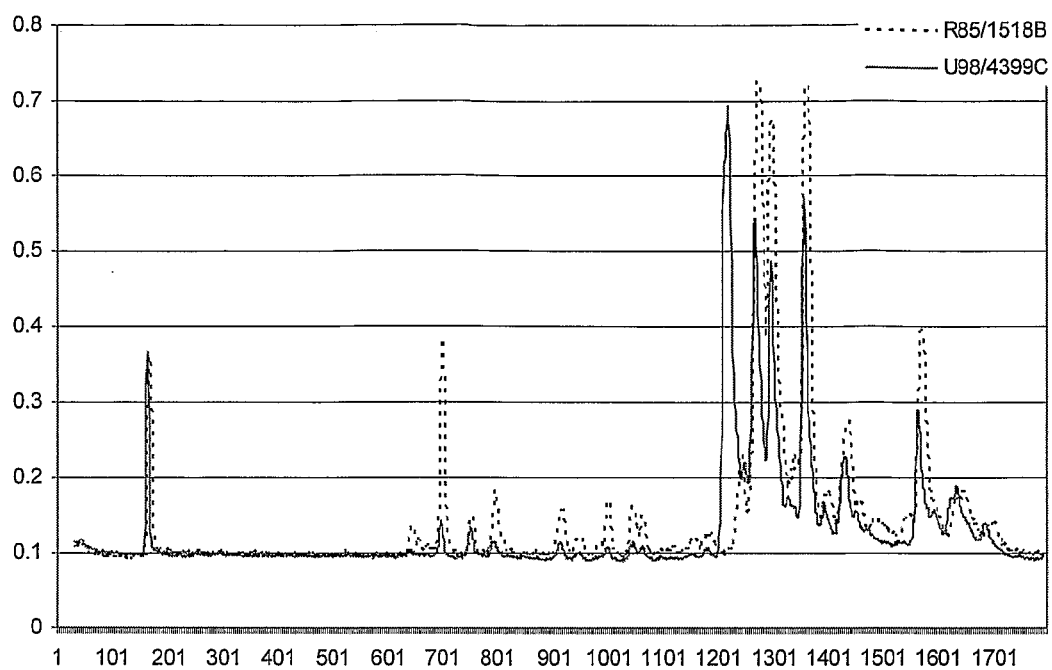
Figure 12D:
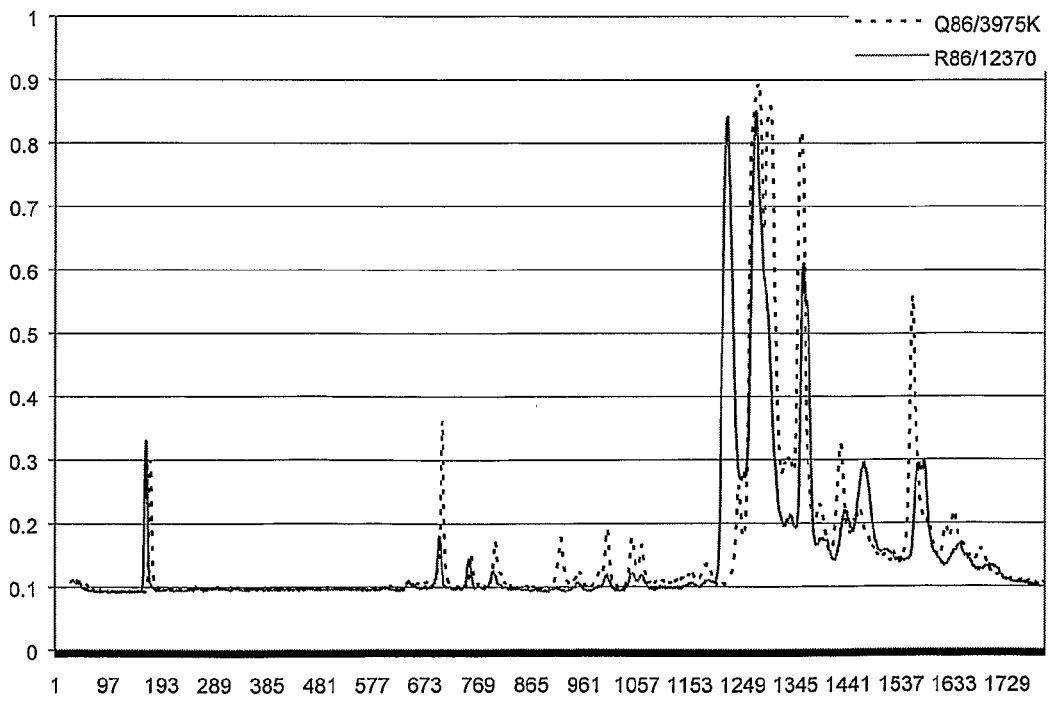
Figure 12E:
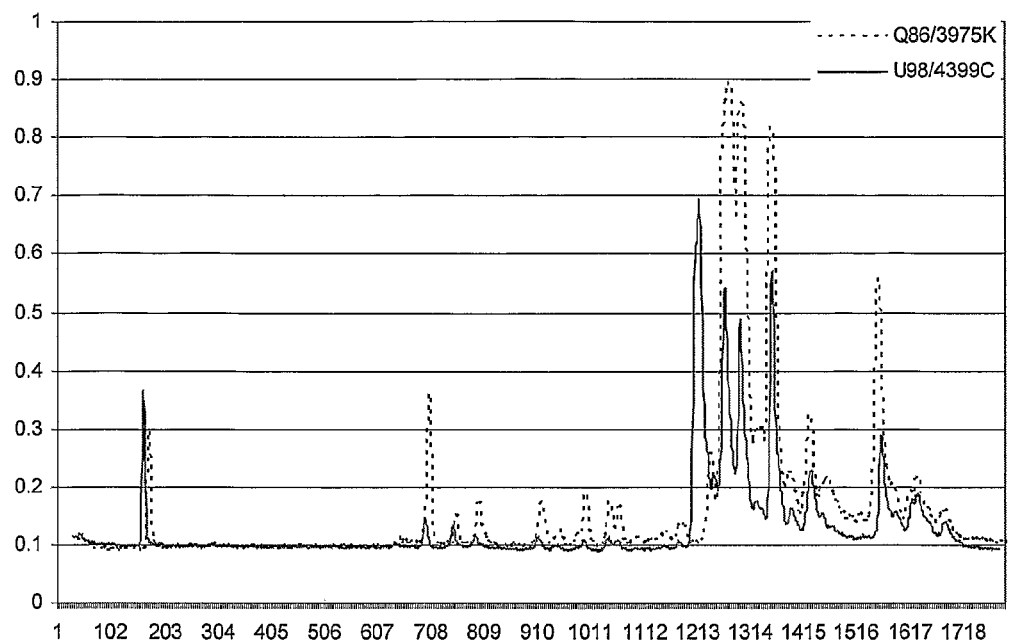
Figure 12F:
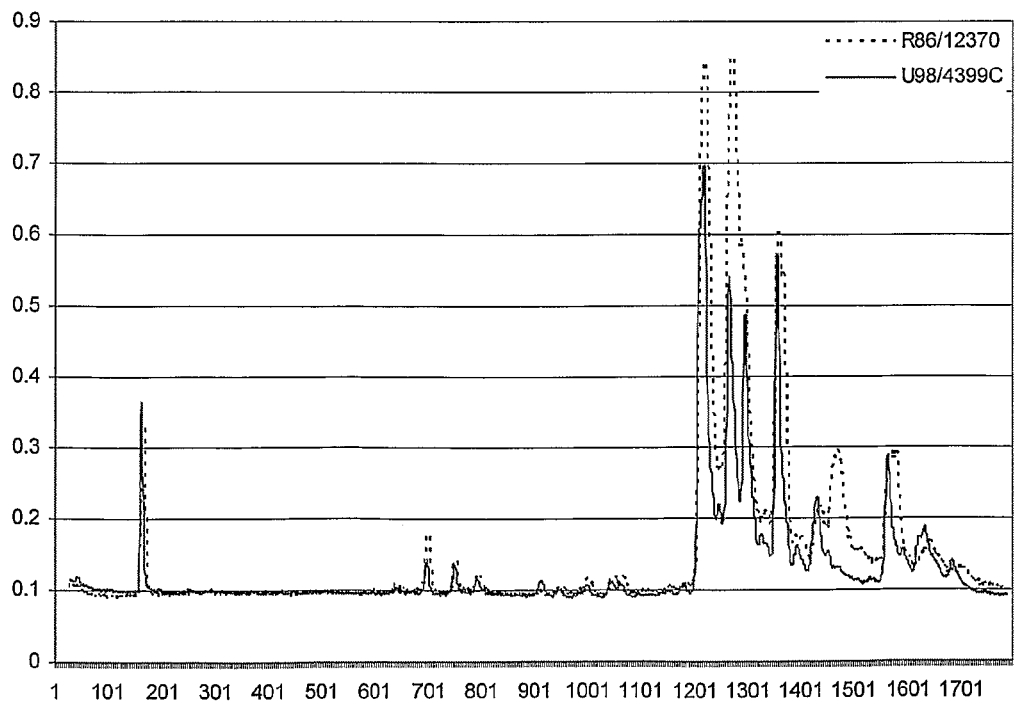

FIGS. 11a and 11b shows profiles obtained by amplification of DNA from different human samples using the P1 primer. In each case the results of three separate amplification reactions are provided.

FIG. 12a to 12f provides overlays comparing the profiles obtained by amplification of DNA from various human samples using the P1 primer.

Figure 13A:
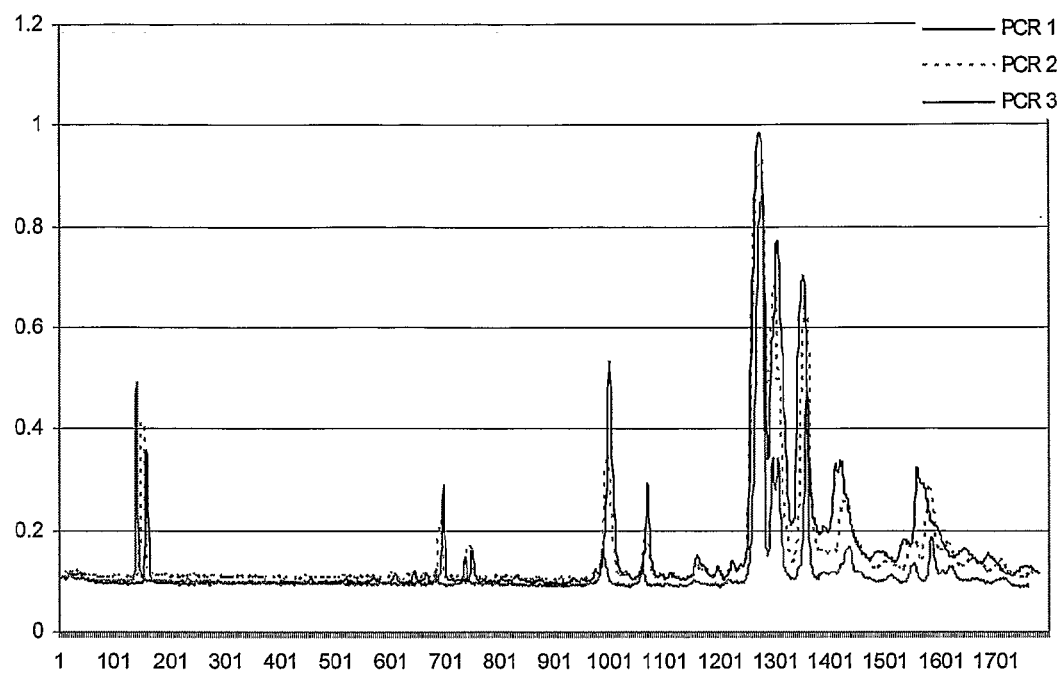
Figure 13B:
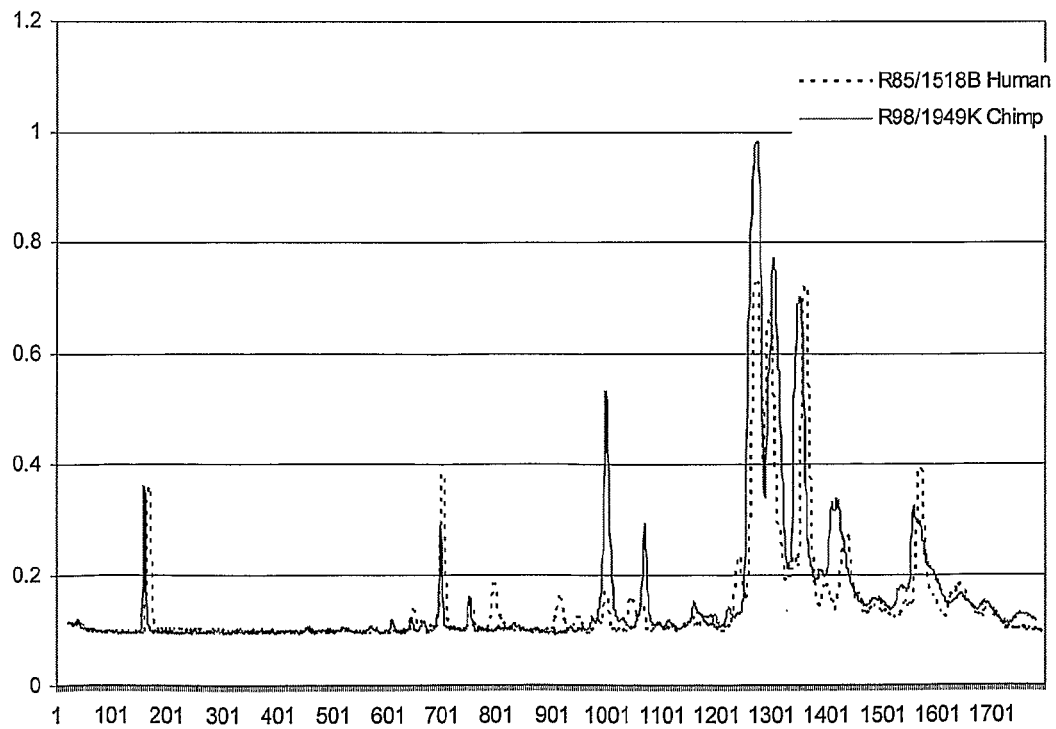
Figure 13C:
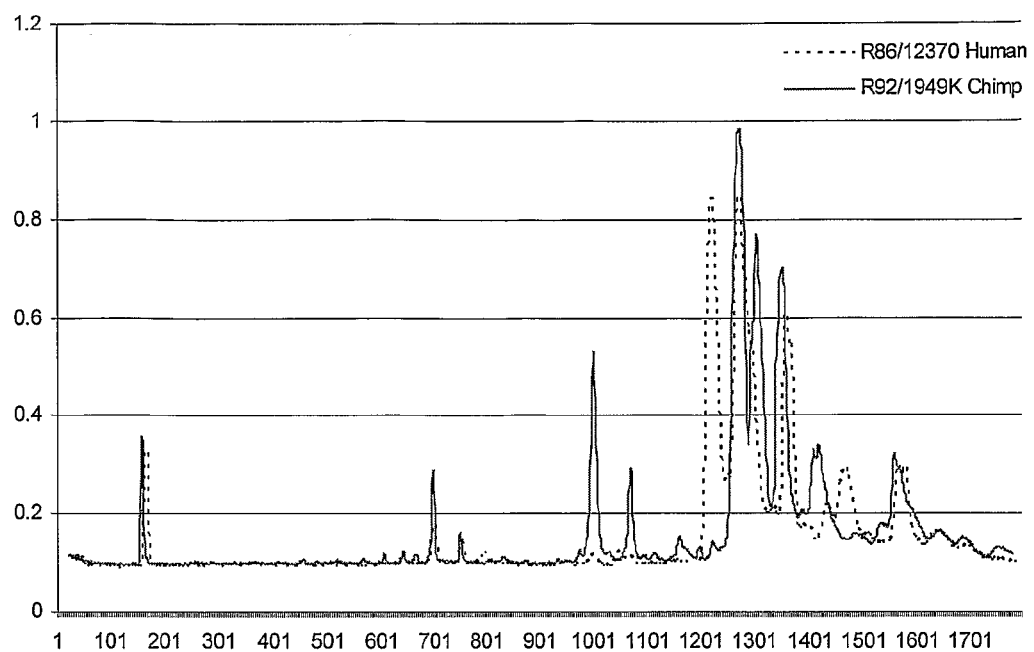
Figure 13D:
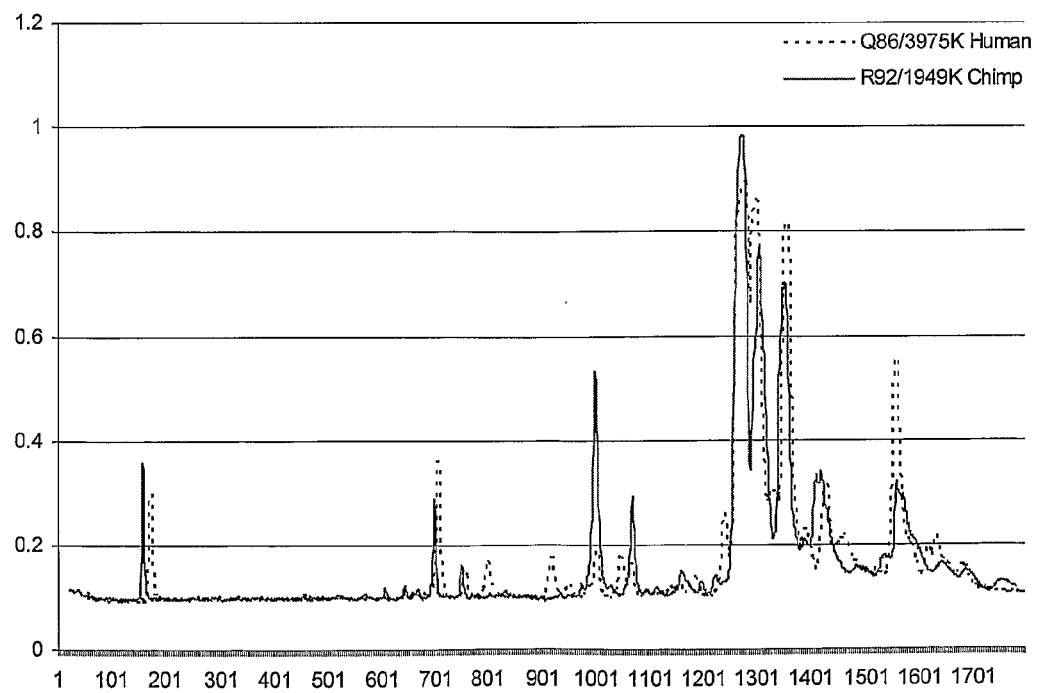
Figure 13E:
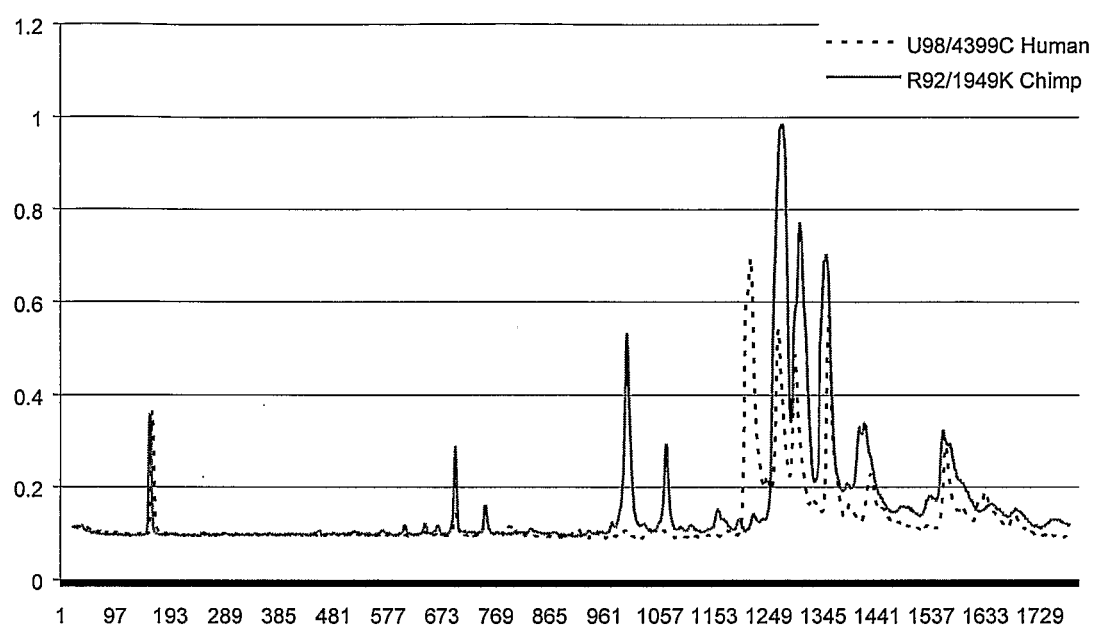

FIG. 13a shows profiles obtained by amplification of DNA from a chimp sample using the P1 primer. The results of three separate amplification reactions are provided.

FIGS. 13b to 13e provides overlays comparing the profiles obtained by amplification of DNA from various human samples using the P1 primer with the profiles obtained by amplification of DNA from various chimp samples using the same primer.

Figure 14:
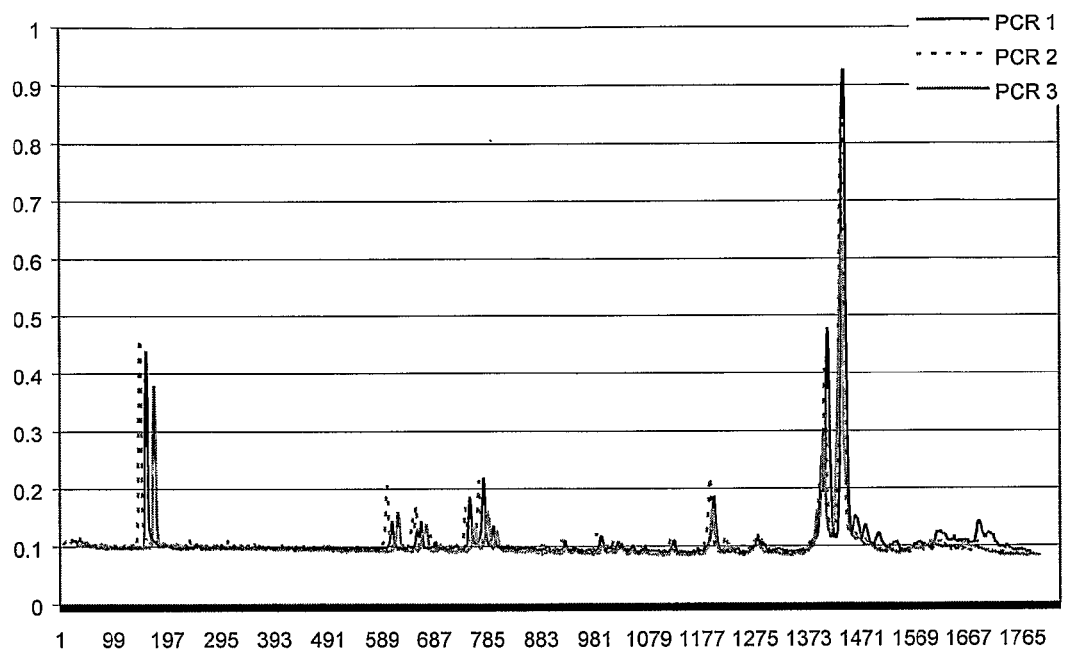

FIG. 14 shows profiles obtained by amplification of DNA from a cow sample using the P1 primer. The results of three separate amplification reactions are provided.

Figure 15B:
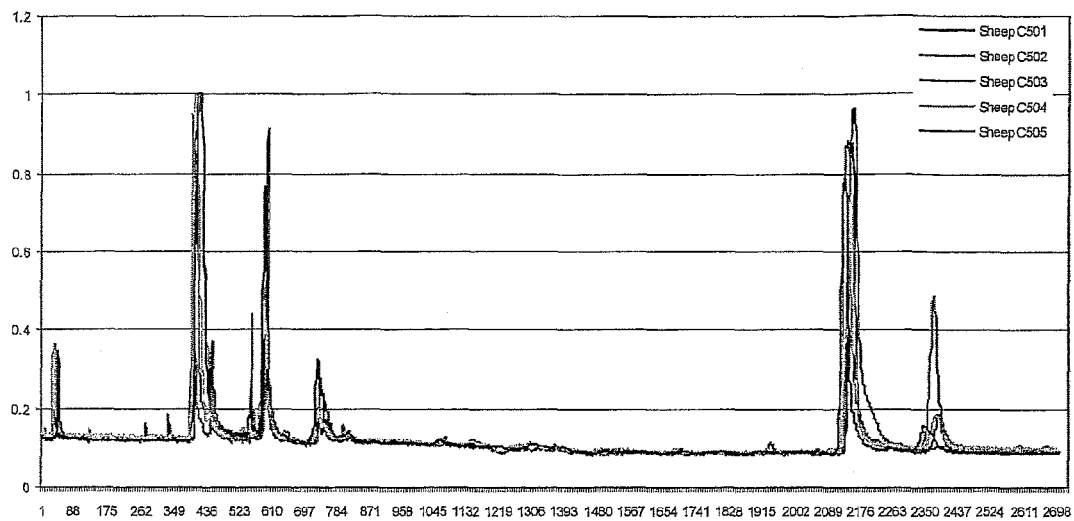

FIG. 15 shows profiles obtained by amplification of DNA from a horses, donkeys and sheep samples using the P3 primer. The results of separate amplification reactions on samples from different individuals are provided for each species.

FIG. 16 shows profiles obtained by amplification of DNA from cow samples using the P3 primer. The top panel shows profiles monomorphic between different individuals whereas the bottom panel provides some polymorphic profiles between individuals.

FIG. 17 shows profiles obtained by amplification of DNA from dog samples using the P3 primer. The top panel shows profiles monomorphic between different individuals (breeds) whereas the bottom panel provides some polymorphic profiles between individuals.

Figure 18:
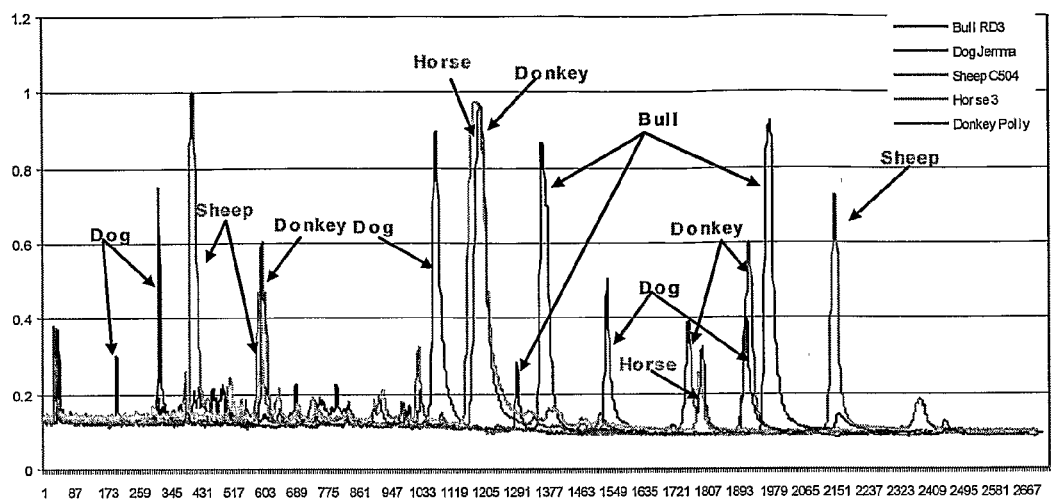

FIG. 18 provides a comparison between profiles obtained from cows, dogs, sheep, horse and donkey using the P3 primer and highlights species specific amplification products.

Figure 19:
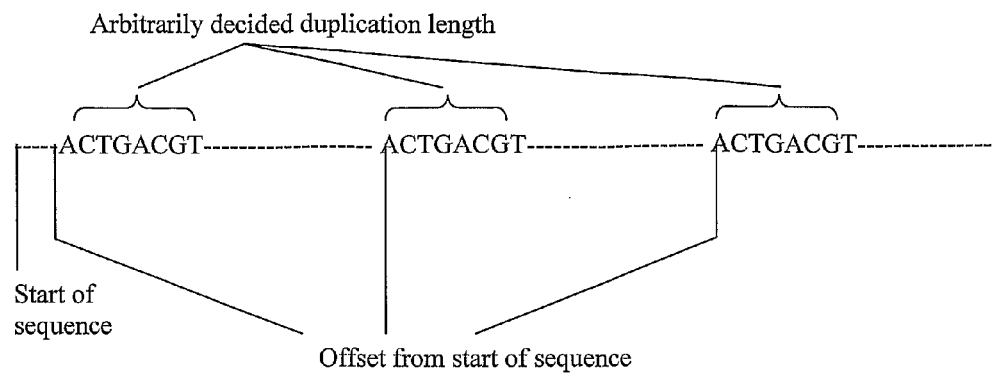
Figure 20:
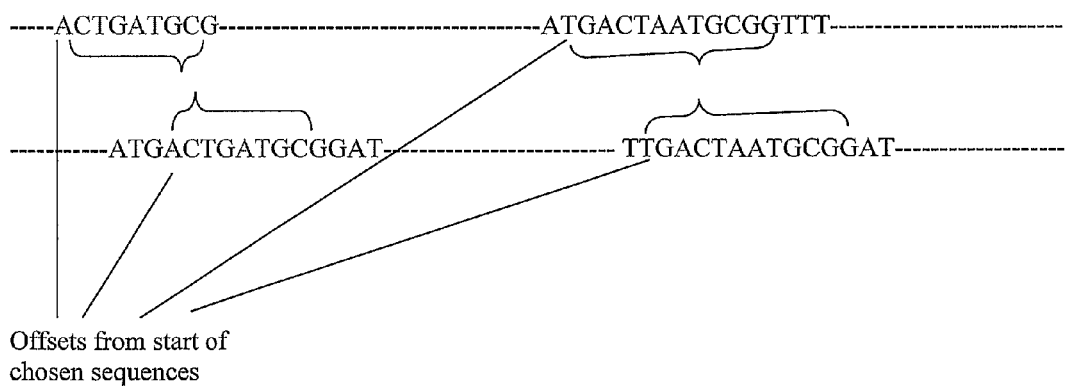
Figure 22:
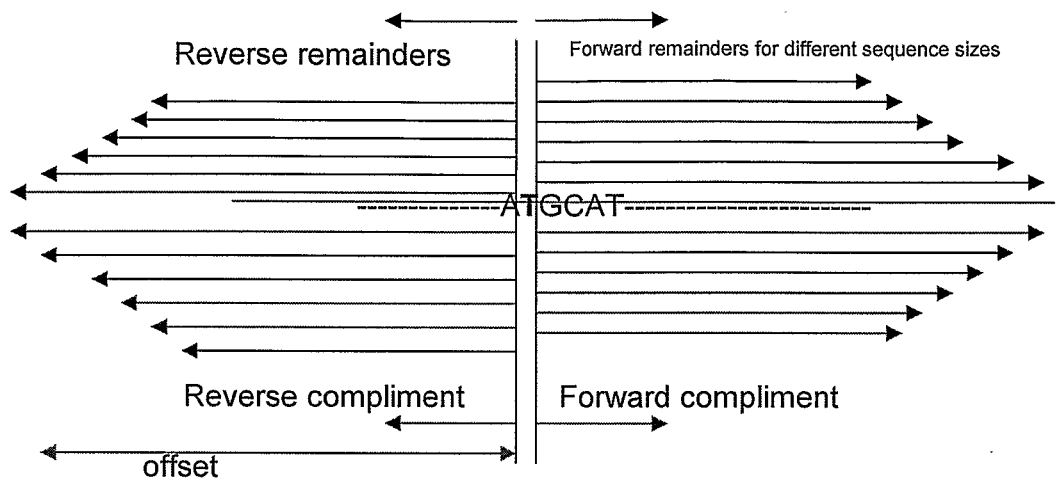

FIG. 19 shows duplicated subsets of elements, in the form of nucleotides, separated by an offset from the beginning of a set of elements;

FIG. 20 shows two pairs of duplicated subsets of elements, in the form of nucleotides, across two sets, and offset from one another;

FIG. 21 is a matrix showing offsets of two sets of elements at positions along each set and the relationship between the two sets;

FIG. 22 shows examples of remainders for various sized sets.

FIG. 23 is a matrix showing offsets to the next occurrence of particular nucleotides from a specified nucleotide position.

FIG. 24 is a matrix depicting remainder values for duplicant sizes of 5 to 10 against a sequence position and highlights an identical mismatch between a forward sequence of remainder values and a reverse compliment sequence of remainder values; and FIG. 25 is another matrix depicting remainder values for duplicant sizes of 5 to 10 against a sequence position and highlights a degree of fit between a forward sequence of remainder values and a reverse compliment sequence of remainder values.

KEY TO THE SEQUENCE LISTING

SEQ ID NO:'s 1 to 8, 17 to 27 and 35—Primers useful for amplifying complementary duplicons.

SEQ ID NO:'s 9-11—Portions of the human genome which form part of Genbank Accession No. AC089999 (see FIG. 2).

SEQ ID NO: 12—Portion of human AluSx repeat (see FIG. 7).

SEQ ID NO: 13—Human AluYc1 repeat (Genbank Accession No. AY520144).

SEQ ID NO:14—Portion of Gorilla AluYcl repeat (Genbank Accession No. AY520139).

SEQ ID NO: 15—Human AluSx repeat (part of Genbank Accession No. AF 134726).

SEQ ID NO:16—Human LINE (L1.2) repeat (Santos et al., 2000).

SEQ ID NO's:28 to 34—Primers described by Nelson et al. (1989).

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in molecular genetics).

Unless otherwise indicated, the recombinant nucleic acid techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors), and are incorporated herein by reference.

As used herein, the term "amplifying a complementary duplicon", or related terms, means that the amplification product typically comprises a portion of the two related duplicons and an intermediate sequence. More specifically, the primer(s) used in the methods of the invention hybridize to two related sequences on the same stretch of genomic DNA, and result in the amplification of the intervening sequence. As a result, the amplification product will most likely (the exception being when a primer hybridizes at the very end of the repeat unit) comprise a portion of the duplicated sequence at the 5' and 3' ends which flank the intermediate sequence.

As used herein, an "intermediate sequence" is a region of the genome that is flanked by complementary duplicons. Preferably, the intermediate sequence is less than about 5 kb, more preferably less than about 3 kb and even more preferably less than about 1.5 kb, to enable the amplified products of the complementary duplicons (wherein the amplified products comprise the intermediate sequence) to be analysed by, for example, gel electrophoresis.

As used herein, the "sample" can be any material comprising genomic DNA. The types of samples which can be tested varies depending upon the organism from which the sample is derived. For example, if the organism is a mammal the sample may be, but is not limited to, blood, plasma, saliva, skin cells buccal swab or hair follicles. If the organism is a plant the sample may be, but is not limited to, seeds, leaves, roots or pollen. If the organism is an insect the sample may be, but not limited to, legs, eggs or whole DNA extracts from larvae or adults. In some cases, DNA in the sample is at least partially purified using techniques well known in the art. However, as the skilled addressee would be aware, at least in some cases, such as a blood sample, it is not essential to purify the DNA before performing an amplification procedure.

The term "profile" refers to the presentation of information relating to the products obtained from the amplification step of the invention. The "profile" can be in any form that allows the amplification products obtained from two different individuals to be compared. Typically, the "profile" will be in the form of a graphic representation with one axis providing an indication of the size of the products and the other axis providing an indication of the quantity of the amplification products of a given size. Examples of such profiles are provided, but limited to, those in FIGS. 3 to 6 and 8 to 18.

As described herein, the profiles obtained from the amplification of various complementary duplicons has been shown to be species specific. This enables a panel of "reference nucleic acid sequence profiles" to be provided from a wide variety of organisms. When a sample of unknown origin is subjected to the methods of the invention the resulting profile can be compared to the reference panel and the species from which the sample derived determined.

In some cases, due to interspecific oligomorphisms, a primer(s) may be selected which can be used to amplify complementary duplicons that provide information regarding the breed, strain or cultivar of an individual. The term "breed, strain or cultivar" is used broadly herein to refer to any subgroup of a species of organism which have a common ancestry and possess features which distinguish one subgroup (sometimes referred to as subspecies) from other subgroups. For example, different cultivars of plants such as wheat are well known. Furthermore, different breeds of many animals such as dogs, cats, horses, sheep and cows are also well known.

In some other cases, due to interspecific oligomorphisms, a primer(s) may be selected which can be used to amplify complementary duplicons that provide information regarding a particular trait shared by some members of a species. There is no limitation on the potential types of traits which could be detected by the analysis of complementary duplicon as long as the trait has a defined genetic basis.

In some cases the complementary duplicon may be directly involved in the trait. In this regard, Alu repeats have previously been shown to be involved in some human diseases, or susceptibility thereto (Deininger and Batzer, 1999; Ricci et al., 2003; Sorek et al., 2002). In other cases, the complementary duplicon may merely be located in close proximity to the region of the genome responsible for the trait such that it can be considered as "linked" to the trait of interest. By "linked" (also referred to in the art as "genetically linked") it is meant that a marker locus comprising a complementary duplicon and a second locus are sufficiently close on a chromosome that they will be inherited together in more than 50% of meiosis, e.g., not randomly. Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM apart and most preferably about 0 cM apart.

The "trait" can be any characteristic of the organism with a defined genetic basis. In particular, the trait may be a disease or susceptibility thereto. Such diseases include, but are not limited to, cancer and autoimmune diseases. Examples of cancers include carcinomas, lymphomas, or sarcomas, such as, for example, ovarian cancer, colon cancer, breast cancer, pancreatic cancer, lung cancer, prostate cancer, urinary tract cancer, uterine cancer, acute lymphatic leukemia, Hodgkin's disease, small cell carcinoma of the lung, melanoma, neuroblastoma, glioma, and soft tissue sarcoma. In another embodiments the trait may be associated with athletic performance. The trait may also be linked to production qualities such as, but not limited to, wool production in sheep, milk production in diary cattle, meat quality in beef cattle, stamina in horses, diseases resistance in crop plants, salinity tolerance in crop plants, or starch content of the seeds of wheat plants.

As used herein, a "transposon" (also referred to in the art as "mobile genetic elements") is any genetic element capable of being moved from one region of the genome of an organism to another region of the genome. Transposons may be autonomous, namely the transposon comprises all the necessary machinery to cause transpositions (such as many LINEs of the human genome), or nonautonomous relying on factors not contained or encoded by the repeat unit for mobilization (such as Alu repeats).

As used herein, a "retroviral-like" transposon (also referred to as "retrotransposons", "retroviral-like elements" and "retroposons") are genetic elements which move via an RNA intermediate produced by the action of a reverse transcriptase (in the case of autonomous retroviral-like transposon the repeat unit encodes the reverse transcriptase).

As used herein, the term "interspersed" means that the repeat units are typically not tandemly repeated but generally found at a number of sites of the genome as a single unit.

Complementary Duplicons and Bidirectional Amplification of Complementary Duplicons Genetic characterisation and relationships may be defined by identifying duplicated and linked nucleotide sequences separated by an intermediate sequence. These duplicated and linked nucleotide sequences are termed complementary duplicons.

Following sequencing of the major products resulting from amplification of complementary duplicon sequences, unexpectedly it was discovered that the nucleotide sequences between the complementary duplicons were diverse, implying that the duplicons were closely linked but occurred at multiple and quite different sites within the genome. When the various sequences between the complementary duplicons were analysed by comparison with local and other available databases (including http://www.ncbi.nbm.nih.gov/, http://www.ddbj.nig.acjp/, and http://www.ebi.ac.uk) it was found that some of the sequences had particular properties. Some for example could be classified as retroviral-like elements (RLEs). Species specific RLEs such as Alu repeats provide an amplification target. However, other sequences were not classifiable as RLEs and could not be explained in this way. Table 1 shows the products (namely, a specific band selected and sequenced from the amplification products) observed after amplifying complementary duplicons in fish, mouse and human genomic DNA.

TABLE 1

| Product | Species Derived | Sequence Similarities |
|---|---|---|
| EL13 | Fish | Sequence matches part of the 28s RNA D2 domain, ITS1, ITS2 (spliced from pre-RNA to give mature RNA) Domain in NFkB-like protein mRNA - Ankyrin domain (protein-protein binding) Ig Heavy Chain variable region similarity. |

TABLE 1-continued

| Product | Species Derived | Sequence Similarities |
|---|---|---|
| EL21 | Fish | Similar to RIKEN gene. HS homologue is SRrp129 gene. Interacts with RNA Pol II and has Serine-Arg rich domains that are typical splice sites. I.e. Splicing factor. Transcribed sequence is similar to many 5'UTR regions within genes before poly A tail. Transcribed sequence is similar to Cytb Mit DNA in Shrews Transcribed sequence is similar to ITS1 in Claudonia rarenelil |
| M11 | Mouse | Alternatively spliced exons in SNURF-SNRPN mRNA. Transcribed sequence is similar to hox gene cluster Transcribed sequence similar to introns from myosin heavy chain (large ATPases) Sequence similarity to sequence upstream of the Ercc gene. |
| M13 | Mouse | Contains a common intronic repeat Transcribed sequence shows similarities to 16s RNA gene |
| H1 | Human | Contains a THE1 MalR Retroelement. Found in gene promoter regions. Part of the retroelement is in the disrupted in Schizophrenia gene |
| H2 | Human | Contains part of a common repeat element. Found in Envelope polyproteins |
| H3 | Human | Contains a MIR retroelement Sequence is similar to Dopamine D2 receptor (Alternatively spliced) |
| H4 | Human | Some similarity to aspartate beta hydroxylase (ASPH) (LOC57168), mRNA |
| H5 | Human | Some similarity to NKG2D, exon 10 |

The complementary duplicons need not be exact repeats but must merely be substantially repeated so as to be recognisable as repeats. For example, as shown in FIG. 1 the primer ATGAGCTTGTCTACACCT (SEQ ID NO: 1) has been determined to be able to hybridize to numerous portions of the human genome under the amplification conditions described in Example 1. In some cases the primer is able to hybridize both strands of human genome DNA at a spacing sufficient to produce numerous amplification products less than 1 kb in size. Whilst we have not been able to find evidence that the regions of the genome highlighted in FIG. 1 are repeats, or form a portion of a larger repetitive unit, these highlighted sequences can be considered as complementary duplicons.

Repeats may be judged by eye or using specific computer programs, for example "Repeat master"™ (see http://www.repeatmaster.org) or "Blast"™ (see http://www.ncbi.nim-.nih.gov/BLAST).

In a preferred embodiment, the complementary duplicons form defined repeat sequences interspersed throughout the genome. However, typically complementary duplicons are not tandemly repeated in the genome as in this case the amplification products will comprise monomeric repeats units with few, if any, products comprising an intermediate sequence.

With regard to the human genome, preferred complementary duplicons are Alu repeats. Alu repeats are a relatively recent acquisition of the human genome which are thought to be generally restricted to primates. However, surprisingly the present inventors have found that primers which bind human Alu repeats can also be used to amplify complementary duplicons in non-primate species. There are about $\sim 1 \times 10^6$ copies of Alu repeats in the primate genome, where waves of insertions of Alu repeats having been suggested to be correlated with major evolutionary branches. Alu repeats are inserted in various orientations, including reverse complement, and have been shown to affect gene expression (e.g. sequence, translation, transcription, alternative splicing, recombination, duplication depending on position) (Deininger and Batzer, 1999; Ricci et al., 2003; Sorek et al., 2002).

Furthermore, Alu repeats can be categorized into subfamilies (Batzer and Deininger, 2002; Kapitonov and Jurka, 1996; Antunez-de-Mayolo et al., 2002; Batzer et al., 1996a; Batzer et al., 1996b). It is likely that these subfamilies will provide information regarding ancestry within a species in a similar manner to the ancestral haplotypes described in U.S. Pat. No. 6,383,747. In addition, amplification of complementary duplicons of specific Alu repeats of a given subfamily may identify a link between a profile generated according to a method of the invention and a trait such as a disease trait.

Nelson et al. (1989) attempted to use a single primer designed from Alu repeats to analyse the human genome, however, only an uninformative smear of amplification products was obtained upon gel electrophoresis. Thus, Nelson et al. (1989) do not provide a profile of amplification products which is characteristic of the genome. In contrast, the present inventors have shown that a single primer designed from human Alu repeats can be useful in the analysis of the genome of humans, and other animal species. The failure of experiments of Nelson et al. (1989) seems to be linked to the use of a primer which hybridizes to a large number of Alu repeats, resulting in a very large number of amplification products. As a result, it is preferred that the methods of the invention, as they relate to primers which bind Alu repeats, utilize primers which are predicted to bind only a subset of Alu repeats of the genome. In a further preferred embodiment, the primer used in the methods of the invention is not AAGTCGCGGC-CGCTTGCAGTGAGCCGAGAT (SEQ ID NO:28), CGAC-CTCGAGATCTYRGCTCACTGCAA (SEQ ID NO:29), CCGAATTCGCCTCCCAAAGTGCTGGGATTACAG (SEQ ID NO:30), ACTCGGGAGGCTGAGGCAGG (SEQ ID NO:31), CTCGGCTCACTGCAAACTCC (SEQ ID NO:32), ATCGCATGAACCCGGGAGGC (SEQ ID NO:33), GCATCGATAGATYRYRCCAYTGCACT (SEQ ID NO:34) or the reverse complement thereof.

In one embodiment, the repeat unit (such as a subtype(s) of Alu repeats) that is amplified represents less than about 5% of the genome. In another embodiment, the repeat unit that is amplified represents less than about 3% of the genome. In another embodiment, the repeat unit that is amplified represents less than about 2% of the genome.

It has been determined that the oligonucleotides represented as SEQ ID NO: 2 and SEQ ID NO:3 at least amplify the AluY subfamily of human Alu repeats which represents about 1.5% of the human genome (Stenger et al., 2001). Thus, in another embodiment the repeat unit that is amplified represents about 1.5% of the genome. In addition, in another embodiment the method is at least is capable of amplifying AluY repeats of the human genome.

Typically, informative profiles produced using the methods of the invention have between 1 and about 50 peaks between 100 bp and 2,000 bp in length. This feature is a preferred embodiment of the invention. In another embodiment, profiles produced using the methods of the invention have between about 5 and about 50 peaks between 100 bp and 2,000 bp in length. In a further embodiment, profiles produced using the methods of the invention have between about 10 and about 50 peaks between 100 bp and 2,000 bp in length.

In addition, as outlined above, some MHC haplotypes have differences in the number and location of interspersed retroviral-like elements (RLEs) (see, for example, Kulski et al., 2001). These haplotypes may be linked to a disease, or susceptibility thereto, which can be detected using the methods of the invention. In a preferred embodiment, the disease is host vs graft or graft vs host disease. For example, where a profile is identified which is characteristic of a specific haplotype the methods of the invention can be used to match donor and recipient pairs for bone marrow transplantation.

In some cases "complementary duplicons" to be targeted in the methods of the invention are present in the same orientation on the same stretch of DNA. In this case, it is most likely two primers will be required for the amplification procedure. However, in other instances the duplicons are complementary and reversed. In this embodiment the amplification procedure is termed Bidirectional Amplification of Complementary Duplicons (BACD). BACD can be performed using a single primer or a pair of primers. In the latter case, the primers are designed such that the intermediate sequence is amplified and not just a portion of the repeat sequence.

In a particularly preferred embodiment, a single primer is used for BACD. When a single primer was used to amplify a BACD in genomic DNA from several species and the results compared to those obtained when other species markers were tested it was immediately obvious that the BACD products were far more diverse and informative than known alternatives which tend to differ to only minor degrees. This advantage of BACD may be explained in part by the fact that the BACD products are mixtures due to:

1. amplification of sequences differing in length and content;
2. differential priming due to minor differences between priming sequences and competition between the amplicons; and
3. interaction between the products including concatamers.

In these respects the profiles generated are similar to those described in U.S. Pat. No. 6,383,747.

Design of Primers for Amplification of Complementary Duplicons

The primers herein are selected to be "substantially" complementary to particular target DNA sequence. This means that the primers must be sufficiently complementary to anneal with their respective strands. Therefore, the primer sequence need not reflect the exact sequence of the template. For example, a non-complementary nucleotide fragment (i.e., containing a restriction site) may be attached to the 5' end of the primer, with the remainder of the primer sequence being complementary to the strand. Alternatively, non-complementary bases or longer sequences can be interspersed into the primer, provided that the primer sequence has sufficient complementarity with the sequence to anneal therewith and form the template for synthesis of the extension product.

Complementary duplicons may be judged by eye or using specific computer programs, for example "Repeat master"™ (see http://www.repeatmaster.org), "Blast"™ (see http://www.ncbi.nim.nih.gov/BLAST), or the methods described herein. Examples of other suitable computer programs include those described by Bedell et al. (2000), Clough et al. (1996) and Jurka et al. (1996). In some cases primers will be designed from known interspersed repeat units such at Alu repeats. In other instances, computer programs which scan known genomic sequences can be used to identify primers suitable for the methods of the present invention.

Examples of primers useful for the methods of the invention include, but are not limited to, ATGAGCTTGTCTA-CACCT (SEQ ID NO: 1), GGCACAATCGGTCCTACCA-GAGCTA (SEQ ID NO: 2), GAGATCGAGACCATCCTGGCTAACAA (SEQ ID NO: 3), and CCGTGTTAGCCAGGATGGTCTCGAT (SEQ ID NO: 8). The latter two are derived from human Alu repeats (FIG. 7) and are referred to herein as P3 and P1 respectively.

As outlined above, these primer sequences can be varied slightly, for example extensions at the 5' end or changing one or two nucleotides, without effecting their usefulness for the methods of the invention. Furthermore, other primers can readily be designed for use in the methods if the invention based on the known sequences of Alu repeats (see, for example, Alu sequences provided in FIG. 7, SEQ ID NO's 13 to 15, as well as in Batzer and Deininger (2002), Kapitonov and Jurka (1996), Antunez-de-Mayolo et al. (2002), Batzer et al. (1996a), Batzer et al. (1996b)). Additional examples of primers which will hybridise to Alu repeats which might be used in the methods of the present invention include, but are not limited to, CTCACGCCTGTAATCCCAGCACTTTG (SEQ ID NO: 4), GGATCACGAGGTCAGGAGATCGAGA (SEQ ID NO: 5), GCCGAGATCGCGCCACTGCACTCAG (SEQ ID NO: 6), GGCTGAGGCAGGAGAATGGCGTGA (SEQ ID NO: 7), and reverse complements thereof. As the skilled addressee would be aware, SEQ ID NO's 13 to 15 are only provided as a few examples of Alu repeats which can be used to design primers for the amplification of complementary duplicons. Many other known Alu repeats could be used.

Similar to Alu repeats, there are many other known interspersed repeat units in the genomes of most (if not all) organisms which, considering the present disclosure, could readily be targeted for the design of primers for use in the methods of the invention. Examples include, but are not limited, LINE repeats of primates (see, for example, SEQ ID NO: 16 and Smit et al., 1995), transposable elements from insects such as *Drosophila melanogaster* (Bartolome et al., 2002; Lozovskaya et al., 1995; Perez-Gonzalez et al., 2003; Vieira et al., 2002), retrotransposons of plants (such as Ty1-copia) (Flavell et al., 1992; SanMiguel, et al., 1998; Wang et al., 1999), ID SINEs of rodents (Kass et al., 1996), Mys retrotransposons of rodents (Lee et al., 1996), B1 SINEs of rodents (Zietkiewicz and Labuda, 1996) and Tigger transposons of primates (Smit and Riggs, 1996).

Examples of primers designed from primate LINE repeats which might be used in the methods of the present invention include, but are not limited to, AGAGCAGAACTGAAGGAAATAGAGAC (SEQ ID NO: 17), CCAAGCAGACCTAATAGACATCTACA (SEQ ID NO: 18), ATAGTTGGAAGTAAAGCTCTCCTCAG (SEQ ID NO: 19), TCCTCAGTGACCTACAAAGAGACTTA (SEQ ID NO: 20), ATACATTCCTCGACACATACACTCTC (SEQ ID NO: 21), TCCTGAATGACTACTGGGTACATAAC (SEQ ID NO: 22), CTACAAGGCTACAGTAACCAAAACAG (SEQ ID NO: 23), CCTAATGCTAGATGACACATTAGTGG (SEQ ID NO: 24), CTAACAACCAGAAAGGACATCTACAC (SEQ ID NO: 25), CTCTTCAAGGAGAACTACAAACCACT (SEQ ID NO: 26), ATACAGAGAAGTGCTTAAAGGAGCTG (SEQ ID NO: 27), CTTTTCTCCACATCCTTGCCAGCATT (SEQ ID NO:35) and reverse complements thereof. Other primers could readily be designed when considering the sequence of the many known LINE-related repeats (see, for example, Smit et al., 1995).

As the skilled address would be aware, the sequence of the oligonucleotide primers described herein can be varied to some degree without effecting their usefulness for the methods of the invention. A "variant" of primers specifically disclosed herein includes any primers which have insertions, deletion or mutations when compared the exact sequence provided. Preferably, any variants are longer or shorter at the 5' and/or 3' end. Such variants will be required to hybridizes under amplification conditions to the same complementary duplicon as the specific primers disclosed herein and produce equivalent amplification products.

The term primer, as defined herein, is meant to encompass any nucleic acid that is capable of priming the synthesis of a nascent nucleic acid in a template-dependent process. Primers may be provided in double-stranded or single-stranded form, although the single-stranded form is preferred. Methods of primer design are well-known in the art, based on the design of complementary sequences obtained from standard Watson-Crick base-pairing (i.e., binding of adenine to thymine or uracil and binding of guanine to cytosine). Computerized programs, when provided with suitable information regarding a target complementary duplicon, for selection and design of amplification primers are available from commercial and/or public sources well known to the skilled artisan.

The primers used in the method of the invention, which anneal to the complementary duplicon sequence, preferably consists of a sequence of at least about 15 consecutive nucleotides, more preferably at least about 18 nucleotides.

Primers used in the methods of the invention can have one or more modified nucleotides. Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases. Such modifications are well known in the art.

Chimeric primers can also be used. Chimeric primers are primers having at least two types of nucleotides, such as both deoxyribonucleotides and ribonucleotides, ribonucleotides and modified nucleotides, two or more types of modified nucleotides, deoxyribonucleotides and two or more different types of modified nucleotides, ribonucleotides and two or more different types of modified nucleotides, or deoxyribonucleotides, ribonucleotides and two or more different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. Other forms of chimeric primers are, for example, 5'-(2'-O-Methyl) RNA-RNA-3' or 5'-(2'-O-Methyl) RNA-DNA-3'.

Primers may be chemically synthesized by methods well known within the art. Chemical synthesis methods allow for the placement of detectable labels such as fluorescent labels, radioactive labels, etc. to be placed virtually anywhere within the sequence. Solid phase methods as well as other methods of oligonucleotide or polynucleotide synthesis known to one of ordinary skill may used within the context of the disclosure.

Methods of Comparing Sequences (Sets)

The invention, in an embodiment, provides the creation of information about information (metadata) and then uses that metadata to enable huge computational tasks not possible until now. Up until now, published literature uses N-ary tree structures and refinements (eg. suffix trees, prefix trees and variations upon these themes).

Thus metadata about very large datasets of elements, both enumerated and non-enumerated, with the number of elements greater than 2 can be stored in N-dimensional matrices whereby structure and relationships both within and between the datasets (sets and subsets) can be found. Arbitrary transforms can be applied to the datasets both before and after creation of metadata.

An embodiment uses polynomial algebra to assign unique integer identifiers to arbitrarily large contiguous subsets of elements to be organized, stored, retrieved and interrogated using relational database technology. The use of a common polynomial formula and a common maximum polynomial power creates compatibility between sets of data with the same types of data elements.

In a further embodiment the invention is a method for assigning unique identifiers for arbitrarily large subsets of very large data sets and then the novel use of relational database technology to interrogate and define structure. One long integer can represent a million (or a billion) nucleotides. If it is required to determine if two million base sequences are the same, then two integers (representing each sequence) are compared to ascertain equality rather than do a million comparisons. This is analogous to the assignment of unique identifiers for every node in the trees used describing all possible transforms. In the genomic sense interest is in forward and reverse duplication, as well as forward and reverse complements, on all possible linear unidirectional sequences from each node and then putting that metadata into a networked topology diagram so as to make equalities obvious.

An example of the reduction to practice of the invention is in its application to searching for forward duplications, reverse duplications, forward complements and reverse complements of specific sequences within DNA sequences. The reverse complement is used to determine the position of potential primers for the BACD process.

The nature of the stored data and hence its ability to be arbitrarily transformed will also allow speculative iterative reverse engineering of genetic polymorphisms to improve understanding of evolutionary practice.

According to an embodiment there is disclosed a new approach to analysis of large sets of elements, which can include but is not limited to integers, numbers or characters including alpha-numeric characters. It uses polynomial algebra. There is also disclosed a new approach to selecting of data subsets that have arbitrary transforms defining the relationship between the subsets. The embodiment has application in finding identical or similar subsets (subsequences) of nucleotides in a DNA sequence. Other applications are found in all large data sets including those in thermodynamics, population analysis and image recognition (using arrays of pixels, to detect information on number plates, for example).

The terms "set of elements", "subset of elements" or "subset of interest of elements" are used generally to denote sets or groups of elements and the terms "sequence of elements" and "subsequence of elements", for example in the context of genomic DNA, indicate sets in which the relative positions of the said elements are defined, but otherwise may be used interchangeably with the terms "set of elements" or "subset of elements".

A Subset of Interest (SOI), in a genomic sense, is a sequence that is the subject of an arbitrarily defined transform, for example, a reverse complement or a duplication. The approach requires a decision to be made arbitrarily on the length and degree of fit necessary to qualify as an SOI. In genomic DNA this implies duplications or multiple insertions into a genome, as shown in FIG. 19. The approach includes the ability to find SOIs of the same direction, SOIs in the reverse direction, and in any arbitrarily defined transforms upon the forward and reverse SOIs. In the genomic context, this includes complementary DNA sequences on both DNA chains.

The approach can be used to determine the existence and position of SOIs in one or more sets or sequences of elements. In a genomic context, the sequences of elements could be genomes of different species, in which case the method enables one to search for homology and sequence conservation across different species. Referring to FIG. 20, there is shown two sequences of nucleotides with two identical SOIs across both sequences, one offset from the other.

To find absolutely identical SOIs, a method of doing this is to create (N-D) subsequences within the set of interest where N is the set size and D is the number of elements in the subset being investigated (duplicon length). An individual identifier is then assigned to each subset (based on a function of D) which can then be ordered. Unique numeric—integer identifiers are ideal as they have natural order. This first method uses polynomial algebra 4 bit representation.

When using the following algorithm to find and compare SOIs, the set element at position n (of N) is assigned a prime number in an S bit nibble of binary digits or bits. S is a function of the number of discrete values an element of the set may take and is defined as:

$$Q \geq 2^S \geq P$$

where P is the smallest prime number sufficient to assign a prime number to each of the elements in the enumeration set rounded and Q is the next prime number in the set of ordered prime numbers. In a genomic context, S is 4 and A is binary 0011 (decimal 3), C is binary 0101 (decimal 5), G is binary 0111 (decimal 7), T is binary 1011 (decimal 11) and X is binary 1101 (decimal 13). Prime numbers are used to allow determination of the specific element change between sets or subsets. In a genomic context this allows identification of specific nucleotide substitution, deletions or insertions.

Bit sets are probabilistically compared by calculating a unique identifier for each bit set, such as a polynomial remainder, then comparing their identifiers. If the polynomial remainders are different, the subsequences are different. If the polynomial remainders match, there is a small chance that the subsequences are actually different. This probability may be made arbitrarily smaller with larger common polynomial divisors.

A system of assigning unique identifiers for arbitrarily long bit sequences is modulo 2 polynomial arithmetic. This method uses an incrementally shifting "window" which calculates a polynomial remainder, against a predefined polynomial of the order of at least S+1, for each SOI of size D. As the only valid integers coming from modulo 2 arithmetic can be 0 and 1, a polynomial is created with coefficients of either 0 or 1 which then determines the existence or not of an element at position n (n<D-N).

The simplest way to describe the process is to assign the $n^{th}$ bit of any string of N bits as the coefficient of an imaginary variable x in a polynomial expression to the power of N−1. For example if the bitset was 011010110101 this would be interpreted as the polynomial:

$$0x^0 + x^1 + x^2 + 0x^3 + x^4 + 0x^5 + x^6 + x^7 + 0x^8 + x^9 + 0x^{10} + x^{11}$$

i.e. $x + x^2 + x^4 + x^6 + x^7 + x^9 + x^{11}$

If each polynomial, a potential SOI, is divided by a common polynomial expression (of order k), and then that polynomial divisor is added to the generated polynomial remainder (of order k−1) a polynomial is generated that will be unique to the original polynomial such that the probability of erroneously generating a non unique polynomial is $1/(2^k)$. If using a 32 bit divisor polynomial the probability of error is less than 1 in a billion. There are a number of divisors published by IEEE which minimize potential error levels dependent on the nature of the bit set.

Thus, the above method identifies one or more subsets of elements such that at least one element in the one or more subsets of elements is located in a selected subset of interest (SOI). Each of the one or more subsets of elements and the selected SOI form part of at least one set of elements. The method includes the steps of:
(1) determining an identifier for the SOI;
(2) determining an identifier for each of the one or more subsets of elements; and
(3) comparing each identifier of the one or more subsets to the SOI identifier in order to find elements in any of the one or more subsets that are also in the SOI which occurs when the compared identifiers are identical.

A computer program can be used to instruct a processor to identify one or more subsets of elements such that at least one element in the one or more subsets of elements is located in a selected subset of interest (SOI). Each of the one or more subsets of elements and the selected SOI form part of at least one set of elements. The program instructs the processor to undertake at least steps (1), (2) and (3) and any other steps of the method.

The usefulness of these algorithms is based upon two facts:
1) Modulo 2 arithmetic (dividing the coefficients of the original expression by the coefficients of the divisor polynomial) is implemented as a simple exclusive-or (XOR) which is a native machine instruction using simple XOR gates in hardware.
2) Sliding the "window" or frame along the bit sequence (representing the elements of the set of interest) is a simple native shift-left machine instruction. This means computation (and hence time) is kept to a minimum. It also has the advantage of being a one pass operation.

There are a number of polynomial divisors which are tuned to pick up particular sequence variations such as a single bit being complemented, "burst changes" of multiple elements (e.g. nucleotides relating to particular polymorphism rates (f{polymorphism frequencies})) and various more esoteric conditions which arise.

When the unique identifier (the polynomial remainder) is stored against the location identifier (position in the sequence) in matrix form, very rapidly all duplications of length D can be identified.

Exactly the same process can be applied to other information of interest in genomics, for example forward sequence, complementary sequence, reverse sequence and reverse complement.

A second method, using polynomial algebra 2 bit representation, can be applied to "fully qualified complete" SOIs and in the genomic context A is binary 00 (decimal zero), C is binary 01 (decimal 1), G is binary 10 (decimal 2) and T is binary 11 (decimal 3). Thus the SOI is compressed to W/2 nucleotides where W is the native word size of the computer being used. The native word size of average desktop PC and typical development environments is always a multiple of 2. The architecture being released for desktop workstations with provision for multiples of the latest design CPUs have bus widths $\geq 128$ bits and concurrent NPUs (No of $\geq 4$) allowing 128 nucleotides to be processed at the rate of $10^{12}/10^2$. i.e. $\sim 10^{10}$. Using a separate CPU for controlling kernel events with memory transfer rates fast enough, a set of unique identifiers can be calculated for the human genome (subset size N is not a factor in time taken) in just less than 1 second. Currently used PC technology will allow information about $\sim 4*10^{19}$ sequences to be stored from one set of data. (i.e. $\sim 10^{10}$ subsets of information radiating from every nucleotide in a strand of human DNA).

In practice the process can be further simplified, in a third method, by the removal (by masking) of repetitive sequences which are of no interest in the particular analysis. If a masked sequence (that is A,C,G,T,M or equivalent) is used, then assign the prime numbers A=010 (decimal 2), C=011 (decimal 3), G=101 (decimal 5), T=111 (decimal 7) and masked symbol M=000 allowing compression of 10 elements into a 32 bit word. Although this gives a slightly smaller compression ratio, it allow use of the Most Significant Bit (MSB) as an indicator of whether this word needs to be processed at all, giving very significant processing time gains. Most masking produces very large sets of MMMMMMMMMMs (being substituted for A,C,T or G) within the entire sequence hence it is possible to also then include how many words to skip (or shift left) without processing in these words. That is, MSB=0 implies don't process this word for a polynomial remainder, instead read it as an integer containing information about the number of bits to skip. MSB=1 implies process this word. Using the prime numbers to represent nucleotides also makes calculation of Hamming Distances as part of a single pass much simpler.

Hamming distances are also used in data communications as a method of parity based Forward Error Correction however the Hamming distance can be interpreted as the number of bits which need to be changed to turn one subset into another. If looking for inexact subset matches, by choosing particular generator matrices it is possible to define a closeness of fit of one SOI with another, that is the degree to which one SOI has the same sequence of characters (or numbers), by using the Hamming distance. This is a good approximation of the degree of fit.

The number of bits which differ between two binary strings is, more formally, the distance between two strings A and B and is expressed as $\Sigma |A_i - B_i|$.

Using any of the above three methods allows creation of indexed tables 4+C columns where C is the number of non-direction related transforms applied to the original subset. In the genomic context, C could equal 6 with columns representing:
 the nucleotide offset in the sequence;
 the nucleotide type i.e. A, C, G, T or N if unknown;
 the unique identifier associated with the forward sequence at position n;
 the unique identifier associated with the reverse sequence at position n;
 the unique identifier associated with the complement of the forward sequence at that point; and
 the unique identifier associated with the complement of the reverse sequence at that point.

This allows representation of both DNA strands.

Binary trees are used to order and index the polynomial remainders to make comparisons and explorations fast. After the SOIs are identified, their positions, or offsets, in the sequence are stored in a matrix such that the metadata related to structure can be analyzed. An example of such a matrix is given in FIG. 21, which shows the relationship between two separate sequences using a sliding window size of 25.

In the application of these methodologies to genomics, there are four fundamental relationships of interest (but many sets of these four fundamental relationships) but as there is an increase in the number of dimensions in a matrix in which the datasets reside (eg DNA sequence is in linear matrix of Power (P)-1), the power of the strategy increases (see FIG. 22). For example, a 2D array of information, such as multiple DNA sequences, with the same number of fundamental relationships will provide 32 datasets at a point. A 3D array, such as sequences from different species and families from each species in the third dimension, will provide 128 subsets at a point and a 4D set, for example proteins changing in time, will give 1024 subsets.

The matrix may extend to an N-dimensional array, where N is the largest integer possible, such as 256 dimensions. The matrix may be a set of tables in a database. The matrix may comprise elements located at differing lengths of subsets of interest with the position of each element defined within the matrix. An identifier, such as a polynomial remainder derived from an SOI length and using polynomial arithmetic, may be stored at each position and at each SOI length in the matrix, the identifier representing information or metadata about each SOI. The dimensions of the matrix may be linear, reverse compliment of any number for example.

In identifying non-identical subsets of elements from one or more contiguous sets of elements in the matrix, a pair of matching identifiers in each set at an SOI length may be found and thereafter subsequent pairs of matching identifiers may be found at the same SOI length or a different SOI length. An example of this is described with reference to FIGS. 24 and 25.

The number of data subsets identifiable at a point in an N dimensional matrix is:

$$(f\{F(N\hat{\ }N)\}*(\text{number of fundamental relationships of interest at the point})*(\text{Number}$$

of relationships of different subset size.))

For partially qualified SOIs, that is SOIs with a completeness of fit less than the a duplicant size, there are two algorithms constructed and used in relation to linked lists and to a database (matrix) of tables. The algorithms may be used with respect to finding subsets in sets in any field where the sets can be represented as being contiguous having elements of any description and wherein identifiers or polynomial remainders can be calculated.

In the first case, linked lists with the element position as the primary node identifier are constructed. The first node of the secondary list off each primary node contains the element identifier. In the genomic sense, the element is a nucleotide with identifier (A,C,T,G,X). For every primary node, the secondary linked list contains the offsets to the next occurrences of that element (nucleotide) until the offset is greater than the SOI size or duplicon size. Such a linked list is shown in FIG. 23. The first column lists the position number in the particular sequence of the nucleotide in the second column. In the third column is listed the respective complement of the nucleotide in the second column. The remaining columns list the next 8 positions of offset of a particular nucleotide in the sequence. Thus for example, at position 3 of nucleotide T, the next occurrence in the sequence of T is listed at four positions in the first offset column and therefore appears at position 7 in the sequence.

The probability of misfit is directly proportional to the length of the SOI and hence by checking the "most distant" element of potential SOIs and working back to the nearest element in the potential SOI it is possible to very quickly discount most sequences. In a genomic context, this method also allows judgement about where the potential primer fit must be best, for example in the first 5 nucleotides, to maximize binding and how close misfit nucleotide may be to one another to maximize primer binding.

Referring to the matrix in FIG. 23, if the subsequence being searched for repeats was ACTGA from positions 1 to 5 in the sequence, then one would look at the most distant element A at position 5 and note the offset to the next A. The next offset is at 5 positions from position 5, that is position 10. Working back from position 10 to positions 9, 8 etc yields GG which is not the same subsequence. Thus one moves to the next occurrence, or two offsets is at 9 positions from position 5, that is, position 14. Working back from position 14 to 13, 12 etc yields GTCA, which is the same sequence as ACTGA. Hence the next identical sequence at positions 10 to 14 has been located. Other repeated sequences have been identified by the vertical lines at the right of FIG. 23.

The embodiment of FIG. 23 is an example of the broader method of identifying one or more subsets each having elements that substantially match elements in a subset of interest (SOI). Each of the subsets form part of a set of elements or sets of elements. The method includes the steps of:

(i) forming a matrix including a list or partial list of each element in the set or sets, the position in the set or sets of each element and at least one offset indicating the position of another of the same element in the set or sets;
(ii) selecting the position of an element in the SOI;
(iii) identifying one or more of the offsets for the selected element and for adjacent elements to the selected element in the selected SOI,
(iv) finding matching elements in the set or sets of elements to the elements in the selected SOI based on the offsets.

The largest possible offset can be used to find the matching elements.

A computer program can be used to instruct a processor to identify one or more subsets each having elements that substantially match elements in a subset of interest (SOI). Each of the subsets form part of a set of elements or sets of elements. The program instructs the processor to undertake at least steps (i) to (iv) above and any other steps disclosed in relation to the embodiment of FIG. 23.

In the second case, modulo 2 polynomial arithmetic (using polynomial algebra 4 bit representation) is used to construct matrices of unique identifiers. Rather than single tables, a database of matrices is constructed identical to those in the above-mentioned first method but with a spread of duplicon size (D) from smallest SOI to largest SOI. The above-described N-dimensional matrices may also be constructed which can be a set of tables in a database. In reduction to practice in, a genomic environment, this then allows identification of sequences which are not identical but allow creation of the best possible sequence across DNA sequences either from multiples within or across species with best fit. The primers may be made from a match of 7, miss match one, a match of six, a miss match of 1 and a match of 6 or any other combination. Different sequences with the same degree of mismatch may imply primers of different power because of the nature and position of the mismatches.

With reference to FIG. 24 there is shown a matrix forming a relational database, which is essentially a matrix in two dimensions, showing rows of position numbers n to n+30 in forward sequence S1 and reverse complement sequence S2 and columns of duplicon size D=5 up to D=10 for both S1 and S2. All of the elements (numbers) in the matrix represent remainders calculated at that position for the SOI of particular duplicon size. Thus for example, starting with S1, D=10 at position 1 a remainder of 246 exists. A corresponding remainder of 246 exists at position n+9 in the complement S2 defining the length of SOI, D=10 as there is a separation of 10 positions between S1 and S2 for this same remainder. The largest separation possible for a corresponding remainder of 246 is searched on the reverse complement sequence S2, which is located at position n+15. Any such pairing is searched at the largest duplicon size, such as D=10. The remainder of 246 was calculated after converting the binary representations of the elements/nucleotides at positions n to n+9 into a polynomial expression, dividing this by a common polynomial divisor to form a polynomial remainder. The coefficients of the polynomial remainder are converted into digital form and then into decimal form giving 246.

The position of remainder 246 in S2, D=10 determines from where the next highest D pairing is to be searched. The next highest D size with such a pairing occurring from position n+10 onwards is at position n+11 in S1, D=5 which has a remainder of 789. As D=5 a corresponding 789 in S2 must be found beyond position n+15 in S2, five positions or elements along the sequence. This occurs at position n+21 in S2 for the reverse complement.

The next pairing is searched from position n+16, starting from the longest duplicon size of 10 and systematically working down the sizes and positions in the sequence until the next pairing is found. This occurs in S1 and S2 of D=7 at positions n+17 and n+29 respectively where the remainder is 20.

Thus forward subsets of interest have been identified at n to n+9, n+11 to n+15 and n+17 to n+23.

The reverse compliment sequence S2 is also determined from duplicon size D. Thus in S2 for D=10, 5 and 7 corresponding remainders are found to form the reverse compliment sequence. For D=7, a gap of 7 positions finds a remainder of 20 at positions n+29 in S2 and n+23 in S1. For D=5, a gap of 5 positions with a remainder of 789 is located at positions n+21 in S2 and n+17 in S1. For D=10, a gap of 10 positions with a remainder of 246 is located at positions n+15 in S2 and n+6 in S1.

The above forward and reverse compliment sequences represent identical mismatches.

In FIG. 25 there is shown a relational database, which is a matrix in two dimensions indicating a forward sequence and a different reverse compliment sequence with a certain degree of fit.

Again, all of the numbers in the matrix represent remainders calculated at that position for the SOI of particular duplicon size. The longest D size is searched for similar remainder values separated by largest position along the sequences by that D size. Thus for D=10, a remainder of 246 is located at position n in S1 and at position n+1030 in S2. The next longest duplicon size is searched from position n+10 in S1 for a match in remainders separated by the largest number of positions in that size. The search reveals a match for D=5 with a remainder of 289 at position n+11 for S1 and n+1019 for S2. To continue the forward sequence, the next longest D size is searched from position n+16. This reveals a match for D=7 with remainder of 20 at position n+17 in S1. and at position n+23 in S2, seven positions forward in the sequence counting the first position at n+17.

Thus the forward subsets of interest have been identified at positions n to n+9, n+11 to n+15 and n+17 to n+23.

For the reverse compliment sequence in S2, this does not completely follow the forward sequence but has a particular degree of fit. In D=10 the corresponding remainder of 246 in S2 at position n+1030. Then the search continues for positions lower than n+1020 (as there are ten positions between n+1030 and n+1021) which is for D=5, a remainder of 289 is at position n+1019 in S2. The reverse sequence diverges from here with a degree of mismatch, as rather than D=7 being used, D=8 is used to find a mismatching remainders. Moving upward (lower) from position n+1015, a remainder of 70 is found in D=8, S2 at position n+1014. This is instead of matching remainder of 20 at D=7 in S2, position n+1013. The reason being is to use a greater duplicon size.

The embodiments of FIGS. 24 and 25 are examples of the broader method of identifying one or more subsets of elements in at least one set of elements, such that the one or more subsets being searched match a subset of interest (SOI) to a predefined level of congruency. The method includes the steps of:

(a) forming the N-dimensional matrix of elements, wherein a transform of a subset of the one or more subsets is represented by a dimension of the matrix;

(b) storing an identifier at each position in the matrix, each identifier representing a subset transform;

(c) finding at least one pair of matching identifiers in the matrix.

A computer program can be used to instruct a processor to identify one or more subsets of elements in at least one set of elements, such that the one or more subsets being searched match a subset of interest (SOI) to a predefined level of congruency. The program instructs the processor to undertake at least the steps (a), (b) and (c) above as well as any other steps disclosed in relation to the embodiments of FIGS. 24 and 25.

Further references are provided at:
http://www.nist.gov/dads/HTML/cyclicRedundancyCheck.html
http://www.mathpages.com/home/kmath458.htm
http://www.nist.gov/dads/HTML/hammingdist.html Identification of Primers Using "field of integers—modulo 2 Polynomial Arithmetic" as in Example 1, construction of tables of unique identifiers are made, but rather than single tables, a database of multiple tables is constructed with a spread of duplicant size from 3 to 40. This then allows the creation of primers across DNA sequences either from multiples within or across species with best fit. The primers may be made from a match of 5, miss match one, a match of seven, a miss match of 2 and a match of 10. An example is shown in FIG. 17 showing a forward sequence and a reverse sequence.

Amplification Procedures

Amplification may be carried out according to any method which results in amplification of sequences found between the primer(s) binding sites. Suitable methods include Polymerase Chain Reaction (PCR) and related amplification procedures using a single primer.

PCR is a reaction in which replicate copies are made of a target polynucleotide typically using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). However, as outlined herein, standard PCR methods can be modified in certain embodiments for amplifying complementary duplicons by using only a single primer.

The amplification step is preferably carried out under low to medium stringency conditions, i.e. with annealing conditions characterized by about 40° to about 46° C., preferably about 43° C. The amplification conditions are designed to allow for annealing and primer extension so that amplification occurs and are dependant, amongst other things, upon the sequence and length of the primer, and the DNA sample.

Preferred amplification conditions include a denaturing temperature of about 90 to about 98° C., an annealing temperature of about 40 to about 46° C. and extension temperature of about 70 to about 75° C. However, reaction conditions need only be suitable the amplification of the targeted complementary duplicons. Procedures for optimizing reaction conditions when using a primer(s) which target specific complementary duplicons is well within the capacity of the skilled addressee.

The polymerase used for the amplification forms an extension of a primer along a DNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Klenow fragment, reverse transcriptase, Vent DNA polymerase, Pfu DNA polymerase, Taq DNA polymerase, and the like, derived from any source such as cells, bacteria, such as $E.\ coli$, plants, animals, virus, thermophilic bacteria, and so forth.

Separation Methods

Following amplification, the amplification products are separated to generate the profile characteristic of the genome. Any methods known in the art can be used to separate, and optionally quantify, the amplification products, some of which are described in further detail below.

Gel Electrophoresis

Separation by gel electrophoresis is based upon the differential migration through a gel according to the size and ionic charge of the molecules in an electrical field. High resolution techniques normally use a gel support for the fluid phase. Examples of gels used are starch, acrylamide, agarose or mixtures of acrylamide and agarose. Frictional resistance produced by the support causes size, rather than charge alone, to become the major determinant of separation. Smaller molecules with a more negative charge will travel faster and further through the gel toward the anode of an electrophoretic cell when high voltage is applied. Similar molecules will group on the gel. They may be visualized by staining and quantitated, in relative terms, using densitometers which continuously monitor the photometric density of the resulting stain. The electrolyte may be continuous (a single buffer) or discontinuous, where a sample is stacked by means of a buffer discontinuity, before it enters the running gel/running buffer. The gel may be a single concentration or gradient in which pore size decreases with migration distance.

Agarose gel electrophoresis facilitates the separation of DNA based upon size in a matrix composed of a highly purified form of agar. Nucleic acids tend to become oriented in an end on position in the presence of an electric field. Migration through the gel matrices occurs at a rate inversely proportional to the logo of the number of base pairs (Sambrook et al., 1989, supra).

Polyacrylamide gel electrophoresis is an analytical and separative technique in which molecules are separated by their different electrophoretic mobilities in a hydrated gel. The gel suppresses convective mixing of the fluid phase through which the electrophoresis takes place and contributes molecular sieving. Polyacrylamide gel electrophoresis is able to resolve amplification products which are relatively small in size (1,500 base pairs of less) when compared to the resolution achieved for the same small fragments using agarose gel electrophoresis. Preferably, the concentration of polyacrylamide in the gel is about 5%, however, any concentration suitable for producing the required separation can be used.

Microfluidic Techniques

Microfluidic techniques include separation on a platform such as microcapillaries, including by way of example those designed by ACLARA BioSciences Inc., or the LabChip™ by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, WO 94/05414 reports an integrated micro-PCR apparatus for collection and amplification of nucleic acids from a specimen. U.S. Pat. No. 5,304,487, U.S. Pat. No. 5,296,375, and U.S. Pat. No. 5,856,174 describe apparatus and methods incorporating the various processing and analytical operations involved in nucleic acid analysis.

Capillary Electrophoresis

In some embodiments, it may be desirable to provide an additional, or alternative means for analyzing the amplified DNA. In these embodiments, microcapillary arrays are contemplated to be used for the analysis. Microcapillary array electrophoresis generally involves the use of a thin capillary or channel that may or may not be filled with a particular separation medium. Electrophoresis of a sample through the capillary provides a size based separation profile for the sample. Microcapillary array electrophoresis generally provides a rapid method for size-based sequencing, PCR product analysis, and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, for example, U.S. Pat. No. 5,904,824. Typically, these methods comprise photolithographic etching of micron scale channels on a silica, silicon, or other crystalline substrate or chip, and can be readily adapted for use in the present disclosure.

In many capillary electrophoresis methods, the capillaries, e.g., fused silica capillaries or channels etched, machined, or molded into planar substrates, are filled with an appropriate separation/sieving matrix. Typically, a variety of sieving matrices known in the art may be used in the microcapillary arrays. Examples of such matrices include, e.g., hydroxyethyl cellulose, polyacrylamide, agarose, and the like. Generally, the specific gel matrix, running buffers, and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea to denature nucleic acids in the sample.

Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information.

In Japanese Patent No. 59-131909, an instrument is described that detects nucleic acid fragments separated either by electrophoresis, liquid chromatography or high speed gel filtration. Mass spectrometric detection is achieved by incorporating into the nucleic acids atoms that normally do not occur in DNA such as S, Br, I, Ag, Au, Pt, Os, Hg.

Identification Methods

Amplification products can be visualized using any method known in the art. One typical visualization method involves staining of a gel with a flourescent dye, such as ethidium bromide or Vistra Green, and visualization under UV light. Alternatively, if the amplification products are integrally labeled with radio- or fluorometrically-labeled nucleotides, the amplification products can be exposed to x-ray film or visualized under the appropriate stimulating spectra following separation.

In one embodiment, visualization is achieved indirectly, using a nucleic acid probe. For example, following separation of amplification products, a labeled, nucleic acid probe is brought into contact with the amplified products. Such probes can be designed from region of the target complementary duplicon which is downstream of where the amplification primer hybridizes.

The probe preferably is conjugated to a chromophore but may be radiolabeled. In another embodiment, the probe is conjugated to a binding partner, such as an antibody or biotin, where the other member of the binding pair carries a detectable moiety. In other embodiments, the probe incorporates a fluorescent dye or label. Other embodiments also contemplate the use of Taqman™ and Molecular Beacon™ probes.

The type of label incorporated in DNA amplification products is dictated by the method used for analysis. When using capillary electrophoresis, microfluidic electrophoresis, HPLC, or LC separations, either incorporated or intercalated fluorescent dyes are used to label and detect the amplification products. Samples are detected dynamically, in that fluorescence is quantitated as a labeled species moves past the detector. If any electrophoretic method, HPLC, or LC is used for separation, products can be detected by absorption of UV light, a property inherent to DNA and therefore not requiring addition of a label. If polyacrylamide gel or slab gel electrophoresis is used, primers for the amplification reactions can be labeled with a fluorophore, a chromophore or a radioisotope, or by associated enzymatic reaction. Enzymatic detection involves binding an enzyme to a primer, e.g., via a biotin:avidin interaction, following separation of the amplification products on a gel, then detection by chemical reaction, such as chemiluminescence generated with luminol. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analysed more than once by probing, stripping the blot, and then reprobing. If amplification products are separated using a mass spectrometer no label is required because nucleic acids are detected directly.

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed. The distance between donor and acceptor dyes at which energy transfer efficiency is 50% is referred to as the Forster distance (Ro). Other mechanisms of fluorescence quenching are also known in the art including, for example, charge transfer and collisional quenching.

Energy transfer and other mechanisms that rely on the interaction of two dyes in close proximity to produce quenching are an attractive means for detecting or identifying nucleotide sequences, as such assays may be conducted in homogeneous formats. Homogeneous assay formats differ from conventional probe hybridization assays that rely on the detection of the fluorescence of a single fluorophore label because heterogeneous assays generally require additional steps to separate hybridized label from free label. Several formats for FET hybridization assays are reviewed in Nonisotopic DNA Probe Techniques (Academic Press, Inc., pgs. 311-352, 1992).

Many donor/acceptor dye pairs are known in the art and may be used in the present disclosure. These include but are not limited to: fluorescein isothiocyanate (FITC)/tetramethylrhodamine isothiocyanate (TALIC), FITC/Texas Red™ Molecular Probes, FITC/N-hydroxysuccmimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer, or fluorescence quenching. P-(dimethyl aminophenylazo)benzoic acid (DABCYL) is a non-fluorescent acceptor dye which effectively quenches fluorescence from an adjacent fluorophore, e.g., fluorescein or 5-(2'-aminoethyl)aminonaphthalene (EDANS). Any dye pairs that produce fluorescence quenching in the detector nucleic acids are suitable for use in the methods of the disclosure, regardless of the mechanism—by which quenching occurs. Terminal and internal labeling methods are both known in the art and may be routinely used to link the donor and acceptor dyes at their respective sites in the detector nucleic acid.

A number of the above separation platforms can be coupled to achieve separations based on two different properties. For example, some of the PCR primers can be coupled with a moiety that allows affinity capture, while some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affinity chromatography column. The flow-through fraction is collected, and the bound fraction eluted (by chemical cleavage, salt elution, etc.). Each sample is then further fractionated based on a property, such as mass, to identify individual components.

Kits

The materials and reagents required for the disclosed amplification methods may be assembled together in a kit. The kits of the present disclosure generally will include at least the enzymes and nucleotides necessary to carry out the claimed method along with at least one primer. In a preferred embodiment, the kit comprises only a single primer. In another preferred embodiment, the kit will also contain directions for amplifying complementary duplicons from a sample. The kit may also comprise means for detecting the amplified nucleic acids.

In certain embodiments, the means for detecting the nucleic acids may be a label, such as a fluorophore, a radiolabel, an enzyme tag, etc., that is linked to the nucleic acid primer or the nucleotides themselves.

Also included in the kits may be enzymes suitable for amplifying nucleic acids, including various polymerases (Taq, etc.), deoxynucleotides and buffers to provide the necessary single reaction mixture for amplification.

In each case, the kits will preferably have distinct containers for each individual reagent and enzyme, as well as for each primer. Each biological agent will generally be suitably aliquoted in their respective containers. The container means of the kits will generally include at least one vial or test tube. Flasks, bottles, and other container means into which the reagents are placed and aliquoted are also possible. The individual containers of the kit will preferably be maintained in close confinement for commercial sale.

EXAMPLES

Example 1

Bidirectional Amplification of Complementary Duplicons Using a Primer Designed from the Fish ZP3 Gene The zona pellucida membrane surrounding eggs contain glycoproteins, one of which, ZP3 is reported to be a receptor for sperm. Crosstaxa sperm binding is limited and is expected to be restricted by, among other things, differences in ZP3. The process of recognition and fertilization of fish eggs takes place externally and hence would need to be highly developed to ensure specificity.

ZP3 is highly variant which we predicted to be in regions with imperfect duplications. The locus and surrounding sequences from different species of fish were aligned (CLUSTALW) in order to design primers in the conserved and duplicated regions. The regions were found to contain a number of repetitive sequences. This was advantageous as it provided evidence of duplication. The preferred length of around 20 mers (which was not considered to be critical) was used to select a number of primers to be tested. Two primers were the most promising in terms of duplicated motifs, BLAST and thermal analyses. One of these also exhibited some sequence homology to alternative splice site sequences and to sequences containing retroelements, thereby suggesting multiple binding (see Table 1 and FIG. 2). Interestingly the major amplicons were found to be the product of this primer alone (i.e. operating as both a forward and reverse primer—see hypothetical example in FIG. 1). This primer (SEQ ID NO: 1) was tested by PCR, (see conditions described in detail below), on a number of DNA samples (human and non-human primates) which were extracted from cell lines from the 4AOH cell panel (Cattley et al., 2000). Horse DNA was extracted from blood samples collected by a veterinarian. Fish DNA was prepared from fresh liver samples obtained from a local supplier. We tested a number of relatively low annealing temperatures (43-50° C.) to allow for expected polymorphism in the primer binding sequence in different species (see U.S. Pat. No. 6,383,747 for example).

Fluorescent detection of amplified products using various DNA samples (examples include: R85/1518B—Human; R92/1949K—Chimpanzee; R92/12977E—Orang-utan; C02/465H—Mouse; C02/369W—Horse; C01/1607N—Grouper) and primer ZP3 Ex2F (Tm=46° C.). In these examples, multiple genomic DNA amplicons were amplified simultaneously from a single individual's DNA sample using a single primer ZP3 Ex2F (SEQ ID NO: 1) at 50 ng in a single reaction vessel. The PCR amplification was performed in a 20 µl volumes consisting of 1×PCR Reaction Buffer (16.6 µM [NaH$_4$]$_2$.SO$_4$, and 67 µM Tris-HCl (pH 8.8) at 25° C.), 0.45% Triton X-100, 3 mMoles MgCl$_2$ and 500 µMoles each of dATP, dCTP, dGTP and dTTP using 100 ng DNA template, and 1.4U Taq DNA Polymerase.

A Thermal Cycler (Gradient Palm Cycler™, Corbett Research, Mortlake, NSW) was employed with the following amplification protocol: 95° C. for 2 min., then 35 cycles of 94° C. for 30 sec., 43° C. for 30 sec., and 72° C. for 30 sec., followed by 1 cycle of 72° C. for 5 min., and 15° C. for 1 sec.

Amplified products were separated by 5% polyacrylamide gel electrophoresis on a 18.5 cm gel in 0.6 TBE buffer with 30 µg/l EtBr for 90 min at 900v and the products were visualised by detection of the fluorescent signal using a fluorescent scanner (Gel-Scan 2000 ™, Corbett Research, Mortlake, NSW).

Reference is made to FIGS. 3 to 6 which display the profile of the amplified fragments (with size on the x axis and intensity on y axis) from various samples of different species.

Figure 3:
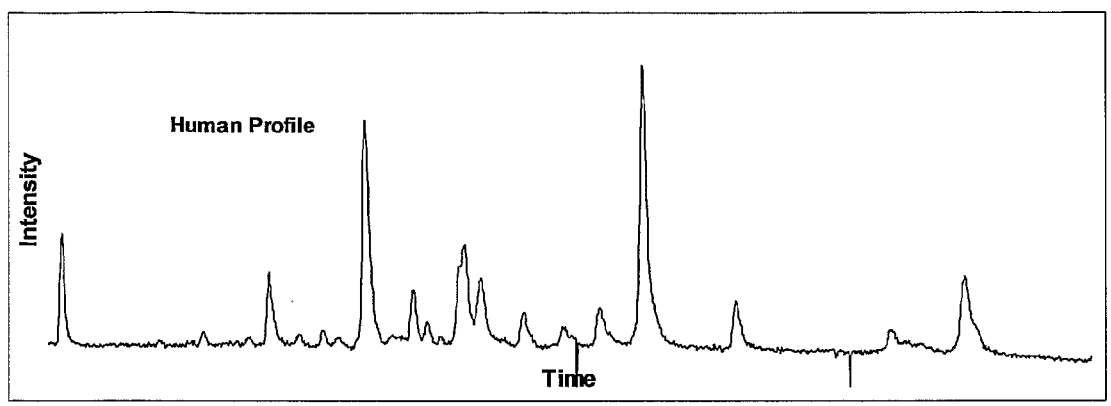
FIG. 3 shows a human profile obtained by amplification of DNA using a method according to an embodiment of the present invention.
Figure 4:
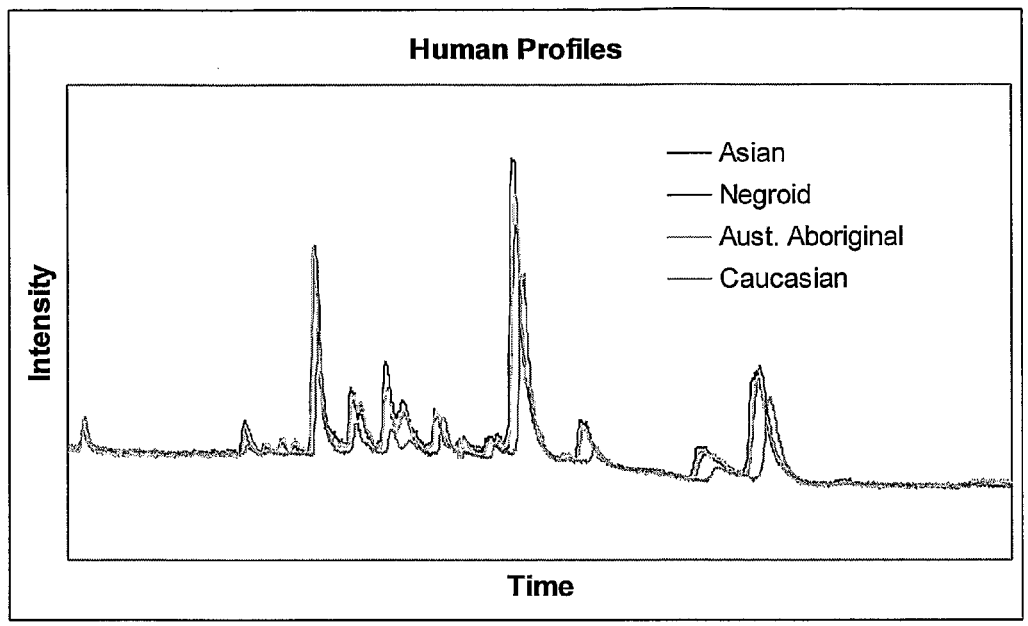
FIG. 4 shows profiles obtained by amplification of DNA from different human populations using a method according to an embodiment of the present invention.

FIG. 4 shows the profiles generated using the same system to generate products from amplification from Asian, negroid, Australian aboriginal and Caucasian genomic DNA. As can be seen in FIG. 4, each population or group gives an almost identical profile.

Figure 5:
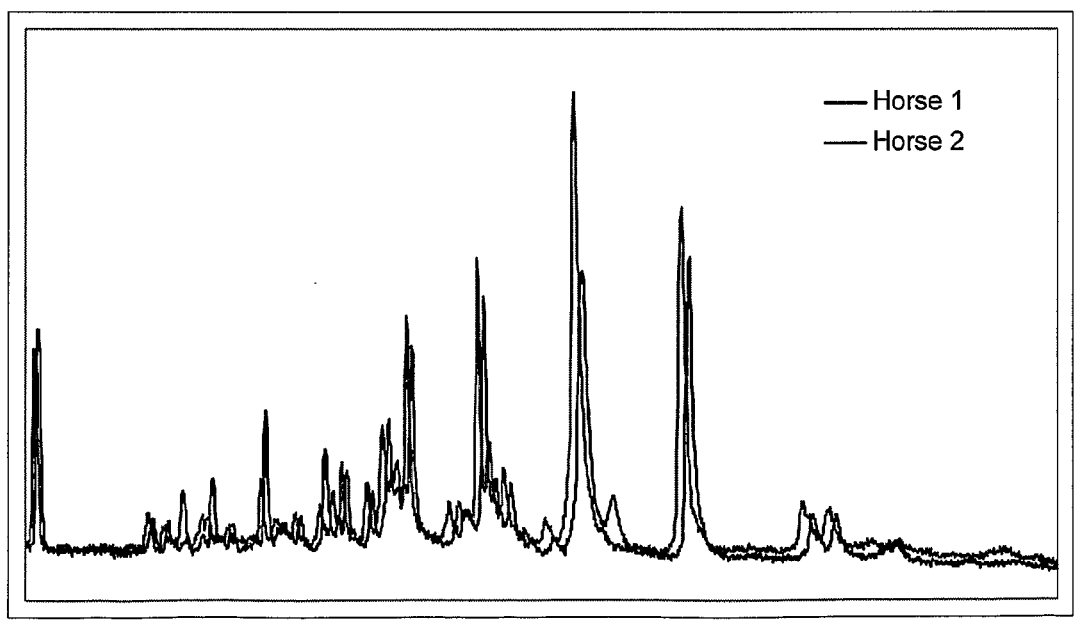
FIG. 5 shows profiles obtained by amplification of DNA from different horse samples using a method according to an embodiment of the present invention.
Figure 6A:
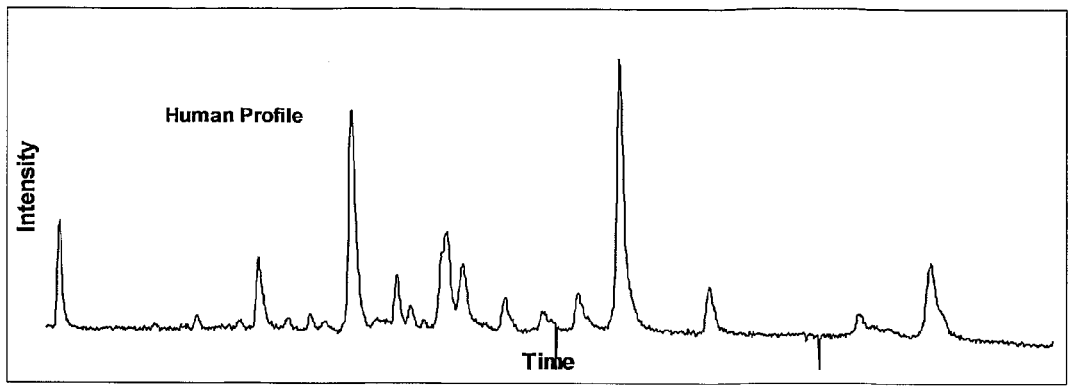
FIG. 6 shows profiles obtained by amplification of DNA from (a) humans, (b) chimps, (c) orangutan and (d) an overlay of the profiles of (a), (b) and (c) using a method according to an embodiment of the present invention.
Figure 6B:
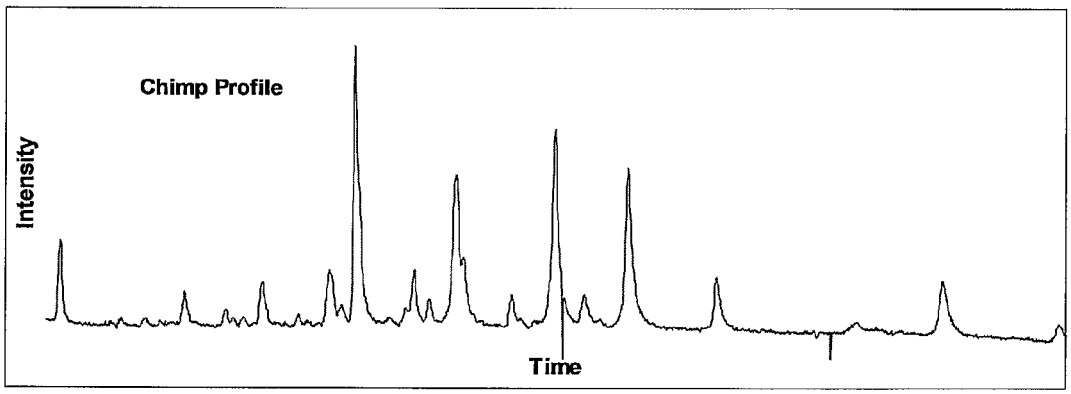
Figure 6C:
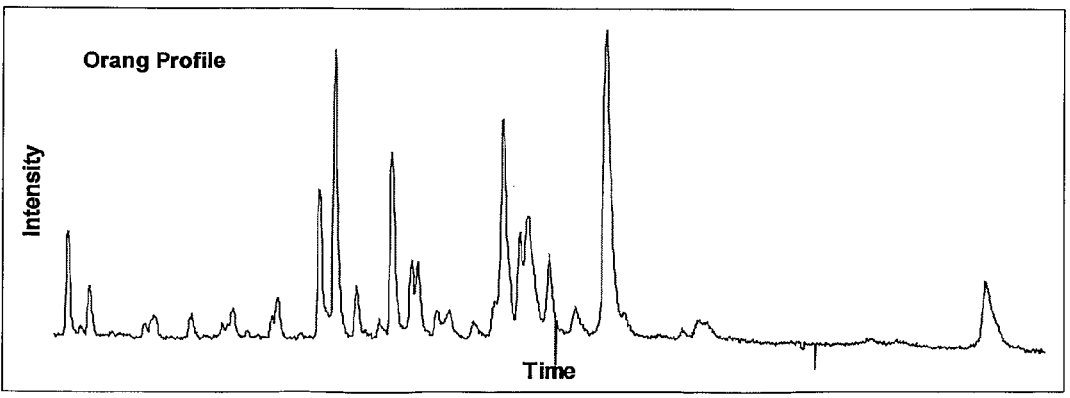
Figure 6D:
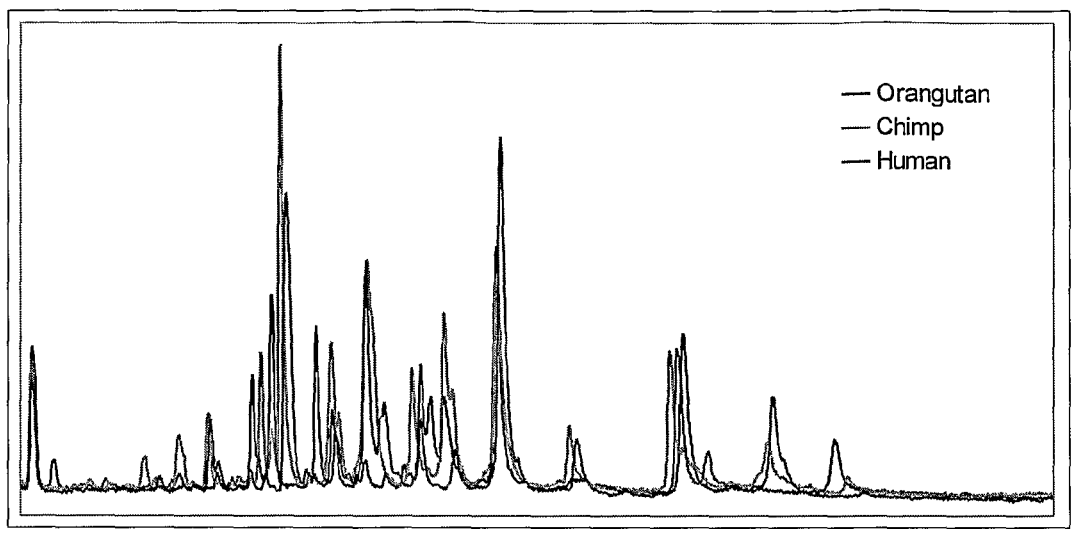

FIG. 5 shows the profiles generated using the same system to generate products from amplification from two samples of horse genomic DNA.

FIG. 6 shows each of the profiles generated using the same system to generate products from amplification from (a) human, (b) chimp, and (c) orangutan, and shows (d) an overlay of all profiles showing that the profiles are indeed species specific. The magnitude of the differences between species could be quantified and compared to known separation (divergence) times. Thus, the method provides a measure of the evolutionary relationships between species.

Other species successfully profiled using the ZP3 primer (SEQ ID NO:1) include, fish species—Barramundi (*Lates calcarifer*), Snapper (*Pagrus auratus*) and Grouper (*Epinephelus areolatus*); marsupials and other Australian animal species—Chuditch (*Dasyurus geoffroii*), Bennets Tree Kangaroo (*Dendrolagus bennettianus*), Lumholtz Tree Kangaroo (*Dendrolagus lumholtzi*), Agile Wallaby (*Macropus agilis*), Wallaroo/Euro (*Macropus robustus*), Red Kangaroo (*Macopus rufus*), Gray Kangaroo (*Marcopus fuliginous*), Bilby (*Macrotis lagotis*), Quokka (*Sentonix brachyurus*), Tammar (*Macropus eugenii*), Western Pebble Mouse (*Pseudomys champmani*), Delicate Mouse (*Pseudomys delicatulus*), Desert Mouse (*Pdeudomys desertor*), Northern pebble-mound mouse (*Pseudomys johnsoni*), and North Eastern Mouse (*Pseudomys patrius*) and other mammals species—Dog (*Canis familiaris*), Cat (*Felis catus*), Cow (*Bos taurus*), Horse (*Equus caballus*), Donkey (*Equus asinus*), Mice (*Mus musculus*) and Rabbit (*Orcytolagus cuniculus*) (data not shown).

Example 2

Bidirectional Amplification of Complementary Duplicons Using Primers Designed from Human Alu Repeats Alu repeats of the human genome where analysed for primers which could be used for BACD (FIG. 7). Two overlapping primers designated P3 (GGCACAATCGGTCCTACCA-GAGCTA—SEQ ID NO: 2) and P1 (GAGATCGAGAC-CATCCTGGCTAACAA—SEQ ID NO: 3) were selected.

Fluorescent detection of amplified products using various DNA samples (examples include: C02/00470E—Horse 2, C02/00471L—Horse 3, C99/02334V Horse CR, C02/00391W—Donkey Polly; C02/00393J—Donkey Jasper; C02/00395X—Donkey Junior; C04/00485Q—Sheep C501, C04/00486X Sheep C502; C04/00487D—Sheep C503; C04/00488K—Sheep C504, C04/00489R—C505C99/02252D—Bull Emir, C04/00219T—Bull RD3, C04/00429M—Cow 0162, C04/00239D—Cow 0157, C99/01972K—Cow 9804, C00/04872N—Cow 0070, C03/00031B—Cow 9764, C04/00227Y—Cow 0428, C04/00496P—Great Dane 1, Dog Jemma, C04/00497W—Great Dane 2, C04/00472D Red Heeler) and primer P3 (SEQ ID NO: 2). In these examples, multiple genomic DNA amplicons were amplified simultaneously from a single individual's DNA sample using a single primer P3 (SEQ ID NO: 2) at 10.6 ng in a single reaction vessel. The PCR amplification was performed in a 20 µl volumes consisting of 1×PCR Reaction Buffer (Biotech TAQ-3), 1.5 mMoles $MgCl_2$ and 212 µMoles each of DATP, dCTP, dGTP and dTTP using 100 ng DNA template, and 1.4U Taq DNA Polymerase. A Thermal Cycler (Gradient Palm Cycler™, Corbett Research, Mortlake, NSW) was employed with the following amplification protocol: 95° C. for 5 min., then 35 cycles of 94° C. for 30 sec., 43° C. for 30 sec., and 72° C. for 30 sec., followed by 1 cycle of 72° C. for 5 min., and 15° C. for 1 sec.

Amplified products were separated by 4% polyacrylamide gel electrophoresis on a 32 cm gel in 0.6 TBE buffer with 15 µg/l EtBr for 120 min at 2000 v and the products were visualised by detection of the fluorescent signal using a fluorescent scanner (Gel-Scan 3000 ™, Corbett Research, Mortlake, NSW).

The results from various amplification reactions on genomic DNA from humans, chimps and cows are provided in FIGS. 8 to 14. FIG. 8d and FIG. 12 shows that the profiles obtained where highly conserved between different humans. However, the profiles obtained from humans could be distinguished from those obtained from chimps (see, for example, FIG. 9b).

Although Alu repeats are generally considered to be found it primates, surprisingly the P3 and P1 primers also amplified complementary duplicons in cow genomic DNA (FIGS. 10 and 14). As can be seen from FIG. 10c, the profiles obtained from cows when compared to humans is distinct.

Example 3

Bidirectional Amplification of Complementary Duplicons of Non-Primate Species

Interestingly, primers P1 and P3 also amplified specific and distinct bands in cattle, which were initially included as negative controls (see Example 2). As a result, the inventors analysed DNA from horse, donkeys, sheep and dogs. The amplification procedures which were used were the same as those provided above in Example 2.

Further analyses on divergent species identified species specific bands with more closely related species shared similar bands (FIGS. 15 to 18). Further, P3 identified polymorphic bands (present in some individuals of the species and not others) in cattle, dogs and the donkey.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Antunez-de-Mayolo, G. et al. (2002) Electrophoresis 23:3346-3356.

Bartolome, C. et al. (2002) Mol. Biol. Evol. 19:926-937.

Batzer, M. A. and Deininger, P. L. (2002) Nature Rev. Genet. 3:370-379.

Batzer, M. A. et al. (1996a) J. Mol. Evol. 42:3-6.

Batzer, M. A. et al. (1996b) J. Mol. Evol. 42:22-29.

Bedell, J. A. et al. (2000) Bioinformatics 16:1040-1041.

Branicki W. et al. (2003) J. Forensic Sci. 48:83-87.

Cattley, S. K. et al. (2000) Eur. J. Immunogenet. 27:397-426.

Clough, J. E. et al. (1996) J. Mol. Evol. 42:52-58.

Deininger, P. L. and Batzer, M. A. (1999) Mol. Genet. Metab. 67:183-193.

Flavell, A. J. et al. (1992) Nucl. Acids Res. 20:3639-3644.

Jurka, J. et al. (1996) Computers Chem. 1:119-121.

Kapitonov, V. and Jurka, J. (1996) 42:59-65.

Kass, D. H. (1996) J. Mol. Biol. 42:7-14.

Kulski, J. K. et al. (2001) J. Mol. Evol. 53:114-123.

Lee, R. N. et al. (1996) J. Mol. Evol. 42:44-51.

Lozovskaya, E. R. et al. (1995) Genes Develop. 5:768-773.

Miriami, E. et al. (2003) Nucl. Acids Res. 31:1974-1983.

Nelson, D. L. et al. (1989) Proc. Natl. Acad. Sci., USA 86:6686-6690.

Perez-Gonzalez, C. E. et al. (2003) Genetics 165:675-685.

Ricci, V. et al. (2003) Hum. Genet. 112:419-425.

SanMiguel, P. et al. (1998) Nat. Genet. 20:43-45.

Santos, F. R. et al. (2000) Hum. Mol. Genet. 9:421-430.

Smit, A. F. A. et al. (1995) J. Mol. Biol. 246:401-417.

Smit, A. F. A. and Riggs, A. D. (1996) Proc. Natl. Acad. Sci., USA 93:1443-1448.

Sorek, R. et al. (2002) Genome Res. 12:1060-1067.

Stenger, J. et al. (2001) Genome Res. 11:12-27.

Vieira, C. et al. (2002) Mol. Biol. Evol. 19:1154-1161.

Wang, S. et al. (1999) Proc. Natl. Acad. Sci., USA 96:6824-6828.

Zietkiewicz, E. and Labuda, D. (1996) J. Mol. Evol. 42:66-72.

Zhang, W. J. et. al. (1990) J. Exp. Med. 171:2101-2114.

The invention claimed is:

1. A method of genetic analysis comprising:
   i) amplifying a complementary duplicon(s) in genomic DNA in a sample from an individual; and
   ii) generating a profile of amplification products from step i),
   wherein the profile is characteristic of the genomic DNA, and wherein the amplification products are separated by size exclusion chromatography, and wherein the size exclusion chromatography is polyacrylamide gel electrophoresis.

2. The method of claim 1, wherein the profile is used to determine a species of the individual.

3. The method of claim 1, wherein the profile is used to determine a breed, strain or cultivar of the individual.

4. The method of claim 1, wherein the profile is used to determine whether the individual possess a particular trait.

5. The method of claim 4, wherein the trait is a disease or susceptibility thereto.

6. The method of claim 1, wherein the amplification is performed using a single primer.

7. The method of claim 1, wherein the sample comprises genomic DNA from a eukaryote.

8. A method of genetic analysis comprising:
   i) obtaining a first nucleic acid sequence profile derived from amplification of a complementary duplicon(s) in genomic DNA in a sample from an individual,
   ii) comparing the first nucleic acid sequence profile with one or more reference nucleic acid sequence profiles obtained by the amplification of the complementary duplicon(s) from one or more known species, and
   iii) determining the species from which the sample is derived based on the similarity of the first nucleic acid sequence profile when compared to the reference nucleic acid sequence profiles.

9. The method of claim 8, wherein the individual is a hybrid of two species and the method determines parent species of the hybrid.

10. The method of claim 8, wherein the amplification products are separated by size exclusion chromatography.

11. The method of claim 10, wherein the size exclusion chromatography is either agarose gel electrophoresis or polyacrylamide gel electrophoresis.

12. The method of claim 11, wherein the size exclusion chromatography is polyacrylamide gel electrophoresis.

13. A method for detecting presence of, and/or quantifying an extent of, contaminating DNA in a sample comprising:
   i) obtaining a first nucleic acid sequence profile derived from amplification of a complementary duplicon(s) in genomic DNA in a sample,
   ii) comparing the first nucleic acid sequence profile with one or more reference nucleic acid sequence profiles obtained by the amplification of the complementary duplicon(s) from one or more known species,
   iii) determining if the sample is derived from a single species based on the similarity of the first nucleic acid sequence profile when compared to the reference nucleic acid sequence profiles,
   iv) if the sample comprises DNA from at least two different species, determining the two or more species from which the sample is derived based on the similarity of the first nucleic acid sequence profile when compared to the reference nucleic acid sequence profiles, and
   v) optionally quantifying the relative concentration of the DNA from the two or more different species in the sample.

14. A method of estimating divergence times between two different species, breeds, cultivars or strains comprising:
   i) obtaining a nucleic acid sequence profile representing a range of sizes derived from amplification of a complementary duplicon(s) in genomic DNA in a sample from an individual of each species, breed, cultivar or strain; and
   ii) comparing the range of sizes derived from the amplification to determine an evolutionary relationship of the two species, breeds, cultivars or strains.

15. A composition comprising an oligonucleotide primer for use in amplifying a complementary duplicon comprising, a primer that can be used to generate a profile of amplification products characteristic of a genome of an animal wherein the primer is selected from the group consisting of:
   a) an oligonucleotide comprising a sequence selected from the group consisting of:
   ATGAGCTTGTCTACACCT (SEQ ID NO: 1),
   GGCACAATCGGTCCTACCAGAGCTA (SEQ ID NO: 2),
   GAGATCGAGACCATCCTGGCTAACAA (SEQ ID NO: 3), and
   CCGTGTTAGCCAGGATGGTCTCGAT (SEQ ID NO: 8),
   b) an oligonucleotide comprising a sequence which is a reverse complement of any oligonucleotide provided in a), and
   c) a variant of a) or b) which hybridizes under amplification conditions to a same complementary duplicon as a) or b).

16. A composition comprising an oligonucleotide of claim 15, further comprising an acceptable carrier.

* * * * *

SEQUENCE LISTING

<160> NUMBER OF SEQ ID NOS: 52

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgagcttgt ctacacct                                                 18

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcacaatcg gtcctaccag agcta                                         25

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagatcgaga ccatcctggc taacaa                                        26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcacgcctg taatcccagc actttg                                        26

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggatcacgag gtcaggagat cgaga                                         25

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gccgagatcg cgccactgca ctccag                                            26
```

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
ggctgaggca ggagaatggc gtga                                              24
```

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ccgtgttagc caggatggtc tcgat                                             25
```

<210> SEQ ID NO 9
<211> LENGTH: 1040
<212> TYPE: DNA
<213> ORGANISM: Homo sapiens

<400> SEQUENCE: 9

```
gcagctgctt gaaggcgagg cgcatggcgg cgggcagcg ccccacggag cccacgatgg        60
cgtccacgat gggccccagg tagcccgtca gcagccccag gctggtctcc cgcatctgct      120
cctccgagag tgcgcctttg aaggagatcc tcctggaggg gccggcggag cagctcagcc      180
tcggggcaca acatctgcct gctccaaacc ctccaccggc cccgctgagc tccgagagga      240
ctcatcttcc ctccacgtcc gcagcctcct tcctgcccct tcccaccggg tttcttgctg      300
ttgcttaaac acgatgagct cattcccatc ctgcagcctt tgcactggct tatctccgtg      360
cccagaacac tctcccgtta aatgttaaat ctccgcaaca ctcccttcct cacccctgc       420
aagtctttgc ttagatgtcc cctcccctgc gaggctgccc ctgtcctcac cctctggaat      480
attgcaggcc tctcccctcc ctcgtttatt ccattccctg gtcccattca ataacctttt      540
cccaaccagg cccggtggct catgcctgta atcccagcac tctgggaggc cgaggggca       600
ggtcacttga ccaggagt tcaagaccag cctggcaac atggtgaaac tccatctcca         660
ccaaaaaata caaaaattag cccagcgtgg tggtgcacgc ctataatctc agctacttgg      720
gatgctgagg caggagaatc gcttcaatat gggaagtgga ggttgcagtg agtcgagatc      780
gcaccactgc actgcagcct gggtgacaca gcgagactcc atctcaaaaa ataaataaat      840
aaataaataa accttcttcc tccagttgct cattatctgt ctccccccag aatagggact      900
tgggactatt tgttccctac tgtatcgtca gtgttcagcc cagagcctgg cactcaatca      960
ttgttttgtt ttgtggatgc tagaacagca cttttccatc tgcaattatt gtgttccttt     1020
ctttctttac agattgaggg                                                 1040
```

<210> SEQ ID NO 10
<211> LENGTH: 546
<212> TYPE: DNA
<213> ORGANISM: Homo sapiens

<400> SEQUENCE: 10

```
tctgtcttgc ccacacctag agtgacagct gggggttctc agccccactg tgtcctggac      60
ccaacgtgct gagccctgga cttgtctctg gcatggtctc ttttaatcct aacagcaact     120
tgatggggta agtagcctta cttgttcccg tttaacagat aagaaaactg aggctcagag     180
aggttactgg ggagatggca cagctgagaa tagaacccag gactgccaac tccacagcct     240
gcctgcaacc ctgccctgtc caggtcccta catgcccctg tccccatggg tgcccactga     300
gtttcctcca tcgttatcaa gtgtgctagg aaaagccctc aacttggagt ctcacagatg     360
gactgtgtcc ttctgctcag ggcctgggat caaatccttg ctctgtaatt tcctggctgt     420
atgaccttag gcaagtgacc ttccctctct gaggctcagt tgcatcatca gtaagagggg     480
gtcatgatgc ctgcctctaa agtagtcaga aggtgtggac agcacaagga aagatcctct     540
cctgtc                                                                546

<210> SEQ ID NO 11
<211> LENGTH: 811
<212> TYPE: DNA
<213> ORGANISM: Homo sapiens

<400> SEQUENCE: 11
tctgccacgg tccccagtgg ataccccagc aacaattttc cacagctcca ggcttgtggg      60
ttagacagga gaaggttctg gagagaaagg aggagcccac ggaggggtgg aatgaccccc     120
agccactgct ctgcttcctc ccaatctcat tgagctctcc acgatctccc ttgcaggcag     180
gcccactcag agaccgccaa caccacaata ataaaaatcg ctaatgttgg ggaccccag      240 cagcacagca gtaaatatca ctaatgtcga ggagcccag cagcacagta ataaagatca      300
ctaatgcttg tggagcacat gcatgactca gttaacggag cagaggtcat gagccccacg     360
tttcaggtga taatattctc accagctgga taagggacat tttagaagta gtgtgtgcat     420
taagtagaag aacattggat caatatttta ggttttttaa ttttaaaaaa tctgattatg     480
ccaggcacgg ttgttcacgc ctgtaatccc agcacttcgg gagaccaagg caggaggatt     540
gcttgagccc aggagttcga gaccagcctg gcaatgtgg caaaaccctg tctctgctaa      600
aaatgtaaaa acttagctgg gcatggtggt gtgcgcctat agtcccagct actcaggagg     660
ctgaggtgga aaaattaccc gagcccggga agttgacgct gcagtgagct gtggtcacac     720
cactgcaccc cagcctgggt gacagagtaa aaccttgtct caaaaaaaaa aaaaaagaa      780 aaaaggaaa agaaaagaag caacttaacc a                                     811

<210> SEQ ID NO 12
<211> LENGTH: 67
<212> TYPE: DNA
<213> ORGANISM: Homo sapiens

<400> SEQUENCE: 12
gggcggatca cctgaggtca ggagttcgag accagcctgg ccaacatggt gaaacccgt       60 ctctact                                                                67

<210> SEQ ID NO 13
<211> LENGTH: 500
<212> TYPE: DNA
<213> ORGANISM: Homo sapiens

<400> SEQUENCE: 13
caatagaaaa ccaatacaga acccttggct gggcatggtg gctcacgcct gtaatcccag      60
cactttggga ggccgaggcg ggcggatcac gaggtcagga gatcgagacc atcctggcta     120
```

```
acacggtgaa accccgtctc tactaaaaat acaaaaaatt agccgggcgt ggtagcgggc        180
gcctgtagtc ccagctactt gggaggctga ggcaggagaa tggcgtgaac ccgggaggcg        240
gagcttgcag tgagccgaga tcgcgccact gcactccagc ctgggcgaca gagcgagact        300
ccgtctcaaa aaaaaaaaa aaaaaaaaaa gaggctagca gccctccaag acagaagtct        360
ctccctagcg tgggcccttc cttggcctgt aatcttgcct ctgagtcccc cgaactcttc        420
ctcattaatc acaagccctg gcaatcaat caggaagagc atctgctcct cctccatctc        480
cgatgtcctc accacctccg                                                    500

<210> SEQ ID NO 14
<211> LENGTH: 480
<212> TYPE: DNA
<213> ORGANISM: Gorilla gorilla

<400> SEQUENCE: 14
cggaggtggt gaggacatcg gagatggagg aggagcagat gctgttcctg attgattgcc         60
cagggcttgt gattaatgag gaagagtttg ggggactcag aggcaagatt acaggccaag        120
gaagggccca cgctagggag agactcccgt cttggagggc tgctagcctc tttcctaccg        180
acagaacatt ttctggagcc actgcagccc cctcactagt gtaaagggaa aggtggacag        240
tcagagtggt gtttaggaca gaaaactcca gcactcctct ctgctgctgg tgttgaatgg        300
tacaagctga aacgcgtctc ttaccactgc tcttctctag ctgggcttca gggcaaacac        360
ttggtcccag ccaagctctc ttggccatat catcaccttc tctctgaccc actgatttgc        420
ctccctcctg tcaccttcca gtacctggac gttaaagttt tacagtaaat ccaatgtttt        480

<210> SEQ ID NO 15
<211> LENGTH: 300
<212> TYPE: DNA
<213> ORGANISM: Homo sapiens

<400> SEQUENCE: 15
ggccaggcgc ggtggctcat gcctgtaatc ccagcacttt gggaggctga ggtaggcgga         60
tcacctgagg ccaggagttg agaccagcc tggccaacat ggtgaaaccc cgtctctact        120
aaaaatgcaa aaattagctg gcgtggtgt cagccgtttg taatcccagc tacttgggag        180
gctgaggcag gagaattgct tgaacccggg aggcggaggt tgcagtgagc cgagatcacg        240
ccattgcact ccagcctggg tgacacaaag agactctatc tgaaaaaaag agaaagaaaa        300

<210> SEQ ID NO 16
<211> LENGTH: 6050
<212> TYPE: DNA
<213> ORGANISM: Homo sapiens

<400> SEQUENCE: 16
ggggggagga gccaagatgg ccgaatagga acagctccgg tctacagctc ccagcgtgag         60
cgacgcagaa gacggtgatt tctgcatttc catctgaggt accgggttca tctcactagg        120
gagtgccaga cagtgggcgc aggccagtgt gtgtgcgcac cgtgcgcgag ccgaagcagg        180
gcgaggcatt gcctcacctg ggaagcgcaa ggggtcaggg agttcccttt ctgagtcaaa        240
gaaaggggtg acggtcgcac ctggaaaatc gggtcactcc caccgaata ttgcgctttt        300 cagaccggct taagaaacgg cgcaccacga gactatatcc cacacctggc tcggagggtc        360
ctacgcccac ggaatctcgc tgattgctag cacagcagtc tgagatcaaa ctgcaaggcg        420
gcaacgaggc tggggagggg cgcccgcca ttgcccaggc ttgcttaggt aaacaaagca        480
```

```
gccgggaagc tcgaactggg tggagcccac cacagctcaa ggaggcctgc ctgcctctgt    540
aggctccacc tctgggggca gggcacagac aaacaaaaag acagcagtaa cctctgcaga    600
cttaagtgtc cctgtctgac agctttgaag agagcagtgg ttctcccagc acgcagctgg    660
agatctgaga acgggcagac agactgcctc ctcaagtggg tccctgactc ctgaccccg     720 agcagcctaa ctggaggca ccccccagca ggggcacact gacacctcac acggcagggt     780
attccaacag acctgcagct gagggtcctg tctgttagaa ggaaaactaa caaccagaaa    840
ggacatctac accgaaaacc catctgtaca tcaccatcat caaagaccaa agtagataa     900 aaccacaaag atggggaaaa aacagaacag aaaaactgga aactctaaaa cgcagagcgc    960
ctctcctcct ccaaaggaac gcagttcctc accagcaaca gaacaaagct ggatggagaa   1020
tgattttgac gagctgagag aagaaggctt cagacgatca aattactctg agctacggga   1080
ggacattcaa accaaaggca agaagttga aactttgaa aaaatttag aagaatgtat      1140 aactagaata accaatacag agaagtgctt aaggagctg atggagctga aaccaaggc     1200 tcgagaacta cgtgaagaat gcagaagcct caggagccga tgcgatcaac tggaagaaag   1260
ggtatcagca atgaagatg aaatgaatga aatgaagcga aagggaagt ttagagaaaa     1320 aagaataaaa agaaatgagc aaagcctcca agaaatatgg gactatgtga aaagaccaaa   1380
tctacgtctg attggtgtac ctgaaagtga tgtggagaat ggaaccaagt tggaaaacac   1440
tctgcaggat attatccagg agaacttccc caatctagca aggcaggcca acgttcagat   1500
tcaggaaata cagagaacgc cacaaagata ctcctcgaga agagcaactc caagacacat   1560
aattgtcaga ttcaccaaag ttgaaatgaa ggaaaaaatg ttaagggcag ccagagagaa   1620
aggtcgggtt accctcaaag gaaagccat cagactaaca gtggatctct cggcagaaac    1680
cctacaagcc agaagagagt gggggccaat attcaacatt cttaaagaaa agaattttca   1740
acccagaatt tcatatccag ccaaactaag cttcataagt gaaggagaaa taaaatactt   1800
tatagacaag caaatgttga gagattttgt caccaccagg cctgccctaa aagagctcct   1860
gaaggaagca ctaaacatgg aaaggaacaa ccggtaccag ccgctgcaaa atcatgccaa   1920
aatgtaaaga ccatcgagac taggaagaaa ctgcatcaac taatgagcaa atcaccagc    1980 taacatcata atgacaggat caaattcaca cataacaata ttaactttaa atataaatgg   2040
actaaattct gcaattaaaa gacacagact ggcaagttgg ataaagagtc aagacccatc   2100
agtgtgctgt attcaggaaa cccatctcac gtgcagagac acacataggc tcaaaataaa   2160
aggatggagg aagatctacc aagccaatgg aaaacaaaaa aaggcagggg ttgcaatcct   2220
agtctctgat aaaacagact ttaaaccaac aaagatcaaa agagacaaag aaggccatta   2280
cataatggta aagggatcaa ttcaacaaga ggagctaact atcctaaata tttatgcacc   2340
caatacagga gcacccagat tcataaagca agtcctcagt gacctacaaa gagacttaga   2400
ctcccacaca ttaataatgg gagactttaa caccccactg tcaacattag acagatcaac   2460
gagacagaaa gtcaacaagg atacccagga attgaactca gctctgcacc aagcagacct   2520
aatagacatc tacagaactc tccacccaa atcaacagaa tatcctttt tttcagcacc     2580 acaccacacc tattccaaaa ttgaccacat agttggaagt aaagctctcc tcagcaaatg   2640
taaaagaaca gaaattataa caaactatct ctcagaccac agtgcaatca actagaact    2700 caggattaag aatctcactc aaagccgctc aactacatgg aaactgaaca acctgctcct   2760
gaatgactac tgggtacata cgaaatgaa ggcagaaata aagatgttct ttgaaaccaa    2820
cgagaacaaa gacaccacat accagaatct ctgggacgca ttcaaagcag tgtgtagagg   2880
```

| | |
|---|---|
| gaaatttata gcactaaatg cctacaagag aaagcaggaa agatccaaaa ttgacaccct | 2940 |
| aacatcacaa ttaaaagaac tagaaaagca agagcaaaca cattcaaaag ctagcagaag | 3000 |
| gcaagaaata actaaaatca gagcagaact gaaggaaata gagacacaaa aaacccttca | 3060 |
| aaaaatcaat gaatccggga gctggttttt tgaaaggatc aacaaaattg atagaccgct | 3120 |
| agcaagacta ataagaaaaa aagagagaa gaatcaaata gacacaataa aaatgataa | 3180 |
| aggggatatc accaccgatc ccacagaaat acaaactacc atcagagaat actacaaaca | 3240 |
| cctctacgca aataaactag aaaatctaga agaaatggat acattcctcg acacatacac | 3300 |
| tctcccaaga ctaaaccagg aagaagttga atctctgaat agaccaataa caggctctga | 3360 |
| aattgtggca ataatcaata gtttaccaac caaaaagagt ccaggaccag atggattcac | 3420 |
| agccgaattc taccagaggt acatggagga actggtacca ttccttctga aactattcca | 3480 |
| atcaatagaa aaagagggaa tcctccctaa ctcattttat gaggccagca tcattctgat | 3540 |
| accaaagccg ggcagagaca caaccaaaaa agagaatttt agaccaatat ccttgatgaa | 3600 |
| cattgatgca aaaatcctca ataaaatact ggcaaaccga atccagcagc acatcaaaaa | 3660 |
| gcttatccac catgatcaag tgggcttcat ccctgggatg caaggctggt tcaatatacg | 3720 |
| caaatcaata aatgtaatcc agcatataaa cagagccaaa gacaaaaacc acatgattat | 3780 |
| ctcaatagat gcagaaaaag cctttgacaa aattcaacaa cccttcatgc taaaaactct | 3840 |
| caataaatta ggtattgatg ggacgtattt caaaataata agagctatct atgacaaacc | 3900 |
| cacagccaat atcatactga atgggcaaaa actggaagca ttcccttga aaccggcac | 3960 |
| aagacaggga tgccctctct caccgctcct attcaacata gtgttggaag ttctggccag | 4020 |
| ggcaatcagg caggagaagg aaataaaggg tattcgatta ggaaaagagg aagtcaaatt | 4080 |
| gtccctgttt gcagacgaca tgattgtata tctagaaaac cccatcgtct cagcccaaaa | 4140 |
| tctccttaag ctgataagca acttcagcaa agtctcagga tacaaaatca atgtacaaaa | 4200 |
| atcacaagca ttcttataca ccaacaacag acaaacagag agccaaatca tgggtgaact | 4260 |
| cccattcgta attgcttcaa agagaataaa atacctagga atccaactta caagggatgt | 4320 |
| gaaggacctc ttcaaggaga actacaaacc actgctcaag gaaataaaag aggacacaaa | 4380 |
| caaatggaag aacattccat gctcatgggt aggaagaatc aatatcgtga aaatggccat | 4440 |
| actgcccaag gtaatttaca gattcaatgc catccccatc aagctaccaa tgactttctt | 4500 |
| cacagaattg gaaaaaacta ctttaaagtt catatggaac caaaaagag cccgcattgc | 4560 |
| caagtcaatc ctaagccaaa agaacaaagc tggaggcatc acactacctg acttcaaact | 4620 |
| atactacaag gctacagtaa ccaaaacagc atggtactgg taccaaaaca gagatataga | 4680 |
| tcaatggaac agaacagagc cctcagaaat aatgccgcat atctacaact atctgatctt | 4740 |
| tgacaaacct gagaaaaaca agcaatgggg aaaggattcc ctatttaata aatggtgctg | 4800 |
| ggaaaactgg ctagccatat gtagaaagct gaaactggat cccttcctta cccttatac | 4860 |
| aaaaatcaat tcaagatgga ttaaagattt aaacgttaaa cctaaaacca taaaaaccct | 4920 |
| agaagaaaac ctaggcatta ccattcagga cataggcgtg gcaaggact tcatgtccaa | 4980 |
| aacaccaaaa gcaatggcaa caaaagacaa aattgacaaa tgggatctaa ttaaactaaa | 5040 |
| gagcttctgc acagcaaaag aaactaccat cagagtgaac aggcaaccta caacatggga | 5100 |
| gaaaattttc gcaacctact catctgacaa agggctaata tccagaatct acaatgaact | 5160 |
| caaacaaatt tacaagaaaa aaacaaacaa ccccatcaaa aagtgggcga aggacatgaa | 5220 |
| cagacacttc tcaaaagaag acatttatgc agccaaaaaa cacatgaaga aatgctcatc | 5280 |

```
atcactggcc atcagagaaa tgcaaatcaa aaccactatg agatatcatc tcacaccagt    5340
tagaatggca atcattaaaa agtcaggaaa caacaggtgc tggagaggat gcggagaaat    5400
aggaacactt ttacactgtt ggtgggactg taaactagtt caaccattgt ggaagtcagt    5460
gtggcgattc ctcagggatc tagaactaga ataccatttt gacccagcca tcccattact    5520
gggtatatac ccaaatgagt ataaatcatg ctgctataaa gacacatgca cacgtatgtt    5580
tattgcggca ctattcacaa tagcaaagac ttggaaccaa cccaaatgtc caacaatgat    5640
agactggatt aagaaaatgt ggcacatata caccatggaa tactatgcag ccataaaaaa    5700
tgatgagttc atatcctttg tagggacatg gatgaaattg gaaaccatca ttctcagtaa    5760
actatcgcaa gaacaaaaaa ccaaacaccg catattctca ctcataggtg ggaattgaac    5820
aatgagatca catggacaca ggaagggaaa tatcacactc tggggactgt ggtgggtcg    5880 ggggagggggg gagggatagc attgggagat atacctaatg ctagatgaca cattagtggg    5940
tgcagcgcac cagcatggca catgtataca tatgtaacta acctgcacaa tgtgcacatg    6000
taccctaaaa cttagagtat aataaaaaaa aaaaaaaaaa aaaaaaaaaa                6050
```

```
<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agagcagaac tgaaggaaat agagac                                          26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccaagcagac ctaatagaca tctaca                                          26

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atagttggaa gtaaagctct cctcag                                          26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcctcagtga cctacaaaga gactta                                          26

<210> SEQ ID NO 21
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atacattcct cgacacatac actctc                                              26

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcctgaatga ctactgggta cataac                                              26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctacaaggct acagtaacca aaacag                                              26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cctaatgcta gatgacacat tagtgg                                              26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctaacaacca gaaaggacat ctacac                                              26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctcttcaagg agaactacaa accact                                              26

<210> SEQ ID NO 27
<211> LENGTH: 26
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 27
atacagagaa gtgcttaaag gagctg                                         26

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aagtcgcggc cgcttgcagt gagccgagat                                     30

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgacctcgag atctyrgctc actgcaa                                        27

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccgaattcgc ctcccaaagt gctgggatta cag                                 33

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
actcgggagg ctgaggcagg                                                20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctcggctcac tgcaaactcc                                                20

<210> SEQ ID NO 33
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 33
atcgcatgaa cccgggaggc                                                 20

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcatcgatag atyryrccay tgcact                                          26

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cttttctcca catccttgcc agcatt                                          26

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgccatgagc ttgtctacac ctatcgg                                         27

<210> SEQ ID NO 37
<211> LENGTH: 29
<212> TYPE: DNA
<213> ORGANISM: Homo sapiens

<400> SEQUENCE: 37
ctctggcctt gtctccacct agaccacaa                                       29

<210> SEQ ID NO 38
<211> LENGTH: 27
<212> TYPE: DNA
<213> ORGANISM: Homo sapiens

<400> SEQUENCE: 38
gatgctgatc atgtctccac ctccttg                                         27

<210> SEQ ID NO 39
<211> LENGTH: 30
<212> TYPE: DNA
<213> ORGANISM: Homo sapiens

<400> SEQUENCE: 39
ttgtaaccca gtctacacct tgatgagatc                                      30

<210> SEQ ID NO 40
<211> LENGTH: 26
<212> TYPE: DNA
```

<213> ORGANISM: Homo sapiens

<400> SEQUENCE: 40
ttgtttgctc ttgtccacac ctgcat 26

<210> SEQ ID NO 41
<211> LENGTH: 30
<212> TYPE: DNA
<213> ORGANISM: Homo sapiens

<400> SEQUENCE: 41
aattctcagc ttgatctaca cctgaacctt 30

<210> SEQ ID NO 42
<211> LENGTH: 32
<212> TYPE: DNA
<213> ORGANISM: Homo sapiens

<400> SEQUENCE: 42
aagtcttagc ttgcctaccc ctagattact tc 32

<210> SEQ ID NO 43
<211> LENGTH: 32
<212> TYPE: DNA
<213> ORGANISM: Homo sapiens

<400> SEQUENCE: 43
tctttccttg tgctgtccac accttctgac ta 32

<210> SEQ ID NO 44
<211> LENGTH: 28
<212> TYPE: DNA
<213> ORGANISM: Homo sapiens

<400> SEQUENCE: 44
ggtctgtctt gcccacacct agagtgac 28

<210> SEQ ID NO 45
<211> LENGTH: 25
<212> TYPE: DNA
<213> ORGANISM: Homo sapiens

<400> SEQUENCE: 45
gggggttctt gtctcctcct cacgg 25

<210> SEQ ID NO 46
<211> LENGTH: 31
<212> TYPE: DNA
<213> ORGANISM: Homo sapiens

<400> SEQUENCE: 46
gctgccacac ctgggcttta cacctcccac t 31

<210> SEQ ID NO 47
<211> LENGTH: 28
<212> TYPE: DNA
<213> ORGANISM: Mus sp.

<400> SEQUENCE: 47
caaataaaag catctctaca ccttgcac 28

<210> SEQ ID NO 48
<211> LENGTH: 27
<212> TYPE: DNA

```
<213> ORGANISM: Mus sp.

<400> SEQUENCE: 48
ctgggggaag cttgctccac ctttgat                                          27

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
atgactaatg cggttt                                                      16

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atgactgatg cggat                                                       15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttgactaatg cggat                                                       15

<210> SEQ ID NO 52
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
actgactgga ctgactgact ggactgactg actggactga c                          41
```